(12) United States Patent
Poetsch et al.

(10) Patent No.: US 7,888,519 B2
(45) Date of Patent: Feb. 15, 2011

(54) PYRAN COMPOUND OR AT LEAST ONE DERIVATIVE THEREOF

(75) Inventors: Eike Poetsch, Muehltal (DE); Werner Binder, Dieburg (DE); Volker Meyer, Gross-Zimmern (DE); Michael Heckmeier, Hemsbach (DE); Georg Luessem, Petershausen (DE)

(73) Assignee: Merck Patent Gesellschaft, Darmstadt (DE)

( * ) Notice: Subject to any disclaimer, the term of this patent is extended or adjusted under 35 U.S.C. 154(b) by 1708 days.

(21) Appl. No.: 10/854,718

(22) Filed: May 27, 2004

(65) Prior Publication Data

US 2005/0017216 A1  Jan. 27, 2005

(30) Foreign Application Priority Data

May 27, 2003  (DE)  ............... 103 24 312

(51) Int. Cl.
 *C07D 315/00*  (2006.01)
(52) U.S. Cl. ...................... 549/427; 549/428
(58) Field of Classification Search ................. 549/427, 549/428
 See application file for complete search history.

(56) References Cited

U.S. PATENT DOCUMENTS

| | | | | |
|---|---|---|---|---|
| 4,818,431 | A * | 4/1989 | Eidenschink et al. ... | 252/299.61 |
| 5,149,462 | A * | 9/1992 | Sakashita et al. ....... | 252/299.61 |
| 5,387,689 | A | 2/1995 | Reiffenrath et al. | |
| 5,480,580 | A | 1/1996 | Sakashita et al. | |
| 5,811,028 | A * | 9/1998 | Ishizuka et al. ........ | 252/299.61 |
| 6,146,718 | A | 11/2000 | Yano et al. | |
| 6,329,027 | B1 * | 12/2001 | Kondo et al. ................. | 428/1.1 |
| 6,558,758 | B1 * | 5/2003 | Yanai et al. .................. | 428/1.1 |
| 6,902,777 | B2 * | 6/2005 | Hirschmann et al. ......... | 428/1.1 |
| 2002/0019534 | A1 | 2/2002 | Noe et al. | |
| 2002/0130300 | A1 | 9/2002 | Bremer et al. | |
| 2002/0165222 | A1 | 11/2002 | Marquis, Jr. et al. | |

FOREIGN PATENT DOCUMENTS

| CA | 2 342 271 | | 9/2001 |
|---|---|---|---|
| DE | 3306960 | A1 | 8/1984 |
| DE | 196 40 618 | | 4/1998 |
| DE | 19640618 | A1 | 4/1998 |
| EP | 0409066 | A2 | 1/1991 |
| JP | 59-164788 | | 9/1984 |
| JP | 01-503387 | | 11/1989 |
| JP | 3 261 779 | | 11/1991 |
| JP | 06-025210 | | 2/1994 |
| JP | 6-211865 | | 8/1994 |
| JP | 11-349582 | | 12/1999 |
| JP | 2001 72626 | | 3/2001 |
| JP | 2001-316383 | | 11/2001 |
| JP | 2002-128776 | | 5/2002 |
| JP | 2002 193853 | | 7/2002 |
| JP | 2002-537297 | | 11/2002 |
| WO | WO-88 09322 | | 12/1988 |
| WO | WO-00-49011 | | 8/2000 |

OTHER PUBLICATIONS

Remizov et al DN 65:3637 (1965).*
Ritter DN 62:92853 (1964).*
Schmidt, B. et al. "A Synthesis of Densely Functionalized 2,3-Dihydropyrans Using Ring-Closing Metathesis and Base-Induced Rearrangements of Dihydropyran Oxides", Eur. J. Org. Chem., 3145-3163 (2000).
Carda, M. et al., "Stereoselective synthesis of (--)—malyngolide, (+)-malyngolide and (+)-tanikolide using ring-closing metathesis," Tetrahedron, 2003, vol. 59, pp. 854-864.
Chisso Corp, "New Liquid Crystalline Compound Having Negative Dieleclectric Anisotropy Value, Liquid Crystal Composition and Liquid Crystal," Data supplied from the espacenet database, Publication Date: Mar. 21, 2001; Eng Abst of JP2001 72626.
Dainippon Ink & Chemicals, "Optically active 5, 6-Dihydro-2-Pyrone Derivative, It's Production and Liquid Crystal Composition and Liquid Crystal Display Element Containing the Same Derivative," Date supplied from the espacenet database, Publication Date: Feb. 1, 1994; Eng Abst of JP 6 025 210.
Furstner, A. et al., "Ruthenium Carbene Complexes with N, N-Bis(mesityl) imidazol-2-ylidene Ligands: RCM Catalysts of Extended Scope," J. Org. Chem., 2000, vol. 65, pp. 2204-2207.
Merck Patent GmbH, "Tetracyclic compound with negative dielectric constant anisotropy and liquid crystalline medium," Patent Abstracts of Japan, Publication Date: Jul. 10, 2002; Eng Abst of JP 2002 193853.
Mitsubishi Petrochemical Co., "Optically active compound and liquid crystal composition containing the same," Data Supplied from the espacenet database, Publication Date: Nov. 21, 1991; Eng Abst of JP 3 261 779.
Office Action for related Japanese Patent Application No. 2004-157022 dated Aug. 24, 2010.
Thomson Innovation, English Translation of Claims and Description, Data Retrieved from Patent Record View on Oct. 6, 2010; Eng Abstract of WO-88 09322.
BASF AG, "Chirale Verbindungen," Data Supplied from the espacenet database, Publication Date: Apr. 2, 1998; Eng Abst of DE 196 40 618.

* cited by examiner

*Primary Examiner*—Janet L. Andres
*Assistant Examiner*—Raymond Covington
(74) *Attorney, Agent, or Firm*—Millen, White, Zelano & Branigan, P.C.

(57) ABSTRACT

The invention relates to pyran derivatives of the formula I

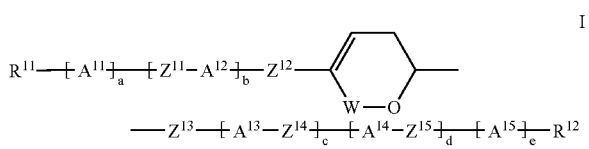

and to a process and intermediates for their preparation and derivatisation, and to the use thereof in liquid-crystalline media.

65 Claims, No Drawings

PYRAN COMPOUND OR AT LEAST ONE DERIVATIVE THEREOF

The invention relates to a pyran compound, or one or more derivatives thereof, to a process for their preparation and derivatisation, and to the use thereof in liquid-crystalline media.

Pyran derivatives play an important role in chemistry and pharmacy, inter alia as ingredients of natural and synthetic aroma substances, in medicaments and in liquid-crystalline materials. However, preparative access to many pyrans, in particular those with a 2,5-disubstitution, is currently limited and, is often restricted to derivatization of carbohydrates containing pyranose ring units. Many theoretically conceivable pyran derivatives are hitherto not accessible synthetically.

It is therefore an object of the present invention to provide novel pyran derivatives which have industrially useful properties or can serve as starting compounds for the efficient synthesis of further pyran derivatives.

This object is achieved by compounds of the general formula I

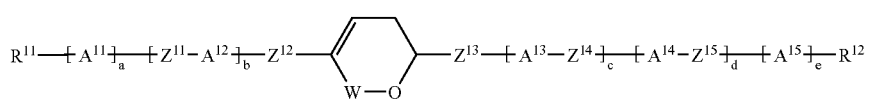

I where
a, b, c, d and e are each, independently of one another, 0 or 1;
W is —$CH_2$— or —C(=O)—;
$R^{11}$ is H, an alkyl radical having from 1 to 15 carbon atoms which is unsubstituted or mono- or polysubstituted, identically or differently, by halogen or —CN, where, in addition, one or more $CH_2$ groups in this radical may be replaced by —C≡C—, —CH=CH—, —O—, —S—, —C(O)—O— and/or —O—C(O)— in such a way that hetero atoms (O and S) are not linked directly to one another;
$R^{12}$ is H, halogen, —CN, —NCS, aralkyl, O-aralkyl or an alkyl radical having from 1 to 15 carbon atoms which is unsubstituted or mono- or polysubstituted, identically or differently, by halogen or —CN, where, in addition, one or more $CH_2$ groups in this radical may be replaced by —C≡C—, —CH=CH—, —O—, —S—, —C(O)—O— and/or —O—C(O)— in such a way that hetero atoms (O and S) are not linked directly to one another;
$Z^{11}$ is a single bond, —$CH_2$—, —$CH_2CH_2$—, —$CF_2CH_2$—, —$CH_2CF_2$—, —$CF_2CF_2$—, —CH=CH— or —C≡C—;
$Z^{12}$ is a single bond, —$CH_2$—, —$CH_2CH_2$—, —$CF_2CH_2$—, —$CH_2CF_2$— or —$CF_2CF_2$—;
$Z^{13}$, $Z^{14}$ and $Z^{15}$ are each, independently of one another, a single bond, —$CH_2CH_2$—, —$CF_2CH_2$—, —$CH_2CF_2$—, —$CF_2CF_2$—, —CH=CH—, —C≡C—, —$CH_2O$—, —$CF_2O$—, —C(O)— or —C(O)—O—;
$A^{11}$ and $A^{12}$, independently of one another, are

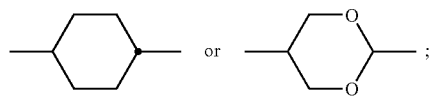

or
$A^{13}$ and $A^{14}$, independently of one another, are

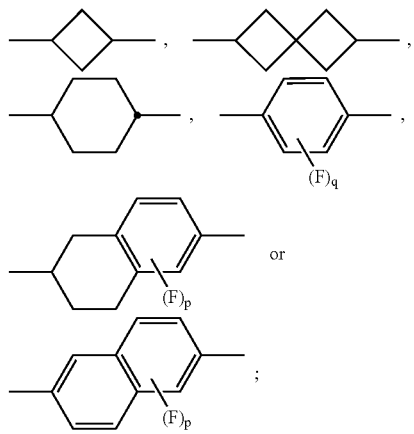

$A^{15}$ is

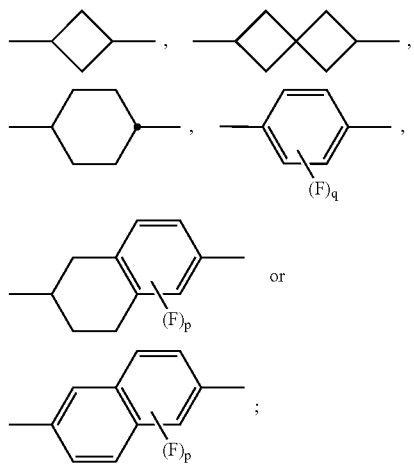

or
$A^{15}$-$R^{12}$ together are

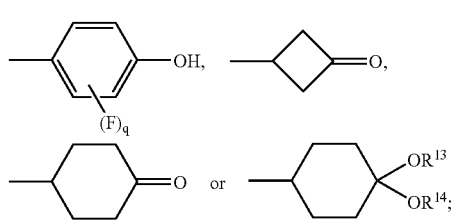

or
$Z^{13}$-[-$A^{13}$-$Z^{14}$-]$_c$-[-$A^{14}$-$Z^{15}$-]$_d$-[-$A^{15}$-]$_e$-$R^{12}$ is or

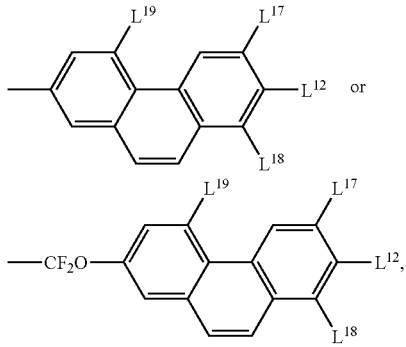

where $R^{12}$ is as defined above, and $L^{17}$, $L^{18}$ and $L^{19}$, independently of one another, are H or F;

q is 0, 1, 2, 3 or 4;

p is 0, 1, 2 or 3;

$R^{13}$ and $R^{14}$, independently of one another, are an alkanyl radical having from 1 to 7 carbon atoms or together are an alkylene bridge having from 2 to 7 carbon atoms;

with the proviso that, in the case of direct linking of $Z^{13}$ and $R^{12}$ to give —$Z^{13}$—$R^{12}$, $R^{12}$ is H, aralkyl, alkanyl or alkenyl if $Z^{13}$ is —C(=O)—O— or —C(=O)—, and $Z^{13}$ is not —CH$_2$O— or —CF$_2$O—;

that, in the case of direct linking of $Z^{14}$ and $R^{12}$ to give —$Z^{14}$—$R^{12}$, $R^{12}$ is H, aralkyl, alkanyl or alkenyl if $Z^{14}$ is —C(=O)—O— or —C(=O)—, and $Z^{14}$ is not —CH$_2$O— or —CF$_2$O—;

that, in the case of direct linking of $Z^{15}$ and $R^{12}$ to give —$Z^{15}$—$R^{12}$, $R^{12}$ is H, aralkyl, alkanyl or alkenyl if $Z^{15}$ is —C(=O)—O— or —C(=O)—, and $Z^{15}$ is not —CH$_2$O— or —CF$_2$O—;

that $R^{11}$ is not H if simultaneously a and b are both zero and $Z^{12}$ is a single bond;

that $R^{11}$ is not CH$_3$ if simultaneously a and b are both zero, $Z^{12}$ and $Z^{13}$ are each a single bond, W is —CH$_2$— and -[-$A^{13}$-$Z^{14}$-]$_c$-[-$A^{14}$-$Z^{15}$-]$_d$-[-$A^{15}$-]$_e$-$R^{12}$ is unsubstituted phenyl.

On the basis of their properties, the compounds of the formula I according to the invention are used in liquid-crystalline media or serve as starting compounds for the efficient synthesis of further pyran compounds, in particular those having mesogenic properties. The compounds of the formula I according to the invention are preferably mesogenic, in particular liquid-crystalline.

In connection with the present invention, the term "alkyl"—unless defined otherwise elsewhere in this description or in the claims—denotes a straight-chain or branched aliphatic hydrocarbon radical having from 1 to 15 (i.e. 1, 2, 3, 4, 5, 6, 7, 8, 9, 10, 11, 12, 13, 14 or 15) carbon atoms; this radical is unsubstituted or mono- or polysubstituted by identical or different fluorine, chlorine, bromine, iodine and/or cyano radicals.

If this alkyl radical is a saturated radical, it is also referred to as "alkanyl" (C$_a$H$_{2a+1}$—, where a is an integer from 1 to 15 and one or more hydrogen atoms may be replaced by halogen, in particular fluorine, and/or cyano). Furthermore, the term "alkyl" also covers hydrocarbon radicals which are unsubstituted or correspondingly mono- or polysubstituted by identical or different F, Cl, Br, I and/or —CN radicals and in which, in addition, one or more CH$_2$ groups may be replaced by —O— ("alkoxy", "oxaalkyl"), —S— ("thioalkyl"), —CH=CH— ("alkenyl"), —C≡C— ("alkynyl"), —CO—O— or —O—CO— in such a way that hetero atoms (O and S) are not linked directly to one another. Alkyl is preferably a straight-chain or branched, unsubstituted or substituted alkanyl, alkenyl or alkoxy radical having 1, 2, 3, 4, 5, 6, 7 or 8 carbon atoms. If alkyl is an alkanyl radical, this is preferably methyl, ethyl, n-propyl, i-propyl, n-butyl, i-butyl, t-butyl, n-pentyl, neopentyl, n-hexyl, n-heptyl, n-octyl; CF$_3$, CHF$_2$, CH$_2$F; CF$_2$CF$_3$. The alkanyl radical is particularly preferably straight-chain and unsubstituted or substituted by F.

Since, in accordance with the invention, one or more CH$_2$ groups in an alkyl radical may be replaced by —O—, the term "alkyl" also covers "alkoxy" or "oxaalkyl" radicals. Alkoxy is taken to mean an O-alkyl radical in which the oxygen atom is bonded directly to the group substituted by the alkoxy radical or to the substituted ring, and alkyl is as defined above; alkyl is preferably then alkanyl or alkenyl. Preferred alkoxy radicals are methoxy, ethoxy, propoxy, butoxy, pentoxy, hexoxy, heptoxy and octoxy, where each of these radicals may also be substituted by halogen or cyano, preferably by one or more fluorine atoms. Alkoxy is particularly preferably —OCH$_3$, —OC$_2$H$_5$, —O-n-C$_3$H$_7$, —O-n-C$_4$H$_9$, —O-t-C$_4$H$_9$, —OCF$_3$, —OCHF$_2$, —OCH$_2$F or —OCHFCHF$_2$.

In connection with the present invention, the term "oxaalkyl" denotes alkyl radicals in which at least one non-terminal CH$_2$ group has been replaced by —O— in such a way that no adjacent hetero atoms (O and S) are present. Oxaalkyl preferably covers straight-chain radicals of the formula —C$_a$H$_{2a+1}$—O—(CH$_2$)$_b$—, where a and b are each, independently of one another, 1, 2, 3, 4, 5, 6, 7, 8, 9 or 10; a is particularly preferably an integer from 1 to 6, and b is 1 or 2.

If one or more CH$_2$ groups in an alkyl radical as defined above have been replaced by sulfur, a "thioalkyl" radical is present. "Thioalkyl" preferably covers a straight-chain radical of the formula —C$_a$H$_{2a+1}$—S—(CH$_2$)$_b$—, where a is 1, 2, 3, 4, 5, 6, 7, 8, 9 or 10, and b is 0, 1, 2, 3, 4, 5, 6, 7, 8, 9 or 10; a is particularly preferably an integer from 1 to 6, and b is 0, 1 or 2. The thioalkyl radical may likewise be substituted by F, Cl, Br, I and/or —CN and is preferably unsubstituted.

In connection with the present invention, the term "alkenyl" denotes an alkyl radical as defined above in which one or more —CH=CH— groups are present. If two —CH=CH— groups are present in the radical, this may also be referred to as "alkadienyl". An alkenyl radical may contain from 2 to 15 (i.e. 2, 3, 4, 5, 6, 7, 8, 9, 10, 11, 12, 13, 14 or 15) carbon atoms and is branched or preferably straight-chain. The radical is unsubstituted or mono- or polysubstituted by identical or different F, Cl, Br, I and/or CN radicals. Furthermore, one or more CH$_2$ groups may each, independently of one another, be replaced by —O—, —S—, —C≡C—, —CO—O— or —OC—O— in such a way that hetero atoms (O and S) are not bonded directly to one another. If the CH=CH group carries a radical other than hydrogen on the two carbon atoms, for example if it is a non-terminal group, the CH=CH group can exist in two configurations, namely as the E isomer and the Z isomer. In general, the E isomer (trans) is preferred. The alkenyl radical preferably contains 2, 3, 4, 5, 6 or 7 carbon atoms and is vinyl, 1E-propenyl, 1E-butenyl, 1E-pentenyl, 1E-hexenyl, 1E-heptenyl, 2-propenyl, 2E-butenyl, 2E-pentenyl, 2E-hexenyl, 2E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl or 6-heptenyl. Particularly preferred alkenyl radicals are vinyl, 1E-propenyl and 3E-butenyl.

If one or more $CH_2$ groups in an alkyl radical have been replaced by —C≡C—, an alkynyl radical is present. Replacement of one or more $CH_2$ groups by —CO—O— or —O—CO— is also possible. The following radicals are preferred here: acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 2-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl and 4-(methoxycarbonyl)butyl.

If a $CH_2$ group in an alkyl radical has been replaced by unsubstituted or substituted —CH=CH— and an adjacent $CH_2$ group has been replaced by —CO—O— or —O—CO—, this radical may be straight-chain or branched. It is preferably straight-chain and has from 4 to 13 carbon atoms. Accordingly, it is particularly preferably acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

In connection with the present invention, the term "aralkyl" represents an arylalkyl radical, i.e. a radical in which an aryl substituent is linked to an atom, a chain, another radical or a functional group via an alkyl bridge. The term "O-aralkyl" represents an arylalkoxy radical, i.e. a radical in which an arylalkyl substituent is linked to an atom, a chain, another radical or a functional group via an oxygen atom. The term aryl substituent here is taken to mean an aromatic hydrocarbon having from 6 to 18 carbon atoms which is optionally substituted by halogen, nitro, alkanyl and/or alkoxy radicals, in particular a phenyl or naphthyl radical. The alkyl bridge is preferably a saturated hydrocarbon radical, in particular methylene (—$CH_2$—) or ethylene (—$CH_2CH_2$—). Preferred examples of an aralkyl radical are benzyl and phenethyl. Preferred examples of an O-aralkyl radical are O-benzyl (—O—$CH_2$-phenyl), O-phenethyl (—O—$CH_2CH_2$-phenyl) and O-(p-nitrobenzyl).

In accordance with the invention, "alkylene bridge" means an aliphatic hydrocarbon chain which is unbranched or branched and has the formula —$C_nH_{2n}$—, for example —$CH_2CH_2$—, —$CH_2CH_2CH_2$— or —$CH_2C(CH_3)_2CH_2$—.

In connection with the present invention, "halogen" covers fluorine, chlorine, bromine and iodine.

If radicals or substituents of the pyran derivatives according to the invention or the pyran derivatives according to the invention themselves can be in the form of optically active or stereoisomeric radicals, substituents or compounds since they have, for example, a center of asymmetry, these are also covered by the present invention. It goes without saying here that the pyran derivatives of the general formulae I and III according to the invention can be in isomerically pure form, for example as pure enantiomers, diastereomers, E or Z isomers, trans or cis isomers, or in the form of a mixture of a plurality of isomers in any desired ratio, for example in the form of a racemate, E/Z isomer mixture or cis/trans isomer mixture.

The compounds of the formula I according to the invention preferably contain a total of not more than four ring systems, including the central pyran ring, so that a+b+c+d+e is $\leq 3$; particularly preferably $1 \leq a+b+c+d+e \leq 3$, i.e. at least one further ring system and not more than three further ring systems are present besides the pyran ring. It is furthermore preferred for $R^{11}$ to be a straight-chain alkenyl or particularly preferably a straight-chain alkanyl radical having from 1 to 7 carbon atoms, in particular methyl, and for $R^{12}$ to be halogen, in particular fluorine, or an unbranched alkanyl or alkoxy radical having from 1 to 5 carbon atoms which is optionally mono- or polysubstituted by halogen, in particular fluorine.

Compounds of the formula I containing branched wing groups $R^{11}$ and/or $R^{12}$ may occasionally be of importance on use in liquid-crystalline media owing to their very good solubility in the usual liquid-crystalline base materials, but in particular as chiral dopants if they are optically active. Smectic compounds of this type are suitable as components of ferroelectric materials. Branched groups of this type generally contain not more than one chain branch. Preferred branched radicals $R^{11}$ and $R^{12}$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentyloxy, 3-methylpentyloxy, 2-ethylhexyloxy, 1-methylhexyloxy and 1-methylheptyloxy.

A preferred class of compounds of the formula I according to the invention is formed by pyran derivatives in which W in the formula I is a carbonyl group, i.e. —C(=O)—. The compounds are then lactones of the general formula I-A:

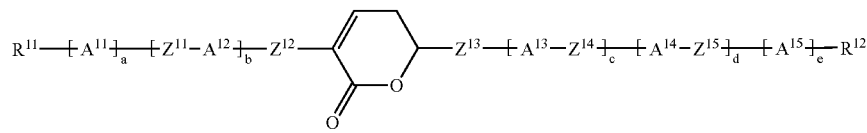

where a, b, c, d, e, $R^{11}$, $R^{12}$, $Z^{11}$, $Z^{12}$, $Z^{13}$, $Z^{14}$, $Z^{15}$, $A^{11}$, $A^{12}$, $A^{13}$, $A^{14}$ and $A^{15}$ are as defined for the formula I above.

Another preferred class of compounds of the formula I according to the invention is formed by pyran derivatives in which W in the formula I is a methylene group, i.e. —$CH_2$—. The compounds are then dihydropyrans of the general formula I-B:

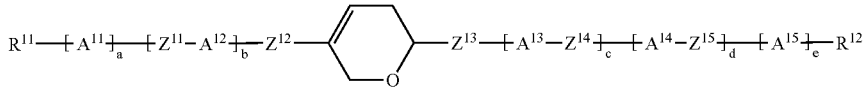

I-B where a, b, c, d, e, $R^{11}$, $R^{12}$, $Z^{11}$, $Z^{12}$, $Z^{13}$, $Z^{14}$, $Z^{15}$, $A^{11}$, $A^{12}$, $A^{13}$, $A^{14}$ and $A^{15}$ are as defined for the formula I above.

In connection with the present invention, the compounds of the formula I according to the invention are also referred to as "pyran derivatives"; the term "pyran derivatives" covers both pyrans of the formula I-B and lactones of the formula I-A.

Preferred embodiments of the invention are furthermore compounds of the formula I in which $Z^{12}$ is a single bond and the central pyran ring is bonded either directly to $R^{11}$ (a=b=0) or to ring $A^{11}$ (a=1; b=0) or to ring $A^{12}$ (a=0; b=1) (formula I-C):

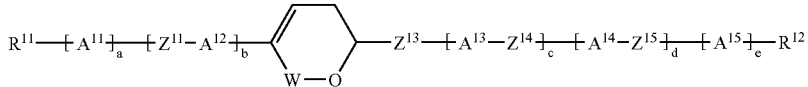

I-C where a, b, c, d, e, W, $R^{11}$, $R^{12}$, $Z^{11}$, $Z^{13}$, $Z^{14}$, $Z^{15}$, $A^{11}$, $A^{12}$, $A^{13}$, $A^{14}$ and $A^{15}$ are as defined for the formula I above. Preferred sub-groups of compounds of the formula I-C are formed here by compounds of the formula I-CA where W is —C(=O)— and in particular by compounds of the formula I-CB where W is —CH$_2$—:

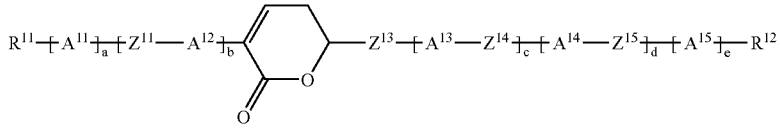

I-CA

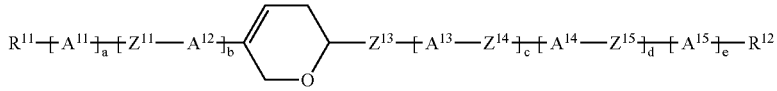

I-CB where a, b, c, d, e, $R^{11}$, $R^{12}$ $Z^{11}$, $Z^{13}$ $Z^{14}$ $Z^{15}$, $A^{11}$, $A^{12}$ $A^{13}$, $A^{14}$ and $A^{15}$ are as defined for the formula I above. Particular preference is given here to compounds in which a=b=0 and $R^{11}$ is alkanyl in the formula I-CA or I-CB.

Preferred compounds of the invention are in addition those in which b is 1, $Z^{11}$ is a single bond and $A^{12}$ is a 1,4-cyclohexylene ring (formula I-D):

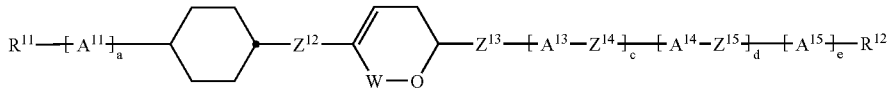

I-D where a, c, d, e, W, $R^{11}$, $R^{12}$, $Z^{12}$, $Z^{13}$, $Z^{14}$, $Z^{15}$, $A^{11}$, $A^{13}$, $A^{14}$ and $A^{15}$ are as defined for the formula I above.

Preferred sub-groups of compounds of the formula I-D are formed here by compounds of the formula I-DA where W is —C(=O)— and in particular by compounds of the formula I-DB where W is —CH$_2$—.

Particular preference is given here to compounds of the formula. I-DB in which furthermore $Z^{12}$ is a single bond (formula I-DBA):

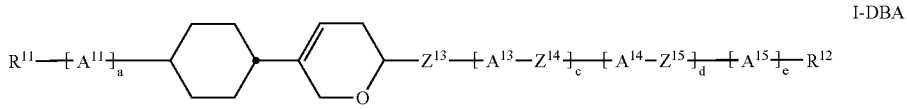

I-DBA where a, c, d, e, $R^{11}$, $R^{12}$, $Z^{13}$, $Z^{14}$, $Z^{15}$, $A^{11}$, $A^{13}$, $A^{14}$ and $A^{15}$ are as defined for the formula I above. It is very particularly preferred here for $Z^{13}$ to be a single bond or —CF$_2$O—, c and d both simultaneously to be zero and $A^{15}$ to be a 1,4-phenylene ring which is optionally mono- or polysubstituted by fluorine.

A further group of preferred compounds according to the invention is formed by compounds of the formula I-E, i.e. compounds of the formula I where a=1 and $A^{11}$=1,4-cyclohexylene:

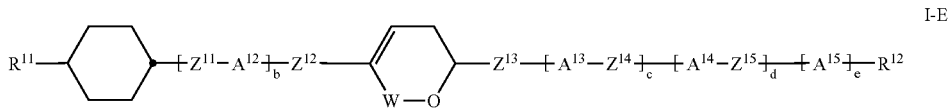

I-E where b, c, d, e, W, $R^{11}$, $R^{12}$, $Z^{11}$, $Z^{12}$, $Z^{13}$, $Z^{14}$, $Z^{15}$, $A^{12}$, $A^{13}$, $A^{14}$ and $A^{15}$ are as defined for the formula I above. Preferred sub-groups of compounds of the formula I-E are formed here by compounds of the formula I-EA where W is —C(=O)— and in particular by compounds of the formula I-EB where W is —CH$_2$—.

Particularly preferred compounds of the formula I-EB here are compounds of the formulae I-EBA and I-EBB; very particular preference is given to compounds of the formula I-EBC:

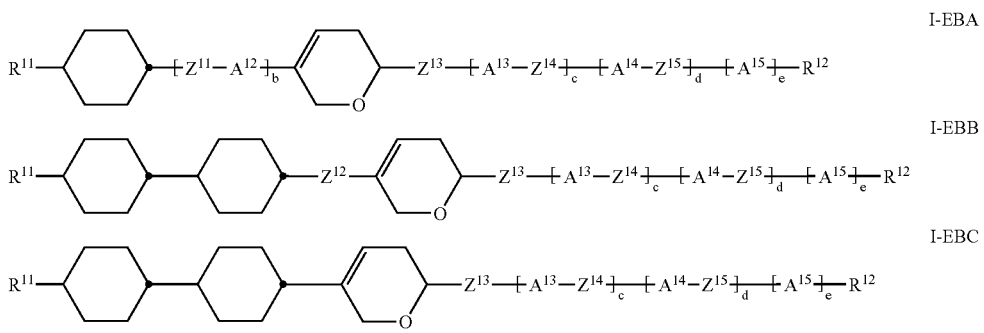

I-EBA

I-EBB

I-EBC where b, c, d, e, $R^{11}$, $R^{12}$, $Z^{11}$, $Z^{12}$, $Z^{13}$, $Z^{14}$, $Z^{15}$, $A^{12}$, $A^{13}$, $A^{14}$ and $A^{15}$ are as defined for the formula I above. It is preferred here for $Z^{13}$ to be a single bond or —CF$_2$O—, c and d both simultaneously to be zero and $A^{15}$ to be a 1,4-phenylene ring which is optionally mono- or polysubstituted by fluorine.

In addition, it is also preferred for $Z^{13}$ in the formula I to be a single bond (formula I-F) or to be a carboxyl function (formula I-G) or a difluorooxymethylene bridge (formula I-H):

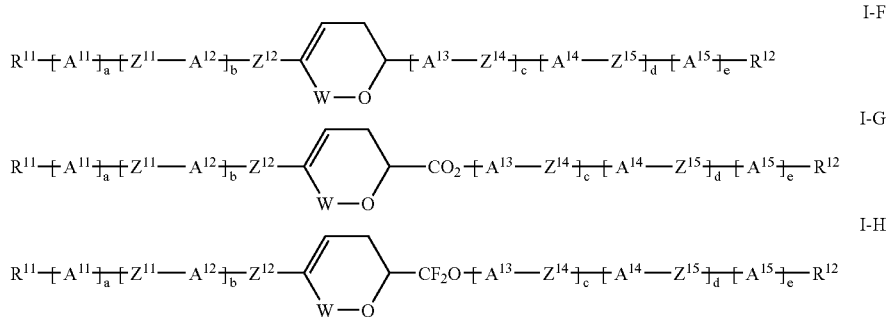

where a, b, c, d, e, W, $R^{11}$, $R^{12}$, $Z^{11}$, $Z^{12}$, $Z^{14}$, $Z^{15}$, $A^{11}$, $A^{12}$, $A^{13}$, $A^{14}$ and $A^{15}$ are as defined for the formulae I, I-C, I-D and I-E above. Preferred sub-groups of compounds of the formulae I-F, I-G and I-H are formed here by compounds of the formulae I-FA, I-GA and I-HA where W is —C(=O)— and in particular by compounds of the formulae I-FB, I-GB and I-HB where W is —CH$_2$—. It is particularly preferred here for $Z^{12}$ to be a single bond. If a and b are both simultaneously zero, $R^{11}$ is preferably an alkanyl radical having from 1 to seven carbon atoms. If a is 1, $A^{11}$ is preferably a 1,4-cyclohexylene ring. If b is 1, $Z^{11}$ is preferably a single bond and $A^{12}$ is likewise a 1,4-cyclohexylene ring.

The compounds of the formula I according to the invention furthermore preferably contain a ring $A^{15}$, this ring particularly preferably being a 1,4-phenylene ring which is optionally substituted by fluorine in the 3- and/or 5-position (formula I-J):

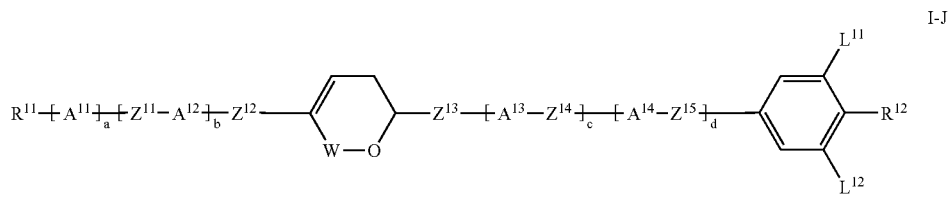

where a, b, c, d, W, $R^{11}$, $R^{12}$, $Z^{11}$, $Z^{12}$, $Z^{13}$, $Z^{14}$, $Z^{15}$, $A^{11}$, $A^{12}$, $A^{13}$ and $A^{14}$ are as defined for the formulae I, I-C, I-D, I-E, I-F, I-G and I-H above, and $L^{11}$ and $L^{12}$, independently of one another, are H or F. Preferred sub-groups of compounds of the formula I-J are formed here by compounds of the formula I-JA where W is —C(=O)— and in particular by compounds of the formula I-JB where W is —CH$_2$—. $R^{12}$ here is particularly preferably halogen, in particular fluorine, or an unbranched alkanyl or alkoxy radical having from 1 to 5 carbon atoms which is optionally mono- or polysubstituted by halogen, in particular fluorine.

A further group of preferred compounds of the formula I according to the invention is formed by compounds in which $A^{15}$-$R^{12}$ is

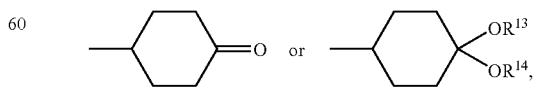

where $R^{13}$ and $R^{14}$ are as defined for the formula I above, and which are represented by the formulae I-K (cyclohexanones) and I-L (ketals):

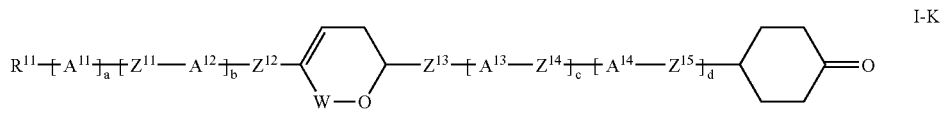

I-K

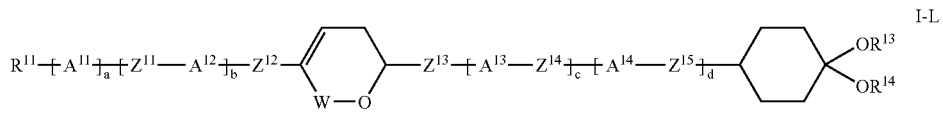

I-L where a, b, c, d, W, $R^{11}$, $Z^{11}$, $Z^{12}$, $Z^{13}$, $Z^{14}$, $Z^{15}$, $A^{11}$, $A^{12}$, $A^{13}$ and $A^{14}$ are as defined for the formula I above, c and d in the formulae I-K and I-L are particularly preferably simultaneously zero.

A further group of preferred compounds of the formula I according to the invention is formed by compounds in which c is 1; $Z^{14}$ is a single bond, —C(O)—O— or —CF$_2$O—; $A^{13}$ is

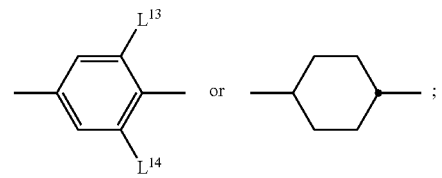

and $L^{13}$ and $L^{14}$, independently of one another, are H or F. These compounds are represented by the formulae I-M, I-N, I-O, I-P, I-Q and I-R:

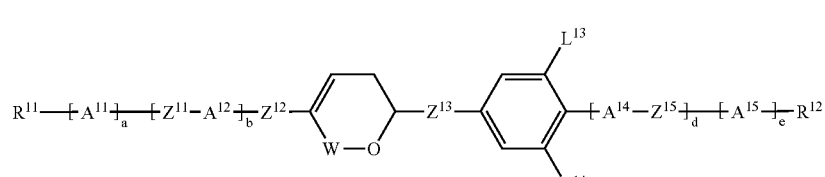

I-M

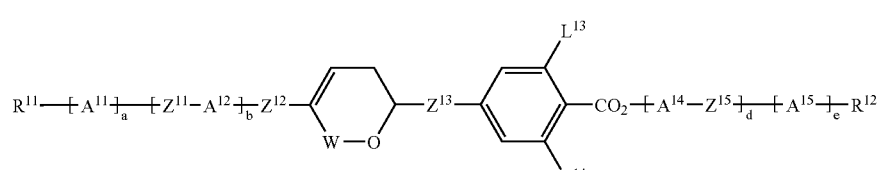

I-N

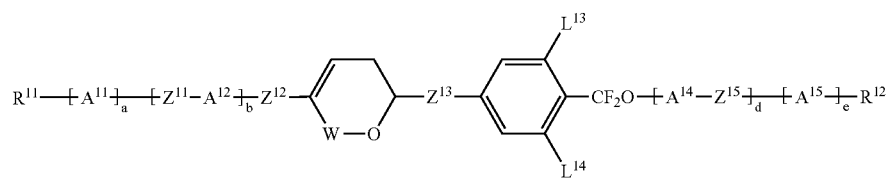

I-O

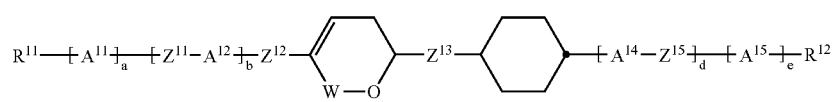

I-P

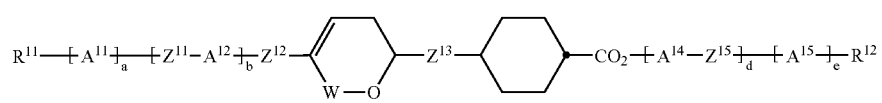

I-Q

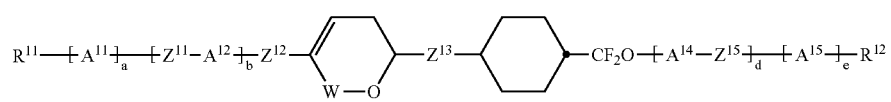

I-R where a, b, d, e, $R^{11}$, $R^{12}$, $Z^{11}$, $Z^{12}$, $Z^{13}$, $A^{11}$, $A^{12}$, $A^{14}$ and $A^{15}$ are as defined for the formula I above. Preferred sub-groups of compounds of the formulae I-M, I-N, I-O, I-P, I-Q and I-R are formed here by compounds of the formulae I-MA, I-NA, I-OA, I-PA, I-QA and I-RA where W is —C(=O)— and in particular by compounds of the formulae I-MB, I-NB, I-OB, I-PB, I-QB and I-RB where W is —CH$_2$—. It is particularly preferred here for $Z^{13}$ to be a single bond, d to be zero and e to be 1, and $A^{15}$ to be a 1,4-phenylene ring which is optionally mono- or polysubstituted by fluorine.

A further group of preferred compounds according to the invention is formed by compounds of the formulae I-S and I-T, i.e. compounds of the formula I in which d is 1; $Z^{15}$ is —CF$_2$O—; $A^{14}$ is

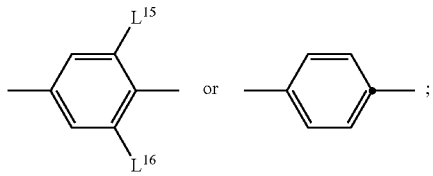

and $L^{15}$ and $L^{16}$, independently of one another, are H or F:

For the compounds of the formula I-T where c=1, it is preferred for $Z^{14}$ to be a single bond and $A^{13}$ to be

Preferred sub-groups of compounds of the formulae I-S and I-T are formed here by compounds of the formulae I-SA and I-TA where W is —C(=O)— and in particular by compounds of the formulae I-SB and I-TB where W is —CH$_2$—.

Very particularly preferred compounds of the formula I-CB according to the invention are those of the formulae I-CBI and I-CBII (which, inter alia, also represent embodiments of compounds of the formulae I-F, I-J, I-P, I-Q, I-R and I-T (I-CBI) and I-F, I-J, I-M, I-N and I-O (I-CBII) respectively):

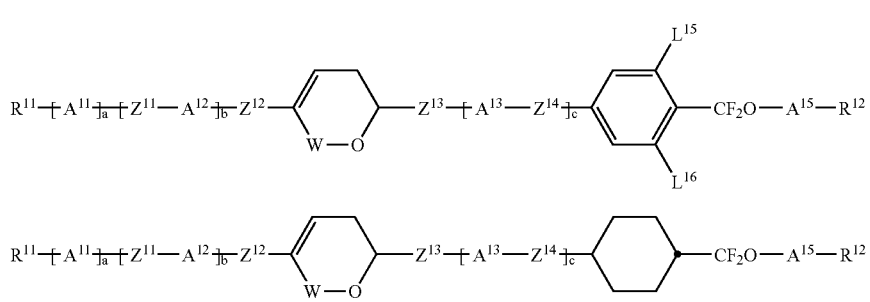

where a, b, c, $R^{11}$, $R^{12}$, $Z^{11}$, $Z^{12}$, $Z^{13}$, $Z^{14}$, $A^{11}$, $A^{12}$, $A^{13}$ and $A^{15}$ are as defined for the formula I above. It is particularly preferred for $A^{15}$ in the formulae I-S and I-T to be

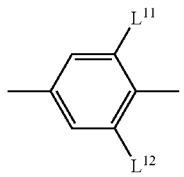

and for $Z^{13}$ to be a single bond. It is furthermore preferred for the compounds of the formula I-S where c=1 for $Z^{14}$ to be a single bond and for $A^{13}$ to be

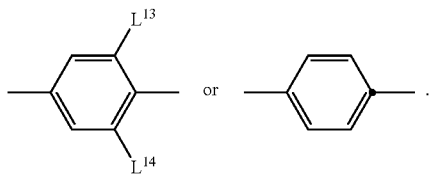

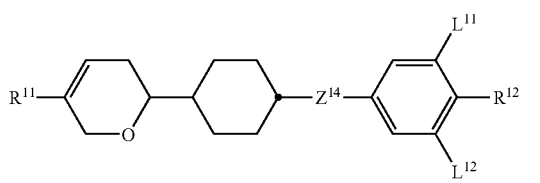

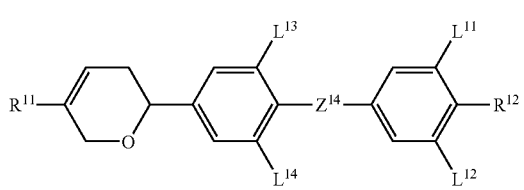

in which $L^{13}$ and $L^{14}$, independently of one another, are H or F, and $R^{11}$, $R^{12}$, $L^{11}$, $L^{12}$ and $Z^{14}$ are as defined for the formula I above, where $R^{11}$ is preferably a straight-chain alkenyl (C$_n$H$_{2n-1}$) or particularly preferably alkanyl (C$_n$H$_{2n+1}$) radical having from 1 to 7 carbon atoms, in particular methyl, while $R^{12}$ is preferably halogen, in particular fluorine, or an unbranched alkanyl or alkoxy radical having from 1 to 5 carbon atoms which is optionally mono- or polysubstituted by halogen, in particular fluorine, and $Z^{14}$ is preferably a single bond, a carboxyl group or a difluorooxymethylene bridge.

Illustrative compounds of the formulae I-CBI and I-CBII are shown by the formulae I-CBIa, I-CBIb, I-CBIc, I-CBIIa, I-CBIIb and I-CBIIc, where the preferred meaning of $R^{12}$, $L^{11}$, $L^{12}$, $L^{13}$ and $L^{14}$ as well as n is indicated in Tables 1 and 2 below:

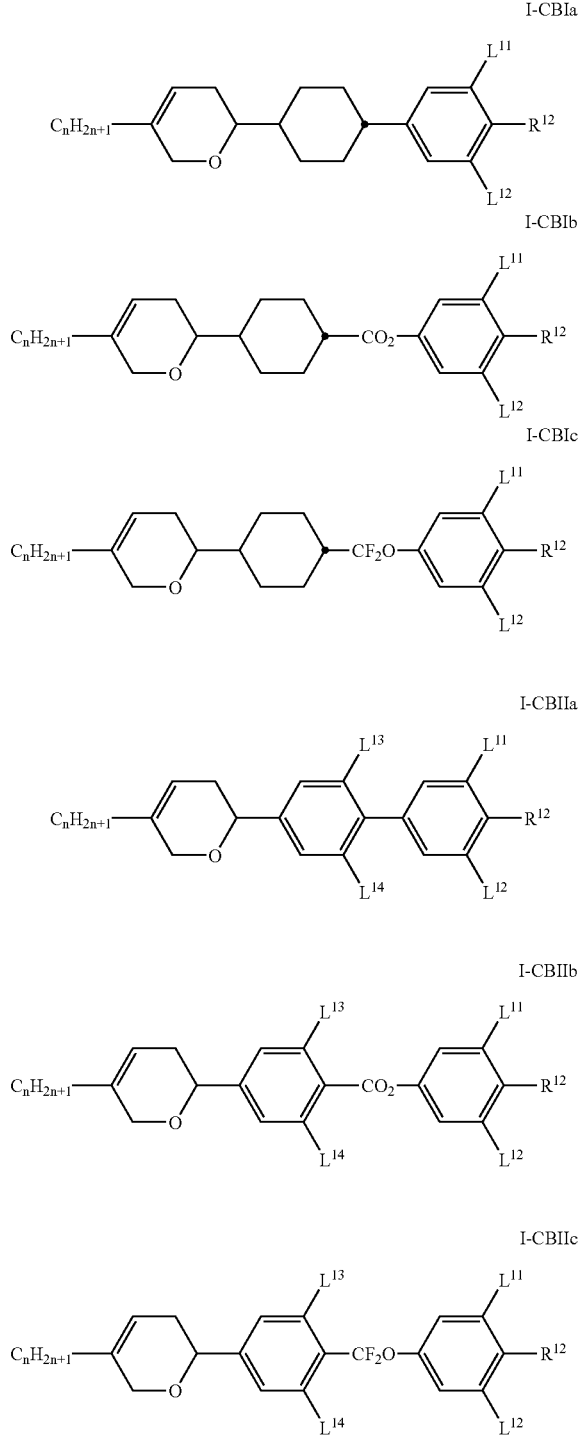

A further group of very particularly preferred compounds of the formula I-CB are those of the formula I-CBIII:

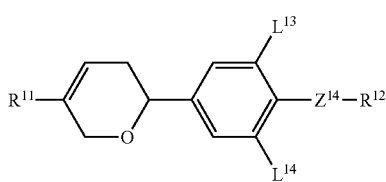

where $R^{11}$ and $Z^{14}$—$R^{12}$ are as defined for the formula I above, and $L^{13}$ and $L^{14}$, independently of one another, are H or F. $Z^{14}$—$R^{12}$ here is preferably formed by substituents which simplify further functionalization or derivatization with formation of other compounds of the formula I according to the invention, for example through the introduction of further ring systems $A^{14}$ and/or $A^{15}$. $Z^{14}$—$R^{12}$ is particularly preferably alkoxy or O-aralkyl, in particular O-t-butyl, O-benzyl or O-(p-nitrobenzyl); $CO_2H$; $CO_2$-alkanyl or $CO_2$-aralkyl, in particular $CO_2$-t-butyl or $CO_2$-benzyl; and (single bond)halogen, in particular —Br. $R^{11}$ is preferably a straight-chain alkenyl or alkanyl radical having up to 7 carbon atoms.

Illustrative compounds of the formula I-CBIII are those of the formulae I-CBIIIa, I-CBIIIb and I-CBIIIc:

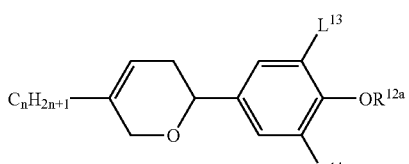

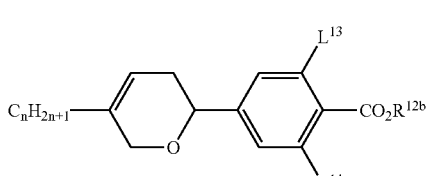

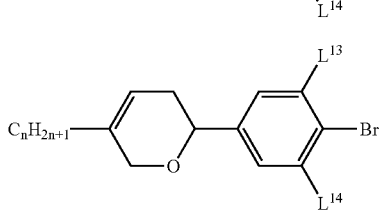

in which $L^{13}$ and $L^{14}$, independently of one another, are H or F, $R^{12a}$ is t-butyl, benzyl or p-nitrobenzyl, $R^{12b}$ is H, alkanyl having from 1 to 5 carbon atoms, or aralkyl, in particular H, t-butyl or benzyl, while $C_nH_{2n+1}$ is a straight-chain alkanyl radical where n=1, 2, 3, 4, 5, 6 or 7.

Very particularly preferred compounds of the formula I-DBA according to the invention are those of the formulae I-DBAI, I-DBAII and I-DBAIII:

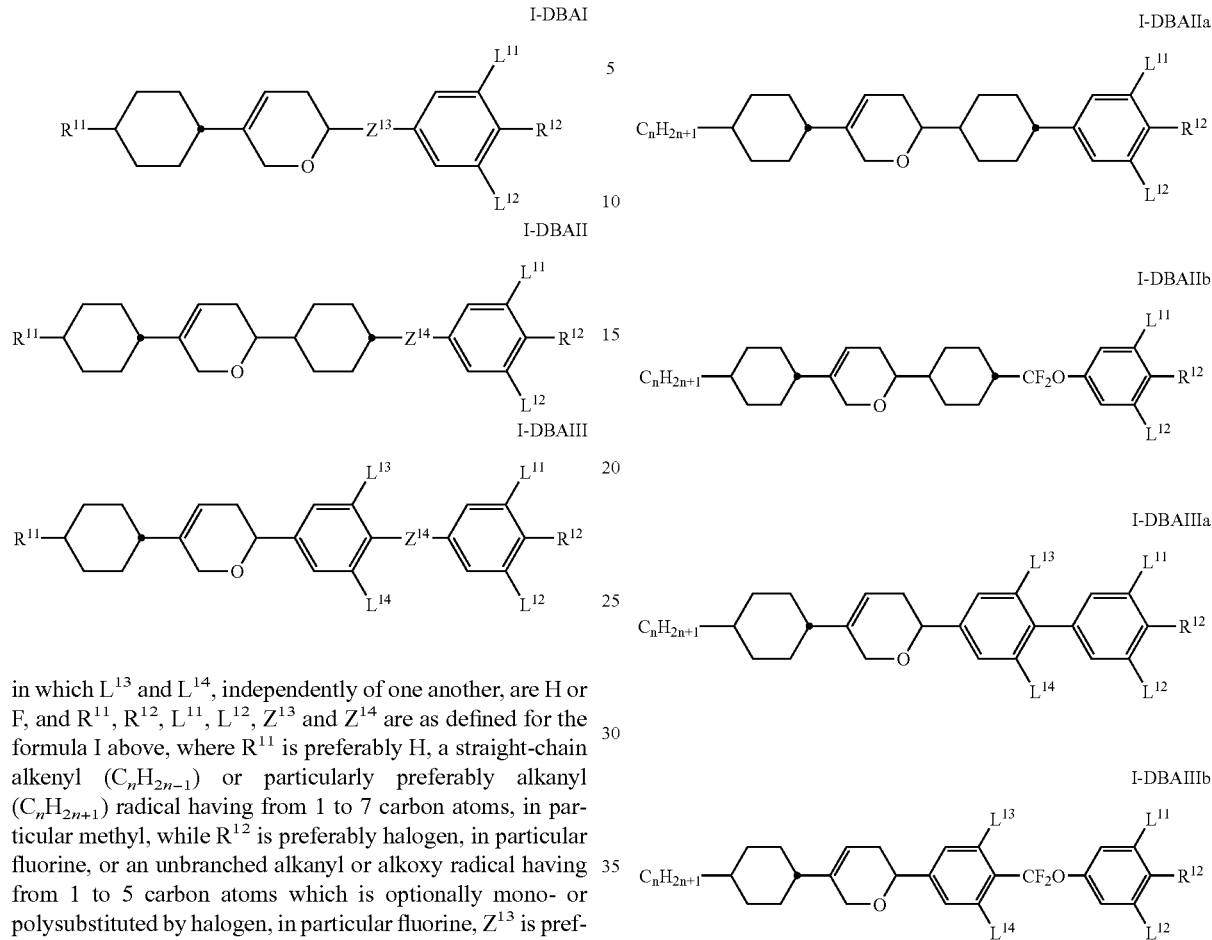

in which $L^{13}$ and $L^{14}$, independently of one another, are H or F, and $R^{11}$, $R^{12}$, $L^{11}$, $L^{12}$, $Z^{13}$ and $Z^{14}$ are as defined for the formula I above, where $R^{11}$ is preferably H, a straight-chain alkenyl ($C_nH_{2n-1}$) or particularly preferably alkanyl ($C_nH_{2n+1}$) radical having from 1 to 7 carbon atoms, in particular methyl, while $R^{12}$ is preferably halogen, in particular fluorine, or an unbranched alkanyl or alkoxy radical having from 1 to 5 carbon atoms which is optionally mono- or polysubstituted by halogen, in particular fluorine, $Z^{13}$ is preferably a single bond or $CF_2O$, and $Z^{14}$ is preferably a single bond, a carboxyl group or a difluorooxymethylene bridge.

Illustrative compounds of the formulae I-DBAI, I-DBAII and I-DBAIII are shown by the formulae I-DBAIa, I-DBAIb, I-DBAIIa, I-DBAIIb, I-DBAIIIa and I-DBAIIIb, where the preferred meaning of $R^{12}$, $L^{11}$, $L^{12}$, $L^{13}$ and $L^{14}$ as well as n (n is 0, 1, 2, 3, 4, 5, 6 or 7) is indicated in Tables 3 and 4 below:

Very particularly preferred compounds of the formula I-EBC according to the invention are those of the formula I-EBCI:

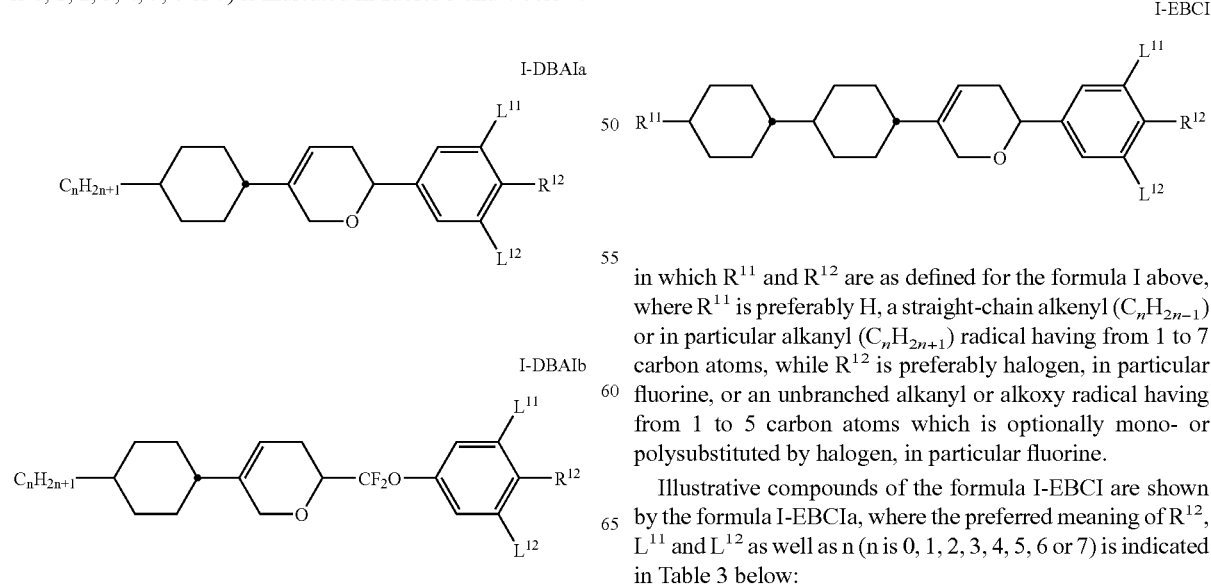

in which $R^{11}$ and $R^{12}$ are as defined for the formula I above, where $R^{11}$ is preferably H, a straight-chain alkenyl ($C_nH_{2n-1}$) or in particular alkanyl ($C_nH_{2n+1}$) radical having from 1 to 7 carbon atoms, while $R^{12}$ is preferably halogen, in particular fluorine, or an unbranched alkanyl or alkoxy radical having from 1 to 5 carbon atoms which is optionally mono- or polysubstituted by halogen, in particular fluorine.

Illustrative compounds of the formula I-EBCI are shown by the formula I-EBCIa, where the preferred meaning of $R^{12}$, $L^{11}$ and $L^{12}$ as well as n (n is 0, 1, 2, 3, 4, 5, 6 or 7) is indicated in Table 3 below:

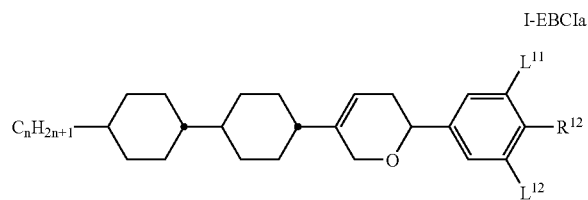
I-EBCIa

Very particularly preferred compounds of the formula I-GB according to the invention are, besides compounds of the formula I-GBI, also those of the formulae I-GBII and I-GBIII (which, inter alia, also represent embodiments of compounds of the formula I-J):

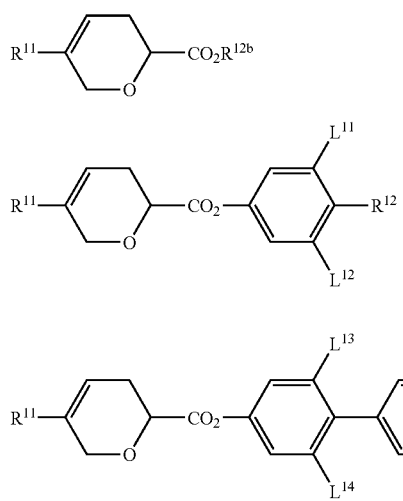
I-GBI

I-GBII

I-GBIII in which $L^{13}$ and $L^{14}$, independently of one another, are H or F, $R^{12b}$ is as defined for $R^{12}$ for the formula I above, and $R^{11}$, $R^{12}$, $L^{11}$ and $L^{12}$ are as defined for the formula I above, where $R^{11}$ is preferably a straight-chain alkenyl ($C_nH_{2n-1}$) or in particular alkanyl ($C_nH_{2+1}$) radical having from 1 to 7 carbon atoms, while $R^{12}$ for I-GBII and I-GBIII is preferably halogen, in particular fluorine, or an unbranched alkanyl or alkoxy radical having from 1 to 5 carbon atoms which is optionally mono- or polysubstituted by halogen, in particular fluorine; for I-GBI, $R^{12b}$ is preferably H, alkanyl having from 1 to 5 carbon atoms or aralkyl, in particular H, tert-butyl or benzyl.

Illustrative compounds of the formula I-GBI are shown by the formula I-GBIa, where the preferred meaning of $R^{12b}$ and n (n is 1, 2, 3, 4, 5, 6 or 7) is indicated below in Table 5. Illustrative compounds of the formulae I-GBII and I-GBIII are shown by the formulae I-GBIIa and I-GBIIIa, where the preferred meaning of $R^{12}$, $L^{11}$, $L^{12}$, $L^{13}$ and $L^{14}$ as well as n (n is 1, 2, 3, 4, 5, 6 or 7) is indicated in Tables 1 and 2 below:

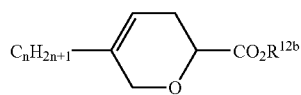
I-GBIa

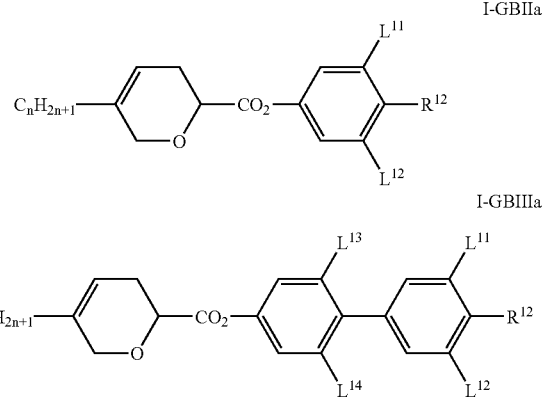
I-GBIIa

I-GBIIIa

Very particular preferred compounds of the formula I-HB according to the invention are those are of the formulae I-HBI and I-HBII (where the compounds of the formulae I-HBI and I-HBII are, inter alia, also embodiments of compounds of the formula I-J):

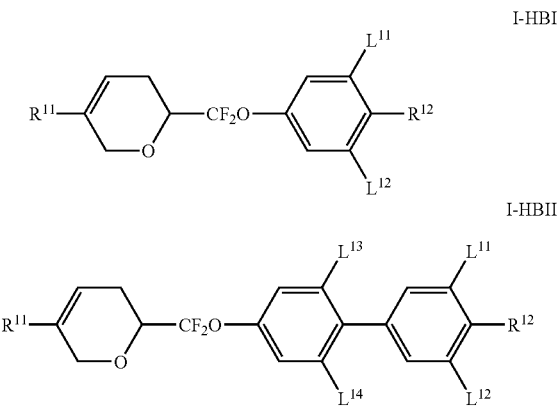
I-HBI

I-HBII in which $L^{13}$ and $L^{14}$, independently of one another, are H or F, and $R^{11}$, $R^{12}$, $L^{11}$ and $L^{12}$ are as defined for the formula I above, where $R^{11}$ is preferably a straight-chain alkenyl ($C_nH_{2n-1}$) or in particular alkanyl ($C_nH_{2+1}$) radical having from 1 to 7 carbon atoms, while $R^{12}$ is preferably halogen, in particular fluorine, or an unbranched alkanyl or alkoxy radical having from 1 to 5 carbon atoms which is optionally mono- or polysubstituted by halogen, in particular fluorine.

Illustrative compounds of the formulae I-HBI and I-HBII are shown by the formulae I-HBIa and I-HBIIa, where the preferred meaning of $R^{12}$, $L^{11}$, $L^{12}$, $L^{13}$ and $L^{14}$ as well as n (n is 1, 2, 3, 4, 5, 6 or 7) is indicated in Tables 1 and 2 below:

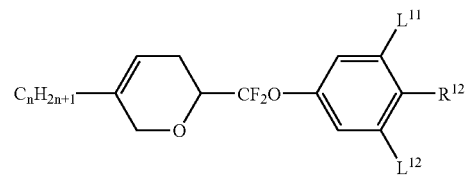
I-HBIa

-continued

I-HBIIa

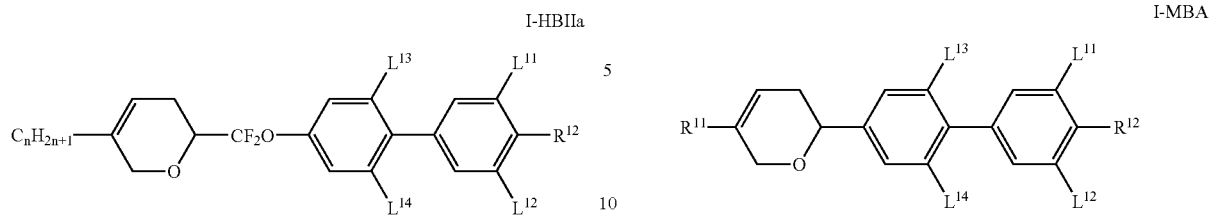

Very particularly preferred compounds of the formula I-KB according to the invention are those of the formulae I-KBI and I-KBII:

I-KBI

I-KBII

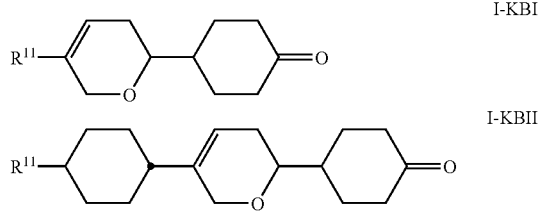

in which $R^{11}$ is as defined for the formula I above and is preferably a straight-chain alkenyl ($C_nH_{2n-1}$) or in particular alkanyl ($C_nH_{2n+1}$) radical having from 1 to 7 carbon atoms, in the case of I-KBII also H. Illustrative compounds of the formulae I-KBI and I-KBII are those in which $R^{11}$ is a straight-chain alkanyl radical $C_nH_{2n+1}$ where n=1, 2, 3, 4, 5, 6 or 7.

Very particularly preferred compounds of the formula I-LB according to the invention are those of the formulae I-LBI and I-LBII:

I-LBI

I-LBII

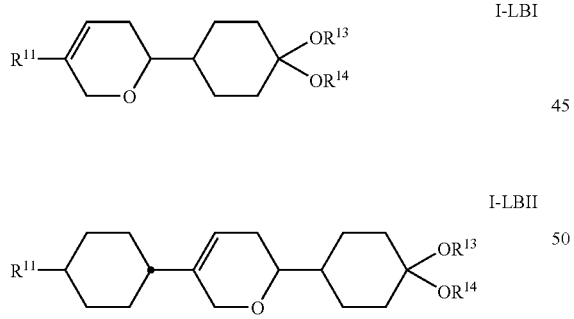

in which $R^{11}$ is as defined for the formula I above and is preferably a straight-chain alkenyl ($C_nH_{2n-1}$) or in particular alkanyl ($C_nH_{2n+1}$) radical having from 1 to 7 carbon atoms, in the case of I-LBII also H. $R^{13}$ and $R^{14}$ are likewise as defined for the formula I above and are preferably both methyl or together —$(CH_2)_3$—. Illustrative compounds of the formulae I-LBI and I-LBII are those in which $R^{11}$ is a straight-chain alkanyl radical $C_nH_{2n+1}$ where n=1, 2, 3, 4, 5, 6 or 7.

Very particularly preferred compounds of the formula I-MB according to the invention are those of the formulae I-MBA and I-MBB:

I-MBA

I-MBB in which $L^{13}$ and $L^{14}$, independently of one another, are H or F, and $R^{11}$, $R^{12}$, $L^{11}$ and $L^{12}$ are as defined for the formula I above, where $R^{11}$ is preferably a straight-chain alkenyl ($C_nH_{2n-1}$) or in particular alkanyl ($C_nH_{2n+1}$) radical having from 1 to 7 carbon atoms, in the case of I-MBB also H, while $R^{12}$ is preferably halogen, in particular fluorine, or an unbranched alkanyl or alkoxy radical having from 1 to 5 carbon atoms which is optionally mono- or polysubstituted by halogen, in particular fluorine.

Illustrative compounds of the formula I-MBA are compounds which are also represented by the formula I-CBIIa above, and illustrative compounds of the formula I-MBB are compounds which are also represented by the formula I-DBAIIIa above.

Very particularly preferred compounds of the formula I-NB according to the invention are those of the formulae I-NBA, I-NBB, I-NBC and I-NBD:

I-NBA

I-NBB

I-NBC

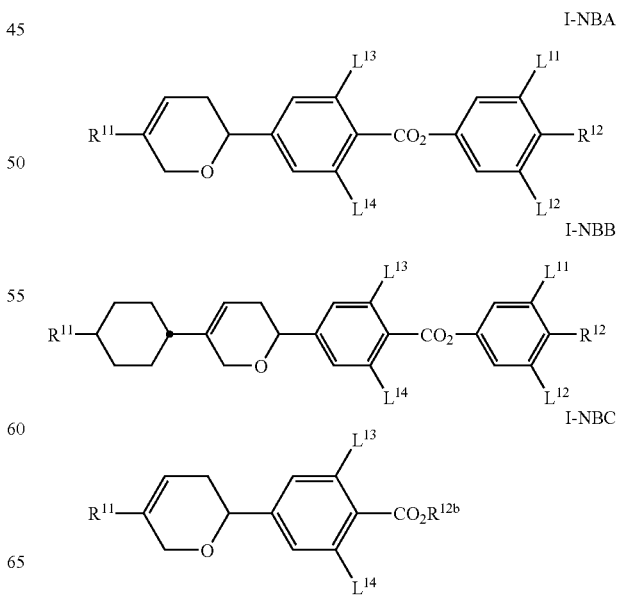

-continued

I-NBD

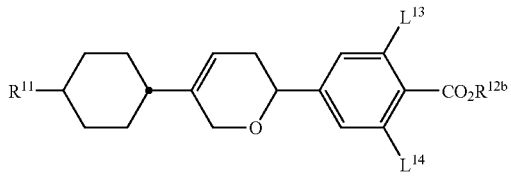

in which $L^{13}$ and $L^{14}$, independently of one another, are H or F, and $R^{11}$, $R^{12}$, $L^{11}$ and $L^{12}$ are as defined for the formula I above, where $R^{11}$ is preferably a straight-chain alkenyl $(C_nH_{2n-1})$ or in particular alkanyl $(C_nH_{2n+1})$ radical having from 1 to 7 carbon atoms, in the case of I-NBB and I-NBD also H, while $R^{12}$ is preferably halogen, in particular fluorine, or an unbranched alkanyl or alkoxy radical having from 1 to 5 carbon atoms which is optionally mono- or polysubstituted by halogen, in particular fluorine. $R^{12b}$ has the same meaning as for the formula I-CBIIIb or I-GBIa above.

Illustrative compounds of the formula I-NBA are compounds which are also represented by the formula I-CBIIb above, and illustrative compounds of the formula I-NBC are compounds which are also represented by the formula I-CBIIb above. Illustrative compounds of the formula I-NBB are those which are shown by the formula I-NBBIa, where the meaning of $R^{12}$, $L^{11}$, $L^{12}$, $L^{13}$ and $L^{14}$ as well as n (n is 0, 1, 2, 3, 4, 5, 6 or 7) is indicated in Table 4 below:

I-NBBIa

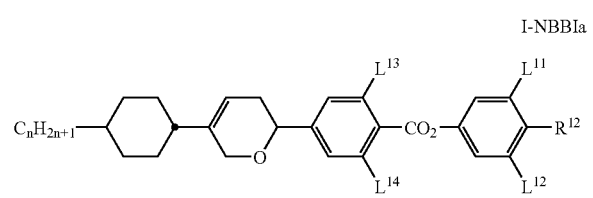

Very particularly preferred compounds of the formula I-OB according to the invention are those of the formulae I-OBA and I-OBB:

I-OBA

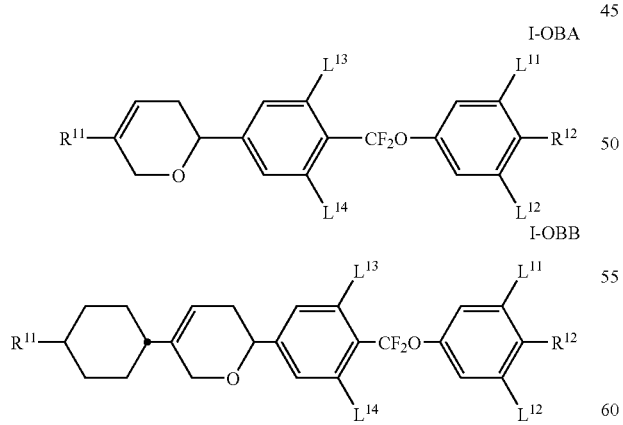

I-OBB in which $L^{13}$ and $L^{14}$, independently of one another, are H or F, and $R^{11}$, $R^{12}$, $L^{11}$ and $L^{12}$ are as defined for the formula I above, where $R^{11}$ is preferably a straight-chain alkenyl $(C_nH_{2n-1})$ or in particular alkanyl $(C_nH_{2n+1})$ radical having from 1 to 7 carbon atoms, in the case of I-OBB also H, while $R^{12}$ is preferably halogen, in particular fluorine, or an unbranched alkanyl or alkoxy radical having from 1 to 5 carbon atoms which is optionally mono- or polysubstituted by halogen, in particular fluorine.

Illustrative compounds of the formula I-OBA are compounds which are also represented by the formula I-CBIIc above, and illustrative compounds of the formula I-OBB are compounds which are also represented by the formula I-DBAIIIb above.

Very particularly preferred compounds of the formula I-PB according to the invention are those of the formulae I-PBA and I-PBB:

I-PBA

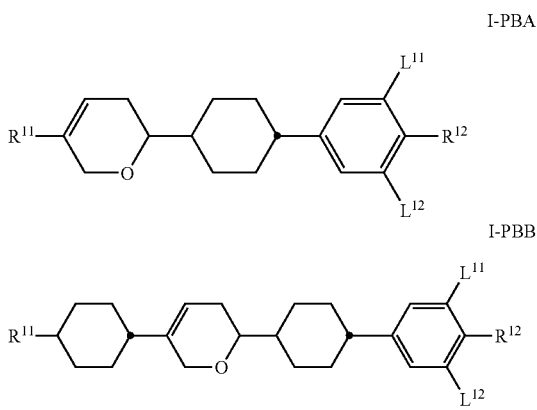

I-PBB in which $R^{11}$, $R^{12}$, $L^{11}$ and $L^{12}$ are as defined for the formula I above, where $R^{11}$ is preferably a straight-chain alkenyl $(C_nH_{2n-1})$ or in particular alkanyl $(C_nH_{2n+1})$ radical having from 1 to 7 carbon atoms, in the case of I-PBB also H, while $R^{12}$ is preferably halogen, in particular fluorine, or an unbranched alkanyl or alkoxy radical having from 1 to 5 carbon atoms which is optionally mono- or polysubstituted by halogen, in particular fluorine.

Illustrative compounds of the formula I-PBA are compounds which are also represented by the formula I-CBIa above, and illustrative compounds of the formula I-PBB are compounds which are also represented by the formula I-DBAIIa above.

Very particularly preferred compounds of the formula I-QB according to the invention are those of the formulae I-QBA, I-QBB and I-QBC:

I-QBA

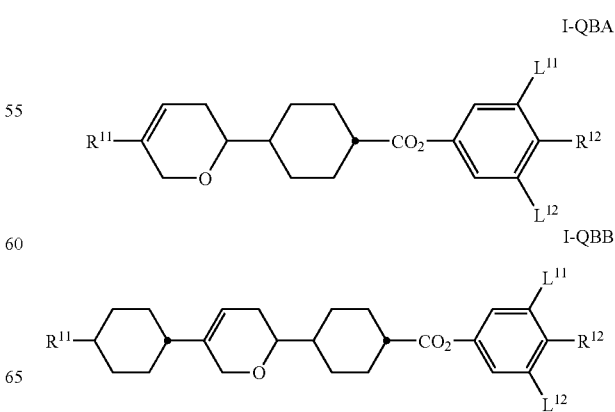

I-QBB

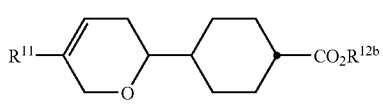
I-QBC in which $R^{11}$, $R^{12}$, $L^{11}$ and $L^{12}$ are as defined for the formula I above, where $R^{11}$ is preferably a straight-chain alkenyl ($C_nH_{2n-1}$) or in particular alkanyl ($C_nH_{2n+1}$) radical having from 1 to 7 carbon atoms, in the case of I-QBB also H, while $R^{12}$ is preferably halogen, in particular fluorine, or an unbranched alkanyl or alkoxy radical having from 1 to 5 carbon atoms which is optionally mono- or polysubstituted by halogen, in particular fluorine. $R^{12b}$ has the same meaning as for the formula I-CBIIIb above.

Illustrative compounds of the formula I-QBA are compounds which are also represented by the formula I-CBIb above. Illustrative compounds of the formula I-QBB are compounds which are shown by the formula I-QBBIa, where the meaning of $R^{12}$, $L^{11}$ and $L^{12}$ as well as n (n is 0, 1, 2, 3, 4, 5, 6 or 7) is indicated in Table 3 below:

I-QBBIa

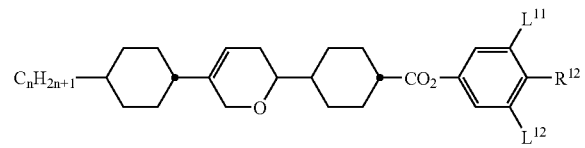

Very particularly preferred compounds of the formula I-RB according to the invention are those of the formulae I-RBA and I-RBB:

I-RBA

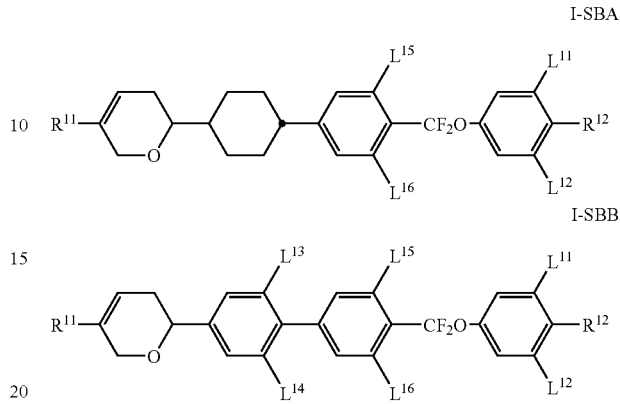

I-RBB in which $R^{11}$, $R^{12}$, $L^{11}$ and $L^{12}$ are as defined for the formula I above, where $R^{11}$ is preferably a straight-chain alkenyl ($C_nH_{2n-1}$) or in particular alkanyl ($C_nH_{2n+1}$) radical having from 1 to 7 carbon atoms, in the case of I-RBB also H, while $R^{12}$ is preferably halogen, in particular fluorine, or an unbranched alkanyl or alkoxy radical having from 1 to 5 carbon atoms which is optionally mono- or polysubstituted by halogen, in particular fluorine.

Illustrative compounds of the formula I-RBA are compounds which are also represented by the formula I-CBIc above, and illustrative compounds of the formula I-RBB are compounds which are also represented by the formula I-DBAIIb above.

Very particularly preferred compounds of the formula I-SB according to the invention are those of the formulae I-SBA and I-SBB:

I-SBA

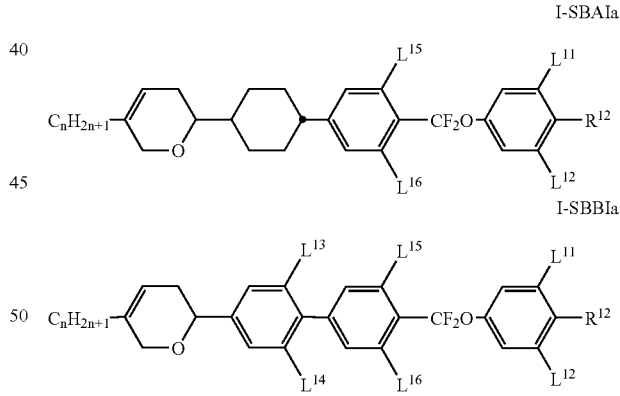

I-SBB in which $L^{13}$, $L^{14}$, $L^{15}$ and $L^{16}$, independently of one another, are H or F, and $R^{11}$, $R^{12}$, $L^{11}$ and $L^{12}$ are as defined for the formula I above, where $R^{11}$ is preferably a straight-chain alkenyl ($C_nH_{2n-1}$) or in particular alkanyl ($C_nH_{2n+1}$) radical having from 1 to 7 carbon atoms, while $R^{12}$ is preferably halogen, in particular fluorine, or an unbranched alkanyl or alkoxy radical having from 1 to 5 carbon atoms which is optionally mono- or polysubstituted by halogen, in particular fluorine.

Illustrative compounds of the formulae I-SBA and I-SBB are compounds which are shown by the formulae I-SBAIa and I-SBBIa respectively, where the meaning of $R^{12}$, $L^{11}$, $L^{12}$, $L^{13}$, $L^{14}$, $L^{15}$ and $L^{16}$ as well as n (n is 1, 2, 3, 4, 5, 6 or 7) is indicated in Tables 2 and 6 below:

I-SBAIa

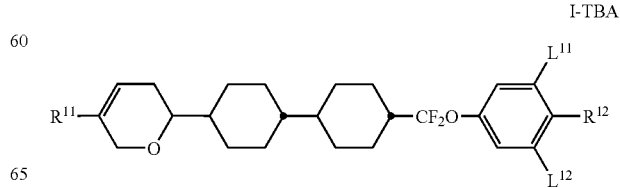

I-SBBIa

Very particularly preferred compounds of the formula I-TB according to the invention are those of the formula I-TBA:

I-TBA in which $R^{11}$, $R^{12}$, $L^{11}$ and $L^{12}$ are as defined for the formula I above, where $R^{11}$ is preferably a straight-chain alkenyl ($C_nH_{2n-1}$) or in particular alkanyl ($C_nH_{2n+1}$) radical having from 1 to 7 carbon atoms, while $R^{12}$ is preferably halogen, in particular fluorine, or an unbranched alkanyl or alkoxy radical having from 1 to 5 carbon atoms which is optionally mono- or polysubstituted by halogen, in particular fluorine.

Illustrative compounds of the formula I-TBA are compounds which are shown by the formula I-TBAIa, where the meaning of $R^{12}$, $L^{11}$ and $L^{12}$ as well as n (n is 1, 2, 3, 4, 5, 6 or 7) is indicated in Table 1 below:

TABLE 1

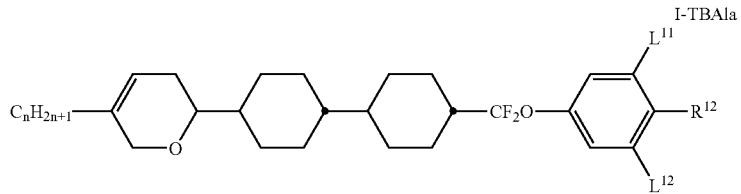

I-TBAIa

| Compound I-CBIa-/I-CBIb-/I-CBIc-/I-GBIIa-/I-HBIa-/I-TBAIa No. | n* | $R^{12}$ | $L^{11}$ | $L^{12}$ |
|---|---|---|---|---|
| -1 | 1 | F | H | H |
| -2 | 1 | F | F | H |
| -3 | 1 | F | F | F |
| -4 | 1 | $CF_3$ | H | H |
| -5 | 1 | $CF_3$ | F | H |
| -6 | 1 | $CF_3$ | F | F |
| -7 | 1 | $OCF_3$ | H | H |
| -8 | 1 | $OCF_3$ | F | H |
| -9 | 1 | $OCF_3$ | F | F |
| -10 | 1 | $OCHF_2$ | H | H |
| -11 | 1 | $OCHF_2$ | F | H |
| -12 | 1 | $OCHF_2$ | F | F |
| -13 | 1 | —CN | H | H |
| -14 | 1 | —CN | F | H |
| -15 | 1 | —CN | F | F |
| -16 | 2 | F | H | H |
| -17 | 2 | F | F | H |
| -18 | 2 | F | F | F |
| -19 | 2 | $CF_3$ | H | H |
| -20 | 2 | $CF_3$ | F | H |
| -21 | 2 | $CF_3$ | F | F |
| -22 | 2 | $OCF_3$ | H | H |
| -23 | 2 | $OCF_3$ | F | H |
| -24 | 2 | $OCF_3$ | F | F |
| -25 | 2 | $OCHF_2$ | H | H |
| -26 | 2 | $OCHF_2$ | F | H |
| -27 | 2 | $OCHF_2$ | F | F |
| -28 | 2 | —CN | H | H |
| -29 | 2 | —CN | F | H |
| -30 | 2 | —CN | F | F |
| -31 | 3 | F | H | H |
| -32 | 3 | F | F | H |
| -33 | 3 | F | F | F |
| -34 | 3 | $CF_3$ | H | H |
| -35 | 3 | $CF_3$ | F | H |
| -36 | 3 | $CF_3$ | F | F |
| -37 | 3 | $OCF_3$ | H | H |
| -38 | 3 | $OCF_3$ | F | H |
| -39 | 3 | $OCF_3$ | F | F |
| -40 | 3 | $OCHF_2$ | H | H |
| -41 | 3 | $OCHF_2$ | F | H |
| -42 | 3 | $OCHF_2$ | F | F |
| -43 | 3 | —CN | H | H |
| -44 | 3 | —CN | F | H |
| -45 | 3 | —CN | F | F |
| -46 | 4 | F | H | H |
| -47 | 4 | F | F | H |
| -48 | 4 | F | F | F |
| -49 | 4 | $CF_3$ | H | H |
| -50 | 4 | $CF_3$ | F | H |
| -51 | 4 | $CF_3$ | F | F |
| -52 | 4 | $OCF_3$ | H | H |
| -53 | 4 | $OCF_3$ | F | H |
| -54 | 4 | $OCF_3$ | F | F |
| -55 | 4 | $OCHF_2$ | H | H |
| -56 | 4 | $OCHF_2$ | F | H |
| -57 | 4 | $OCHF_2$ | F | F |

TABLE 1-continued

I-TBAIa structure: $C_nH_{2n+1}$—[tetrahydropyran]—[cyclohexyl]—[cyclohexyl]—$CF_2O$—[phenyl with $L^{11}$, $R^{12}$, $L^{12}$]

| Compound I-CBIa-/I-CBIb-/I-CBIc-/I-GBIIa-/I-HBIa-/I-TBAIa No. | n* | $R^{12}$ | $L^{11}$ | $L^{12}$ |
|---|---|---|---|---|
| -58 | 4 | —CN | H | H |
| -59 | 4 | —CN | F | H |
| -60 | 4 | —CN | F | F |
| -61 | 5 | F | H | H |
| -62 | 5 | F | F | H |
| -63 | 5 | F | F | F |
| -64 | 5 | $CF_3$ | H | H |
| -65 | 5 | $CF_3$ | F | H |
| -66 | 5 | $CF_3$ | F | F |
| -67 | 5 | $OCF_3$ | H | H |
| -68 | 5 | $OCF_3$ | F | H |
| -69 | 5 | $OCF_3$ | F | F |
| -70 | 5 | $OCHF_2$ | H | H |
| -71 | 5 | $OCHF_2$ | F | H |
| -72 | 5 | $OCHF_2$ | F | F |
| -73 | 5 | —CN | H | H |
| -74 | 5 | —CN | F | H |
| -75 | 5 | —CN | F | F |

*: The radical $C_nH_{2n+1}$ is unbranched.

TABLE 2

| Compound I-CBIIa-/I-CBIIb-/I-CBIIc-/I-GBIIIa-/I-HBIIa-/I-SBAIa No. | n* | $R^{12}$ | $L^{11}$ | $L^{12}$ | $L^{13}$** | $L^{14}$*** |
|---|---|---|---|---|---|---|
| -1 | 1 | F | H | H | H | H |
| -2 | 1 | F | F | H | H | H |
| -3 | 1 | F | F | F | H | H |
| -4 | 1 | F | F | F | F | H |
| -5 | 1 | F | F | F | F | F |
| -6 | 1 | F | F | H | F | H |
| -7 | 1 | F | F | H | F | F |
| -8 | 1 | $CF_3$ | H | H | H | H |
| -9 | 1 | $CF_3$ | F | H | H | H |
| -10 | 1 | $CF_3$ | F | F | H | H |
| -11 | 1 | $CF_3$ | F | F | F | H |
| -12 | 1 | $CF_3$ | F | F | F | F |
| -13 | 1 | $CF_3$ | F | H | F | H |
| -14 | 1 | $CF_3$ | F | H | F | F |
| -15 | 1 | $OCF_3$ | H | H | H | H |
| -16 | 1 | $OCF_3$ | F | H | H | H |
| -17 | 1 | $OCF_3$ | F | F | H | H |
| -18 | 1 | $OCF_3$ | F | F | F | H |
| -19 | 1 | $OCF_3$ | F | F | F | F |
| -20 | 1 | $OCF_3$ | F | H | F | H |
| -21 | 1 | $OCF_3$ | F | H | F | F |
| -22 | 1 | $OCHF_2$ | H | H | H | H |
| -23 | 1 | $OCHF_2$ | F | H | H | H |
| -24 | 1 | $OCHF_2$ | F | F | H | H |
| -25 | 1 | $OCHF_2$ | F | F | F | H |
| -26 | 1 | $OCHF_2$ | F | F | F | F |
| -27 | 1 | $OCHF_2$ | F | H | F | H |
| -28 | 1 | $OCHF_2$ | F | H | F | F |
| -29 | 1 | —CN | H | H | H | H |
| -30 | 1 | —CN | F | H | H | H |
| -31 | 1 | —CN | F | F | H | H |
| -32 | 1 | —CN | F | F | F | H |
| -33 | 1 | —CN | F | F | F | F |
| -34 | 1 | —CN | F | H | F | H |
| -35 | 1 | —CN | F | H | F | F |
| -36 | 2 | F | H | H | H | H |
| -37 | 2 | F | F | H | H | H |
| -38 | 2 | F | F | F | H | H |
| -39 | 2 | F | F | F | F | H |
| -40 | 2 | F | F | F | F | F |
| -41 | 2 | F | F | H | F | H |
| -42 | 2 | F | F | H | F | F |
| -43 | 2 | $CF_3$ | H | H | H | H |
| -44 | 2 | $CF_3$ | F | H | H | H |
| -45 | 2 | $CF_3$ | F | F | H | H |
| -46 | 2 | $CF_3$ | F | F | F | H |
| -47 | 2 | $CF_3$ | F | F | F | F |
| -48 | 2 | $CF_3$ | F | H | F | H |
| -49 | 2 | $CF_3$ | F | H | F | F |
| -50 | 2 | $OCF_3$ | H | H | H | H |
| -51 | 2 | $OCF_3$ | F | H | H | H |
| -52 | 2 | $OCF_3$ | F | F | H | H |
| -53 | 2 | $OCF_3$ | F | F | F | H |
| -54 | 2 | $OCF_3$ | F | F | F | F |
| -55 | 2 | $OCF_3$ | F | H | F | H |
| -56 | 2 | $OCF_3$ | F | H | F | F |
| -57 | 2 | $OCHF_2$ | H | H | H | H |
| -58 | 2 | $OCHF_2$ | F | H | H | H |
| -59 | 2 | $OCHF_2$ | F | F | H | H |
| -60 | 2 | $OCHF_2$ | F | F | F | H |
| -61 | 2 | $OCHF_2$ | F | F | F | F |
| -62 | 2 | $OCHF_2$ | F | H | F | H |
| -63 | 2 | $OCHF_2$ | F | H | F | F |
| -64 | 2 | —CN | H | H | H | H |
| -65 | 2 | —CN | F | H | H | H |
| -66 | 2 | —CN | F | F | H | H |
| -67 | 2 | —CN | F | F | F | H |
| -68 | 2 | —CN | F | F | F | F |
| -69 | 2 | —CN | F | H | F | H |
| -70 | 2 | —CN | F | H | F | F |
| -71 | 3 | F | H | H | H | H |
| -72 | 3 | F | F | H | H | H |

TABLE 2-continued

| Compound I-CBIIa-/I-CBIIb-/I-CBIIc-/I-GBIIIa-/I-HBIIa-/I-SBAIa No. | n* | R¹² | L¹¹ | L¹² | L¹³** | L¹⁴*** |
|---|---|---|---|---|---|---|
| −73 | 3 | F | F | F | H | H |
| −74 | 3 | F | F | F | F | H |
| −75 | 3 | F | F | F | F | F |
| −76 | 3 | F | F | H | F | H |
| −77 | 3 | F | F | H | F | F |
| −78 | 3 | CF₃ | H | H | H | H |
| −79 | 3 | CF₃ | F | H | H | H |
| −80 | 3 | CF₃ | F | F | H | H |
| −81 | 3 | CF₃ | F | F | F | H |
| −82 | 3 | CF₃ | F | F | F | F |
| −83 | 3 | CF₃ | F | H | F | H |
| −84 | 3 | CF₃ | F | H | F | F |
| −85 | 3 | OCF₃ | H | H | H | H |
| −86 | 3 | OCF₃ | F | H | H | H |
| −87 | 3 | OCF₃ | F | F | H | H |
| −88 | 3 | OCF₃ | F | F | F | H |
| −89 | 3 | OCF₃ | F | F | F | F |
| −90 | 3 | OCF₃ | F | H | F | H |
| −91 | 3 | OCF₃ | F | H | F | F |
| −92 | 3 | OCHF₂ | H | H | H | H |
| −93 | 3 | OCHF₂ | F | H | H | H |
| −94 | 3 | OCHF₂ | F | F | H | H |
| −95 | 3 | OCHF₂ | F | F | F | H |
| −96 | 3 | OCHF₂ | F | F | F | F |
| −97 | 3 | OCHF₂ | F | H | F | H |
| −98 | 3 | OCHF₂ | F | H | F | F |
| −99 | 3 | —CN | H | H | H | H |
| −100 | 3 | —CN | F | H | H | H |
| −101 | 3 | —CN | F | F | H | H |
| −102 | 3 | —CN | F | F | F | H |
| −103 | 3 | —CN | F | F | F | F |
| −104 | 3 | —CN | F | H | F | H |
| −105 | 3 | —CN | F | H | F | F |
| −106 | 4 | F | H | H | H | H |
| −107 | 4 | F | F | H | H | H |
| −108 | 4 | F | F | F | H | H |
| −109 | 4 | F | F | F | F | H |
| −110 | 4 | F | F | F | F | F |
| −111 | 4 | F | F | H | F | H |
| −112 | 4 | F | F | H | F | F |
| −113 | 4 | CF₃ | H | H | H | H |
| −114 | 4 | CF₃ | F | H | H | H |
| −115 | 4 | CF₃ | F | F | H | H |
| −116 | 4 | CF₃ | F | F | F | H |
| −117 | 4 | CF₃ | F | F | F | F |
| −118 | 4 | CF₃ | F | H | F | H |
| −119 | 4 | CF₃ | F | H | F | F |
| −120 | 4 | OCF₃ | H | H | H | H |
| −121 | 4 | OCF₃ | F | H | H | H |
| −122 | 4 | OCF₃ | F | F | H | H |
| −123 | 4 | OCF₃ | F | F | F | H |
| −124 | 4 | OCF₃ | F | F | F | F |
| −125 | 4 | OCF₃ | F | H | F | H |
| −126 | 4 | OCF₃ | F | H | F | F |
| −127 | 4 | OCHF₂ | H | H | H | H |
| −128 | 4 | OCHF₂ | F | H | H | H |
| −129 | 4 | OCHF₂ | F | F | H | H |
| −130 | 4 | OCHF₂ | F | F | F | H |
| −131 | 4 | OCHF₂ | F | F | F | F |
| −132 | 4 | OCHF₂ | F | H | F | H |
| −133 | 4 | OCHF₂ | F | H | F | F |
| −134 | 4 | —CN | H | H | H | H |
| −135 | 4 | —CN | F | H | H | H |
| −136 | 4 | —CN | F | F | H | H |
| −137 | 4 | —CN | F | F | F | H |
| −138 | 4 | —CN | F | F | F | F |
| −139 | 4 | —CN | F | H | F | H |
| −140 | 4 | —CN | F | H | F | F |
| −141 | 5 | F | H | H | H | H |
| −142 | 5 | F | F | H | H | H |
| −143 | 5 | F | F | F | H | H |
| −144 | 5 | F | F | F | F | H |
| −145 | 5 | F | F | F | F | F |
| −146 | 5 | F | F | H | F | H |
| −147 | 5 | F | F | H | F | F |
| −148 | 5 | CF₃ | H | H | H | H |
| −149 | 5 | CF₃ | F | H | H | H |
| −150 | 5 | CF₃ | F | F | H | H |
| −151 | 5 | CF₃ | F | F | F | H |
| −152 | 5 | CF₃ | F | F | F | F |
| −153 | 5 | CF₃ | F | H | F | H |
| −154 | 5 | CF₃ | F | H | F | F |
| −155 | 5 | OCF₃ | H | H | H | H |
| −156 | 5 | OCF₃ | F | H | H | H |
| −157 | 5 | OCF₃ | F | F | H | H |
| −158 | 5 | OCF₃ | F | F | F | H |
| −159 | 5 | OCF₃ | F | F | F | F |
| −160 | 5 | OCF₃ | F | H | F | H |
| −161 | 5 | OCF₃ | F | H | F | F |
| −162 | 5 | OCHF₂ | H | H | H | H |
| −163 | 5 | OCHF₂ | F | H | H | H |
| −164 | 5 | OCHF₂ | F | F | H | H |
| −165 | 5 | OCHF₂ | F | F | F | H |
| −166 | 5 | OCHF₂ | F | F | F | F |
| −167 | 5 | OCHF₂ | F | H | F | H |
| −168 | 5 | OCHF₂ | F | H | F | F |
| −169 | 5 | —CN | H | H | H | H |
| −170 | 5 | —CN | F | H | H | H |
| −171 | 5 | —CN | F | F | H | H |
| −172 | 5 | —CN | F | F | F | H |
| −173 | 5 | —CN | F | F | F | F |
| −174 | 5 | —CN | F | H | F | H |
| −175 | 5 | —CN | F | H | F | F |

*The radical $C_nH_{2n+1}$ is unbranched.
**L¹⁵ for the compounds of the formula I-SBAIa
***L¹⁶ for the compounds of the formula I-SBAIa

TABLE 3

| Compound I-DBAIa-/I-DBAIb-/I-DBAIIa-/I-DBAIIb-/I-EBCIa-/I-QBBIa No. | n* | R¹² | L¹¹ | L¹² |
|---|---|---|---|---|
| −1 | 0 | F | H | H |
| −2 | 0 | F | F | H |
| −3 | 0 | F | F | F |
| −4 | 0 | CF₃ | H | H |
| −5 | 0 | CF₃ | F | H |
| −6 | 0 | CF₃ | F | F |
| −7 | 0 | OCF₃ | H | H |
| −8 | 0 | OCF₃ | F | H |
| −9 | 0 | OCF₃ | F | F |
| −10 | 0 | OCHF₂ | H | H |
| −11 | 0 | OCHF₂ | F | H |
| −12 | 0 | OCHF₂ | F | F |
| −13 | 0 | —CN | H | H |
| −14 | 0 | —CN | F | H |
| −15 | 0 | —CN | F | F |
| −16 | 1 | F | H | H |
| −17 | 1 | F | F | H |
| −18 | 1 | F | F | F |
| −19 | 1 | CF₃ | H | H |
| −20 | 1 | CF₃ | F | H |
| −21 | 1 | CF₃ | F | F |
| −22 | 1 | OCF₃ | H | H |
| −23 | 1 | OCF₃ | F | H |
| −24 | 1 | OCF₃ | F | F |
| −25 | 1 | OCHF₂ | H | H |
| −26 | 1 | OCHF₂ | F | H |
| −27 | 1 | OCHF₂ | F | F |
| −28 | 1 | —CN | H | H |
| −29 | 1 | —CN | F | H |
| −30 | 1 | —CN | F | F |
| −31 | 2 | F | H | H |

TABLE 3-continued

| Compound I-DBAIa-/I-DBAIb-/I-DBAIIa-/I-DBAIIb-/I-EBCIa-/I-QBBIa No. | n* | $R^{12}$ | $L^{11}$ | $L^{12}$ |
|---|---|---|---|---|
| −32 | 2 | F | F | H |
| −33 | 2 | F | F | F |
| −34 | 2 | $CF_3$ | H | H |
| −35 | 2 | $CF_3$ | F | H |
| −36 | 2 | $CF_3$ | F | F |
| −37 | 2 | $OCF_3$ | H | H |
| −38 | 2 | $OCF_3$ | F | H |
| −39 | 2 | $OCF_3$ | F | F |
| −40 | 2 | $OCHF_2$ | H | H |
| −41 | 2 | $OCHF_2$ | F | H |
| −42 | 2 | $OCHF_2$ | F | F |
| −43 | 2 | —CN | H | H |
| −44 | 2 | —CN | F | H |
| −45 | 2 | —CN | F | F |
| −46 | 3 | F | H | H |
| −47 | 3 | F | F | H |
| −48 | 3 | F | F | F |
| −49 | 3 | $CF_3$ | H | H |
| −50 | 3 | $CF_3$ | F | H |
| −51 | 3 | $CF_3$ | F | F |
| −52 | 3 | $OCF_3$ | H | H |
| −53 | 3 | $OCF_3$ | F | H |
| −54 | 3 | $OCF_3$ | F | F |
| −55 | 3 | $OCHF_2$ | H | H |
| −56 | 3 | $OCHF_2$ | F | H |
| −57 | 3 | $OCHF_2$ | F | F |
| −58 | 3 | —CN | H | H |
| −59 | 3 | —CN | F | H |
| −60 | 3 | —CN | F | F |
| −61 | 4 | F | H | H |
| −62 | 4 | F | F | H |
| −63 | 4 | F | F | F |
| −64 | 4 | $CF_3$ | H | H |
| −65 | 4 | $CF_3$ | F | H |
| −66 | 4 | $CF_3$ | F | F |
| −67 | 4 | $OCF_3$ | H | H |
| −68 | 4 | $OCF_3$ | F | H |
| −69 | 4 | $OCF_3$ | F | F |
| −70 | 4 | $OCHF_2$ | H | H |
| −71 | 4 | $OCHF_2$ | F | H |
| −72 | 4 | $OCHF_2$ | F | F |
| −73 | 4 | —CN | H | H |
| −74 | 4 | —CN | F | H |
| −75 | 4 | —CN | F | F |
| −76 | 5 | F | H | H |
| −77 | 5 | F | F | H |
| −78 | 5 | F | F | F |
| −79 | 5 | $CF_3$ | H | H |
| −80 | 5 | $CF_3$ | F | H |
| −81 | 5 | $CF_3$ | F | F |
| −82 | 5 | $OCF_3$ | H | H |
| −83 | 5 | $OCF_3$ | F | H |
| −84 | 5 | $OCF_3$ | F | F |
| −85 | 5 | $OCHF_2$ | H | H |
| −86 | 5 | $OCHF_2$ | F | H |
| −87 | 5 | $OCHF_2$ | F | F |
| −88 | 5 | —CN | H | H |
| −89 | 5 | —CN | F | H |
| −90 | 5 | —CN | F | F |

*The radical $C_nH_{2n+1}$ is unbranched.

TABLE 4

| Compound I-DBAIIIa-/I-DBAIIIb-/I-NBBIa No. | n* | $R^{12}$ | $L^{11}$ | $L^{12}$ | $L^{13}$ | $L^{14}$ |
|---|---|---|---|---|---|---|
| −1 | 0 | F | H | H | H | H |
| −2 | 0 | F | F | H | H | H |
| −3 | 0 | F | F | F | H | H |
| −4 | 0 | F | F | F | F | H |
| −5 | 0 | F | F | F | F | F |
| −6 | 0 | F | F | H | F | H |
| −7 | 0 | F | F | H | F | F |
| −8 | 0 | $CF_3$ | H | H | H | H |
| −9 | 0 | $CF_3$ | F | H | H | H |
| −10 | 0 | $CF_3$ | F | F | H | H |
| −11 | 0 | $CF_3$ | F | F | F | H |
| −12 | 0 | $CF_3$ | F | F | F | F |
| −13 | 0 | $CF_3$ | F | H | F | H |
| −14 | 0 | $CF_3$ | F | H | F | F |
| −15 | 0 | $OCF_3$ | H | H | H | H |
| −16 | 0 | $OCF_3$ | F | H | H | H |
| −17 | 0 | $OCF_3$ | F | F | H | H |
| −18 | 0 | $OCF_3$ | F | F | F | H |
| −19 | 0 | $OCF_3$ | F | F | F | F |
| −20 | 0 | $OCF_3$ | F | H | F | H |
| −21 | 0 | $OCF_3$ | F | H | F | F |
| −22 | 0 | $OCHF_2$ | H | H | H | H |
| −23 | 0 | $OCHF_2$ | F | H | H | H |
| −24 | 0 | $OCHF_2$ | F | F | H | H |
| −25 | 0 | $OCHF_2$ | F | F | F | H |
| −26 | 0 | $OCHF_2$ | F | F | F | F |
| −27 | 0 | $OCHF_2$ | F | H | F | H |
| −28 | 0 | $OCHF_2$ | F | H | F | F |
| −29 | 0 | —CN | H | H | H | H |
| −30 | 0 | —CN | F | H | H | H |
| −31 | 0 | —CN | F | F | H | H |
| −32 | 0 | —CN | F | F | F | H |
| −33 | 0 | —CN | F | F | F | F |
| −34 | 0 | —CN | F | H | F | H |
| −35 | 0 | —CN | F | H | F | F |
| −36 | 1 | F | H | H | H | H |
| −37 | 1 | F | F | H | H | H |
| −38 | 1 | F | F | F | H | H |
| −39 | 1 | F | F | F | F | H |
| −40 | 1 | F | F | F | F | F |
| −41 | 1 | F | F | H | F | H |
| −42 | 1 | F | F | H | F | F |
| −43 | 1 | $CF_3$ | H | H | H | H |
| −44 | 1 | $CF_3$ | F | H | H | H |
| −45 | 1 | $CF_3$ | F | F | H | H |
| −46 | 1 | $CF_3$ | F | F | F | H |
| −47 | 1 | $CF_3$ | F | F | F | F |
| −48 | 1 | $CF_3$ | F | H | F | H |
| −49 | 1 | $CF_3$ | F | H | F | F |
| −50 | 1 | $OCF_3$ | H | H | H | H |
| −51 | 1 | $OCF_3$ | F | H | H | H |
| −52 | 1 | $OCF_3$ | F | F | H | H |
| −53 | 1 | $OCF_3$ | F | F | F | H |
| −54 | 1 | $OCF_3$ | F | F | F | F |
| −55 | 1 | $OCF_3$ | F | H | F | H |
| −56 | 1 | $OCF_3$ | F | H | F | F |
| −57 | 1 | $OCHF_2$ | H | H | H | H |
| −58 | 1 | $OCHF_2$ | F | H | H | H |
| −59 | 1 | $OCHF_2$ | F | F | H | H |
| −60 | 1 | $OCHF_2$ | F | F | F | H |
| −61 | 1 | $OCHF_2$ | F | F | F | F |
| −62 | 1 | $OCHF_2$ | F | H | F | H |
| −63 | 1 | $OCHF_2$ | F | H | F | F |
| −64 | 1 | —CN | H | H | H | H |
| −65 | 1 | —CN | F | H | H | H |
| −66 | 1 | —CN | F | F | H | H |
| −67 | 1 | —CN | F | F | F | H |
| −68 | 1 | —CN | F | F | F | F |
| −69 | 1 | —CN | F | H | F | H |
| −70 | 1 | —CN | F | H | F | F |
| −71 | 2 | F | H | H | H | H |
| −72 | 2 | F | F | H | H | H |
| −73 | 2 | F | F | F | H | H |
| −74 | 2 | F | F | F | F | H |
| −75 | 2 | F | F | F | F | F |
| −76 | 2 | F | F | H | F | H |
| −77 | 2 | F | F | H | F | F |
| −78 | 2 | $CF_3$ | H | H | H | H |
| −79 | 2 | $CF_3$ | F | H | H | H |

TABLE 4-continued

| Compound I-DBAIIIa-/I-DBAIIIb-/I-NBBIa No. | n* | R$^{12}$ | L$^{11}$ | L$^{12}$ | L$^{13}$ | L$^{14}$ |
|---|---|---|---|---|---|---|
| -80 | 2 | CF$_3$ | F | F | H | H |
| -81 | 2 | CF$_3$ | F | F | F | H |
| -82 | 2 | CF$_3$ | F | F | F | F |
| -83 | 2 | CF$_3$ | F | H | F | H |
| -84 | 2 | CF$_3$ | F | H | F | F |
| -85 | 2 | OCF$_3$ | H | H | H | H |
| -86 | 2 | OCF$_3$ | F | H | H | H |
| -87 | 2 | OCF$_3$ | F | F | H | H |
| -88 | 2 | OCF$_3$ | F | F | F | H |
| -89 | 2 | OCF$_3$ | F | F | F | F |
| -90 | 2 | OCF$_3$ | F | H | F | H |
| -91 | 2 | OCF$_3$ | F | H | F | F |
| -92 | 2 | OCHF$_2$ | H | H | H | H |
| -93 | 2 | OCHF$_2$ | F | H | H | H |
| -94 | 2 | OCHF$_2$ | F | F | H | H |
| -95 | 2 | OCHF$_2$ | F | F | F | H |
| -96 | 2 | OCHF$_2$ | F | F | F | F |
| -97 | 2 | OCHF$_2$ | F | H | F | H |
| -98 | 2 | OCHF$_2$ | F | H | F | F |
| -99 | 2 | —CN | H | H | H | H |
| -100 | 2 | —CN | F | H | H | H |
| -101 | 2 | —CN | F | F | H | H |
| -102 | 2 | —CN | F | F | F | H |
| -103 | 2 | —CN | F | F | F | F |
| -104 | 2 | —CN | F | H | F | H |
| -105 | 2 | —CN | F | H | F | F |
| -106 | 3 | F | H | H | H | H |
| -107 | 3 | F | F | H | H | H |
| -108 | 3 | F | F | F | H | H |
| -109 | 3 | F | F | F | F | H |
| -110 | 3 | F | F | F | F | F |
| -111 | 3 | F | F | H | F | H |
| -112 | 3 | F | F | H | F | F |
| -113 | 3 | CF$_3$ | H | H | H | H |
| -114 | 3 | CF$_3$ | F | H | H | H |
| -115 | 3 | CF$_3$ | F | F | H | H |
| -116 | 3 | CF$_3$ | F | F | F | H |
| -117 | 3 | CF$_3$ | F | F | F | F |
| -118 | 3 | CF$_3$ | F | H | F | H |
| -119 | 3 | CF$_3$ | F | H | F | F |
| -120 | 3 | OCF$_3$ | H | H | H | H |
| -121 | 3 | OCF$_3$ | F | H | H | H |
| -122 | 3 | OCF$_3$ | F | F | H | H |
| -123 | 3 | OCF$_3$ | F | F | F | H |
| -124 | 3 | OCF$_3$ | F | F | F | F |
| -125 | 3 | OCF$_3$ | F | H | F | H |
| -126 | 3 | OCF$_3$ | F | H | F | F |
| -127 | 3 | OCHF$_2$ | H | H | H | H |
| -128 | 3 | OCHF$_2$ | F | H | H | H |
| -129 | 3 | OCHF$_2$ | F | F | H | H |
| -130 | 3 | OCHF$_2$ | F | F | F | H |
| -131 | 3 | OCHF$_2$ | F | F | F | F |
| -132 | 3 | OCHF$_2$ | F | H | F | H |
| -133 | 3 | OCHF$_2$ | F | H | F | F |
| -134 | 3 | —CN | H | H | H | H |
| -135 | 3 | —CN | F | H | H | H |
| -136 | 3 | —CN | F | F | H | H |
| -137 | 3 | —CN | F | F | F | H |
| -138 | 3 | —CN | F | F | F | F |
| -139 | 3 | —CN | F | H | F | H |
| -140 | 3 | —CN | F | H | F | F |
| -141 | 4 | F | H | H | H | H |
| -142 | 4 | F | F | H | H | H |
| -143 | 4 | F | F | F | H | H |
| -144 | 4 | F | F | F | F | H |
| -145 | 4 | F | F | F | F | F |
| -146 | 4 | F | F | H | F | H |
| -147 | 4 | F | F | H | F | F |
| -148 | 4 | CF$_3$ | H | H | H | H |
| -149 | 4 | CF$_3$ | F | H | H | H |
| -150 | 4 | CF$_3$ | F | F | H | H |
| -151 | 4 | CF$_3$ | F | F | F | H |
| -152 | 4 | CF$_3$ | F | F | F | F |
| -153 | 4 | CF$_3$ | F | H | F | H |
| -154 | 4 | CF$_3$ | F | H | F | F |
| -155 | 4 | OCF$_3$ | H | H | H | H |
| -156 | 4 | OCF$_3$ | F | H | H | H |
| -157 | 4 | OCF$_3$ | F | F | H | H |
| -158 | 4 | OCF$_3$ | F | F | F | H |
| -159 | 4 | OCF$_3$ | F | F | F | F |
| -160 | 4 | OCF$_3$ | F | H | F | H |
| -161 | 4 | OCF$_3$ | F | H | F | F |
| -162 | 4 | OCHF$_2$ | H | H | H | H |
| -163 | 4 | OCHF$_2$ | F | H | H | H |
| -164 | 4 | OCHF$_2$ | F | F | H | H |
| -165 | 4 | OCHF$_2$ | F | F | F | H |
| -166 | 4 | OCHF$_2$ | F | F | F | F |
| -167 | 4 | OCHF$_2$ | F | H | F | H |
| -168 | 4 | OCHF$_2$ | F | H | F | F |
| -169 | 4 | —CN | H | H | H | H |
| -170 | 4 | —CN | F | H | H | H |
| -171 | 4 | —CN | F | F | H | H |
| -172 | 4 | —CN | F | F | F | H |
| -173 | 4 | —CN | F | F | F | F |
| -174 | 4 | —CN | F | H | F | H |
| -175 | 4 | —CN | F | H | F | F |
| -176 | 5 | F | H | H | H | H |
| -177 | 5 | F | F | H | H | H |
| -178 | 5 | F | F | F | H | H |
| -179 | 5 | F | F | F | F | H |
| -180 | 5 | F | F | F | F | F |
| -181 | 5 | F | F | H | F | H |
| -182 | 5 | F | F | H | F | F |
| -183 | 5 | CF$_3$ | H | H | H | H |
| -184 | 5 | CF$_3$ | F | H | H | H |
| -185 | 5 | CF$_3$ | F | F | H | H |
| -186 | 5 | CF$_3$ | F | F | F | H |
| -187 | 5 | CF$_3$ | F | F | F | F |
| -188 | 5 | CF$_3$ | F | H | F | H |
| -189 | 5 | CF$_3$ | F | H | F | F |
| -190 | 5 | OCF$_3$ | H | H | H | H |
| -191 | 5 | OCF$_3$ | F | H | H | H |
| -192 | 5 | OCF$_3$ | F | F | H | H |
| -193 | 5 | OCF$_3$ | F | F | F | H |
| -194 | 5 | OCF$_3$ | F | F | F | F |
| -195 | 5 | OCF$_3$ | F | H | F | H |
| -196 | 5 | OCF$_3$ | F | H | F | F |
| -197 | 5 | OCHF$_2$ | H | H | H | H |
| -198 | 5 | OCHF$_2$ | F | H | H | H |
| -199 | 5 | OCHF$_2$ | F | F | H | H |
| -200 | 5 | OCHF$_2$ | F | F | F | H |
| -201 | 5 | OCHF$_2$ | F | F | F | F |
| -202 | 5 | OCHF$_2$ | F | H | F | H |
| -203 | 5 | OCHF$_2$ | F | H | F | F |
| -204 | 5 | —CN | H | H | H | H |
| -205 | 5 | —CN | F | H | H | H |
| -206 | 5 | —CN | F | F | H | H |
| -207 | 5 | —CN | F | F | F | H |
| -208 | 5 | —CN | F | F | F | F |
| -209 | 5 | —CN | F | H | F | H |
| -210 | 5 | —CN | F | H | F | F |

TABLE 5

| Compound I-GBIa | n* | R$^{12b}$ | Compound I-GBIa | n* | R$^{12b}$ |
|---|---|---|---|---|---|
| -1 | 0 | H | -2 | 0 | CH$_3$ |
| -3 | 0 | C$_2$H$_5$ | -4 | 0 | n-C$_3$H$_7$ |
| -5 | 0 | t-C$_4$H$_9$ | -6 | 0 | CH$_2$-phenyl |
| -7 | 1 | H | -8 | 1 | CH$_3$ |
| -9 | 1 | C$_2$H$_5$ | -10 | 1 | n-C$_3$H$_7$ |
| -11 | 1 | t-C$_4$H$_9$ | -12 | 1 | CH$_2$-phenyl |
| -13 | 3 | H | -14 | 3 | CH$_3$ |
| -15 | 3 | C$_2$H$_5$ | -16 | 3 | n-C$_3$H$_7$ |
| -17 | 3 | t-C$_4$H$_9$ | -18 | 3 | CH$_2$-phenyl |
| -19 | 5 | H | -20 | 5 | CH$_3$ |

TABLE 5-continued

| Compound I-GBIa | n* | R$^{12b}$ | Compound I-GBIa | n* | R$^{12b}$ |
|---|---|---|---|---|---|
| -21 | 5 | C$_2$H$_5$ | -22 | 5 | n-C$_3$H$_7$ |
| -23 | 5 | t-C$_4$H$_9$ | -24 | 5 | CH$_2$-phenyl |

*The radical C$_n$H$_{2n+1}$ is unbranched.

TABLE 6

| Compound I-SBBIa No. | n* | R$^{12}$ | L$^{11}$ | L$^{12}$ | L$^{15}$ | L$^{16}$ | L$^{13}$ | L$^{14}$ |
|---|---|---|---|---|---|---|---|---|
| -1 | 1 | F | H | H | H | H | H | H |
| -2 | 1 | F | F | H | H | H | H | H |
| -3 | 1 | F | F | F | H | H | H | H |
| -4 | 1 | F | F | F | F | H | H | H |
| -5 | 1 | F | F | F | F | F | H | H |
| -6 | 1 | F | F | H | F | H | H | H |
| -7 | 1 | F | F | H | F | F | H | H |
| -8 | 1 | F | H | H | H | H | F | H |
| -9 | 1 | F | F | H | H | H | F | H |
| -10 | 1 | F | F | F | H | H | F | H |
| -11 | 1 | F | F | F | F | H | F | H |
| -12 | 1 | F | F | F | F | F | F | H |
| -13 | 1 | F | F | H | F | H | F | H |
| -14 | 1 | F | F | H | F | F | F | H |
| -15 | 1 | CF$_3$ | H | H | H | H | H | H |
| -16 | 1 | CF$_3$ | F | H | H | H | H | H |
| -17 | 1 | CF$_3$ | F | F | H | H | H | H |
| -18 | 1 | CF$_3$ | F | F | F | H | H | H |
| -19 | 1 | CF$_3$ | F | F | F | F | H | H |
| -20 | 1 | CF$_3$ | F | H | F | H | H | H |
| -21 | 1 | CF$_3$ | F | H | F | F | H | H |
| -22 | 1 | CF$_3$ | H | H | H | H | F | H |
| -23 | 1 | CF$_3$ | F | H | H | H | F | H |
| -24 | 1 | CF$_3$ | F | F | H | H | F | H |
| -25 | 1 | CF$_3$ | F | F | F | H | F | H |
| -26 | 1 | CF$_3$ | F | F | F | F | F | H |
| -27 | 1 | CF$_3$ | F | H | F | H | F | H |
| -28 | 1 | CF$_3$ | F | H | F | F | F | H |
| -29 | 1 | OCF$_3$ | H | H | H | H | H | H |
| -30 | 1 | OCF$_3$ | F | H | H | H | H | H |
| -31 | 1 | OCF$_3$ | F | F | H | H | H | H |
| -32 | 1 | OCF$_3$ | F | F | F | H | H | H |
| -33 | 1 | OCF$_3$ | F | F | F | F | H | H |
| -34 | 1 | OCF$_3$ | F | H | F | H | H | H |
| -35 | 1 | OCF$_3$ | F | H | F | F | H | H |
| -36 | 1 | OCF$_3$ | H | H | H | H | F | H |
| -37 | 1 | OCF$_3$ | F | H | H | H | F | H |
| -38 | 1 | OCF$_3$ | F | F | H | H | F | H |
| -39 | 1 | OCF$_3$ | F | F | F | H | F | H |
| -40 | 1 | OCF$_3$ | F | F | F | F | F | H |
| -41 | 1 | OCF$_3$ | F | H | F | H | F | H |
| -42 | 1 | OCF$_3$ | F | H | F | F | F | H |
| -43 | 1 | OCHF$_2$ | H | H | H | H | H | H |
| -44 | 1 | OCHF$_2$ | F | H | H | H | H | H |
| -45 | 1 | OCHF$_2$ | F | F | H | H | H | H |
| -46 | 1 | OCHF$_2$ | F | F | F | H | H | H |
| -47 | 1 | OCHF$_2$ | F | F | F | F | H | H |
| -48 | 1 | OCHF$_2$ | F | H | F | H | H | H |
| -49 | 1 | OCHF$_2$ | F | H | F | F | H | H |
| -50 | 1 | OCHF$_2$ | H | H | H | H | F | H |
| -51 | 1 | OCHF$_2$ | F | H | H | H | F | H |
| -52 | 1 | OCHF$_2$ | F | F | H | H | F | H |
| -53 | 1 | OCHF$_2$ | F | F | F | H | F | H |
| -54 | 1 | OCHF$_2$ | F | F | F | F | F | H |
| -55 | 1 | OCHF$_2$ | F | H | F | H | F | H |
| -56 | 1 | OCHF$_2$ | F | H | F | F | F | H |
| -57 | 1 | —CN | H | H | H | H | H | H |
| -58 | 1 | —CN | F | H | H | H | H | H |
| -59 | 1 | —CN | F | F | H | H | H | H |
| -60 | 1 | —CN | F | F | F | H | H | H |
| -61 | 1 | —CN | F | F | F | F | H | H |
| -62 | 1 | —CN | F | H | F | H | H | H |
| -63 | 1 | —CN | F | H | F | F | H | H |
| -64 | 1 | —CN | H | H | H | H | F | H |
| -65 | 1 | —CN | F | H | H | H | F | H |
| -66 | 1 | —CN | F | F | H | H | F | H |
| -67 | 1 | —CN | F | F | F | H | F | H |
| -68 | 1 | —CN | F | F | F | F | F | H |
| -69 | 1 | —CN | F | H | F | H | F | H |
| -70 | 1 | —CN | F | H | F | F | F | H |
| -71 | 2 | F | H | H | H | H | H | H |
| -72 | 2 | F | F | H | H | H | H | H |
| -73 | 2 | F | F | F | H | H | H | H |
| -74 | 2 | F | F | F | F | H | H | H |
| -75 | 2 | F | F | F | F | F | H | H |
| -76 | 2 | F | F | H | F | H | H | H |
| -77 | 2 | F | F | H | F | F | H | H |
| -78 | 2 | F | H | H | H | H | F | H |
| -79 | 2 | F | F | H | H | H | F | H |
| -80 | 2 | F | F | F | H | H | F | H |
| -81 | 2 | F | F | F | F | H | F | H |
| -82 | 2 | F | F | F | F | F | F | H |
| -83 | 2 | F | F | H | F | H | F | H |
| -84 | 2 | F | F | H | F | F | F | H |
| -85 | 2 | CF$_3$ | H | H | H | H | H | H |
| -86 | 2 | CF$_3$ | F | H | H | H | H | H |
| -87 | 2 | CF$_3$ | F | F | H | H | H | H |
| -88 | 2 | CF$_3$ | F | F | F | H | H | H |
| -89 | 2 | CF$_3$ | F | F | F | F | H | H |
| -90 | 2 | CF$_3$ | F | H | F | H | H | H |
| -91 | 2 | CF$_3$ | F | H | F | F | H | H |
| -92 | 2 | CF$_3$ | H | H | H | H | F | H |
| -93 | 2 | CF$_3$ | F | H | H | H | F | H |
| -94 | 2 | CF$_3$ | F | F | H | H | F | H |
| -95 | 2 | CF$_3$ | F | F | F | H | F | H |
| -96 | 2 | CF$_3$ | F | F | F | F | F | H |
| -97 | 2 | CF$_3$ | F | H | F | H | F | H |
| -98 | 2 | CF$_3$ | F | H | F | F | F | H |
| -99 | 2 | OCF$_3$ | H | H | H | H | H | H |
| -100 | 2 | OCF$_3$ | F | H | H | H | H | H |
| -101 | 2 | OCF$_3$ | F | F | H | H | H | H |
| -102 | 2 | OCF$_3$ | F | F | F | H | H | H |
| -103 | 2 | OCF$_3$ | F | F | F | F | H | H |
| -104 | 2 | OCF$_3$ | F | H | F | H | H | H |
| -105 | 2 | OCF$_3$ | F | H | F | F | H | H |
| -106 | 2 | OCF$_3$ | H | H | H | H | F | H |
| -107 | 2 | OCF$_3$ | F | H | H | H | F | H |
| -108 | 2 | OCF$_3$ | F | F | H | H | F | H |
| -109 | 2 | OCF$_3$ | F | F | F | H | F | H |
| -110 | 2 | OCF$_3$ | F | F | F | F | F | H |
| -111 | 2 | OCF$_3$ | F | H | F | H | F | H |
| -112 | 2 | OCF$_3$ | F | H | F | F | F | H |
| -113 | 2 | OCHF$_2$ | H | H | H | H | H | H |
| -114 | 2 | OCHF$_2$ | F | H | H | H | H | H |
| -115 | 2 | OCHF$_2$ | F | F | H | H | H | H |
| -116 | 2 | OCHF$_2$ | F | F | F | H | H | H |
| -117 | 2 | OCHF$_2$ | F | F | F | F | H | H |
| -118 | 2 | OCHF$_2$ | F | H | F | H | H | H |
| -119 | 2 | OCHF$_2$ | F | H | F | F | H | H |
| -120 | 2 | OCHF$_2$ | H | H | H | H | F | H |
| -121 | 2 | OCHF$_2$ | F | H | H | H | F | H |
| -122 | 2 | OCHF$_2$ | F | F | H | H | F | H |
| -123 | 2 | OCHF$_2$ | F | F | F | H | F | H |
| -124 | 2 | OCHF$_2$ | F | F | F | F | F | H |
| -125 | 2 | OCHF$_2$ | F | H | F | H | F | H |
| -126 | 2 | OCHF$_2$ | F | H | F | F | F | H |
| -127 | 2 | —CN | H | H | H | H | H | H |
| -128 | 2 | —CN | F | H | H | H | H | H |
| -129 | 2 | —CN | F | F | H | H | H | H |
| -130 | 2 | —CN | F | F | F | H | H | H |
| -131 | 2 | —CN | F | F | F | F | H | H |
| -132 | 2 | —CN | F | H | F | H | H | H |
| -133 | 2 | —CN | F | H | F | F | H | H |
| -134 | 2 | —CN | H | H | H | H | F | H |
| -135 | 2 | —CN | F | H | H | H | F | H |
| -136 | 2 | —CN | F | F | H | H | F | H |
| -137 | 2 | —CN | F | F | F | H | F | H |
| -138 | 2 | —CN | F | F | F | F | F | H |
| -139 | 2 | —CN | F | H | F | H | F | H |
| -140 | 2 | —CN | F | H | F | F | F | H |

TABLE 6-continued

| Compound I-SBBIa No. | n* | R$^{12}$ | L$^{11}$ | L$^{12}$ | L$^{15}$ | L$^{16}$ | L$^{13}$ | L$^{14}$ |
|---|---|---|---|---|---|---|---|---|
| −141 | 3 | F | H | H | H | H | H | H |
| −142 | 3 | F | F | H | H | H | H | H |
| −143 | 3 | F | F | F | H | H | H | H |
| −144 | 3 | F | F | F | F | H | H | H |
| −145 | 3 | F | F | F | F | F | H | H |
| −146 | 3 | F | H | F | H | H | H | H |
| −147 | 3 | F | H | F | F | H | H | H |
| −148 | 3 | F | H | H | H | H | F | H |
| −149 | 3 | F | F | H | H | H | F | H |
| −150 | 3 | F | F | F | H | H | F | H |
| −151 | 3 | F | F | F | F | H | F | H |
| −152 | 3 | F | F | F | F | F | F | H |
| −153 | 3 | F | H | F | H | H | F | H |
| −154 | 3 | F | F | H | F | F | F | H |
| −155 | 3 | CF$_3$ | H | H | H | H | H | H |
| −156 | 3 | CF$_3$ | F | H | H | H | H | H |
| −157 | 3 | CF$_3$ | F | F | H | H | H | H |
| −158 | 3 | CF$_3$ | F | F | F | H | H | H |
| −159 | 3 | CF$_3$ | F | F | F | F | H | H |
| −160 | 3 | CF$_3$ | F | H | F | H | H | H |
| −161 | 3 | CF$_3$ | F | H | F | F | H | H |
| −162 | 3 | CF$_3$ | H | H | H | H | F | H |
| −163 | 3 | CF$_3$ | F | H | H | H | F | H |
| −164 | 3 | CF$_3$ | F | F | H | H | F | H |
| −165 | 3 | CF$_3$ | F | F | F | H | F | H |
| −166 | 3 | CF$_3$ | F | F | F | F | F | H |
| −167 | 3 | CF$_3$ | F | H | F | H | F | H |
| −168 | 3 | CF$_3$ | F | H | F | F | F | H |
| −169 | 3 | OCF$_3$ | H | H | H | H | H | H |
| −170 | 3 | OCF$_3$ | F | H | H | H | H | H |
| −171 | 3 | OCF$_3$ | F | F | H | H | H | H |
| −172 | 3 | OCF$_3$ | F | F | F | H | H | H |
| −173 | 3 | OCF$_3$ | F | F | F | F | H | H |
| −174 | 3 | OCF$_3$ | F | H | F | H | H | H |
| −175 | 3 | OCF$_3$ | F | H | F | F | H | H |
| −176 | 3 | OCF$_3$ | H | H | H | H | F | H |
| −177 | 3 | OCF$_3$ | F | H | H | H | F | H |
| −178 | 3 | OCF$_3$ | F | F | H | H | F | H |
| −179 | 3 | OCF$_3$ | F | F | F | H | F | H |
| −180 | 3 | OCF$_3$ | F | F | F | F | F | H |
| −181 | 3 | OCF$_3$ | F | H | F | H | F | H |
| −182 | 3 | OCF$_3$ | F | H | F | F | F | H |
| −183 | 3 | OCHF$_2$ | H | H | H | H | H | H |
| −184 | 3 | OCHF$_2$ | F | H | H | H | H | H |
| −185 | 3 | OCHF$_2$ | F | F | H | H | H | H |
| −186 | 3 | OCHF$_2$ | F | F | F | H | H | H |
| −187 | 3 | OCHF$_2$ | F | F | F | F | H | H |
| −188 | 3 | OCHF$_2$ | F | H | F | H | H | H |
| −189 | 3 | OCHF$_2$ | F | H | F | F | H | H |
| −190 | 3 | OCHF$_2$ | H | H | H | H | F | H |
| −191 | 3 | OCHF$_2$ | F | H | H | H | F | H |
| −192 | 3 | OCHF$_2$ | F | F | H | H | F | H |
| −193 | 3 | OCHF$_2$ | F | F | F | H | F | H |
| −194 | 3 | OCHF$_2$ | F | F | F | F | F | H |
| −195 | 3 | OCHF$_2$ | F | H | F | H | F | H |
| −196 | 3 | OCHF$_2$ | F | H | F | F | F | H |
| −197 | 3 | —CN | H | H | H | H | H | H |
| −198 | 3 | —CN | F | H | H | H | H | H |
| −199 | 3 | —CN | F | F | H | H | H | H |
| −200 | 3 | —CN | F | F | F | H | H | H |
| −201 | 3 | —CN | F | F | F | F | H | H |
| −202 | 3 | —CN | F | H | F | H | H | H |
| −203 | 3 | —CN | F | H | F | F | H | H |
| −204 | 3 | —CN | H | H | H | H | F | H |
| −205 | 3 | —CN | F | H | H | H | F | H |
| −206 | 3 | —CN | F | F | H | H | F | H |
| −207 | 3 | —CN | F | F | F | H | F | H |
| −208 | 3 | —CN | F | F | F | F | F | H |
| −209 | 3 | —CN | F | H | F | H | F | H |
| −210 | 3 | —CN | F | H | F | F | F | H |
| −211 | 4 | F | H | H | H | H | H | H |
| −212 | 4 | F | F | H | H | H | H | H |
| −213 | 4 | F | F | F | H | H | H | H |
| −214 | 4 | F | F | F | F | H | H | H |
| −215 | 4 | F | F | F | F | F | H | H |
| −216 | 4 | F | F | H | F | H | H | H |
| −217 | 4 | F | F | H | F | F | H | H |
| −218 | 4 | F | H | H | H | H | F | H |
| −219 | 4 | F | F | H | H | H | F | H |
| −220 | 4 | F | F | F | H | H | F | H |
| −221 | 4 | F | F | F | F | H | F | H |
| −222 | 4 | F | F | F | F | F | F | H |
| −223 | 4 | F | F | H | F | H | F | H |
| −224 | 4 | F | F | H | F | F | F | H |
| −225 | 4 | CF$_3$ | H | H | H | H | H | H |
| −226 | 4 | CF$_3$ | F | H | H | H | H | H |
| −227 | 4 | CF$_3$ | F | F | H | H | H | H |
| −228 | 4 | CF$_3$ | F | F | F | H | H | H |
| −229 | 4 | CF$_3$ | F | F | F | F | H | H |
| −230 | 4 | CF$_3$ | F | H | F | H | H | H |
| −231 | 4 | CF$_3$ | F | H | F | F | H | H |
| −232 | 4 | CF$_3$ | H | H | H | H | F | H |
| −233 | 4 | CF$_3$ | F | H | H | H | F | H |
| −234 | 4 | CF$_3$ | F | F | H | H | F | H |
| −235 | 4 | CF$_3$ | F | F | F | H | F | H |
| −236 | 4 | CF$_3$ | F | F | F | F | F | H |
| −237 | 4 | CF$_3$ | F | H | F | H | F | H |
| −238 | 4 | CF$_3$ | F | H | F | F | F | H |
| −239 | 4 | OCF$_3$ | H | H | H | H | H | H |
| −240 | 4 | OCF$_3$ | F | H | H | H | H | H |
| −241 | 4 | OCF$_3$ | F | F | H | H | H | H |
| −242 | 4 | OCF$_3$ | F | F | F | H | H | H |
| −243 | 4 | OCF$_3$ | F | F | F | F | H | H |
| −244 | 4 | OCF$_3$ | F | H | F | H | H | H |
| −245 | 4 | OCF$_3$ | F | H | F | F | H | H |
| −246 | 4 | OCF$_3$ | H | H | H | H | F | H |
| −247 | 4 | OCF$_3$ | F | H | H | H | F | H |
| −248 | 4 | OCF$_3$ | F | F | H | H | F | H |
| −249 | 4 | OCF$_3$ | F | F | F | H | F | H |
| −250 | 4 | OCF$_3$ | F | F | F | F | F | H |
| −251 | 4 | OCF$_3$ | F | H | F | H | F | H |
| −252 | 4 | OCF$_3$ | F | H | F | F | F | H |
| −253 | 4 | OCHF$_2$ | H | H | H | H | H | H |
| −254 | 4 | OCHF$_2$ | F | H | H | H | H | H |
| −255 | 4 | OCHF$_2$ | F | F | H | H | H | H |
| −256 | 4 | OCHF$_2$ | F | F | F | H | H | H |
| −257 | 4 | OCHF$_2$ | F | F | F | F | H | H |
| −258 | 4 | OCHF$_2$ | F | H | F | H | H | H |
| −259 | 4 | OCHF$_2$ | F | H | F | F | H | H |
| −260 | 4 | OCHF$_2$ | H | H | H | H | F | H |
| −261 | 4 | OCHF$_2$ | F | H | H | H | F | H |
| −262 | 4 | OCHF$_2$ | F | F | H | H | F | H |
| −263 | 4 | OCHF$_2$ | F | F | F | H | F | H |
| −264 | 4 | OCHF$_2$ | F | F | F | F | F | H |
| −265 | 4 | OCHF$_2$ | F | H | F | H | F | H |
| −266 | 4 | OCHF$_2$ | F | H | F | F | F | H |
| −267 | 4 | —CN | H | H | H | H | H | H |
| −268 | 4 | —CN | F | H | H | H | H | H |
| −269 | 4 | —CN | F | F | H | H | H | H |
| −270 | 4 | —CN | F | F | F | H | H | H |
| −271 | 4 | —CN | F | F | F | F | H | H |
| −272 | 4 | —CN | F | H | F | H | H | H |
| −273 | 4 | —CN | F | H | F | F | H | H |
| −274 | 4 | —CN | H | H | H | H | F | H |
| −275 | 4 | —CN | F | H | H | H | F | H |
| −276 | 4 | —CN | F | F | H | H | F | H |

TABLE 6-continued

| Compound I-SBBIa No. | n* | $R^{12}$ | $L^{11}$ | $L^{12}$ | $L^{15}$ | $L^{16}$ | $L^{13}$ | $L^{14}$ |
|---|---|---|---|---|---|---|---|---|
| -277 | 4 | —CN | F | F | F | H | F | H |
| -278 | 4 | —CN | F | F | F | F | F | H |
| -279 | 4 | —CN | F | H | F | H | F | H |
| -280 | 4 | —CN | F | H | F | F | F | H |
| -281 | 5 | F | H | H | H | H | H | H |
| -282 | 5 | F | F | H | H | H | H | H |
| -283 | 5 | F | F | F | H | H | H | H |
| -284 | 5 | F | F | F | F | H | H | H |
| -285 | 5 | F | F | F | F | F | H | H |
| -286 | 5 | F | F | H | F | H | H | H |
| -287 | 5 | F | F | H | F | F | H | H |
| -288 | 5 | F | H | H | H | H | F | H |
| -289 | 5 | F | F | H | H | H | F | H |
| -290 | 5 | F | F | F | H | H | F | H |
| -291 | 5 | F | F | F | F | H | F | H |
| -292 | 5 | F | F | F | F | F | F | H |
| -293 | 5 | F | F | H | F | H | F | H |
| -294 | 5 | F | F | H | F | F | F | H |
| -295 | 5 | $CF_3$ | H | H | H | H | H | H |
| -296 | 5 | $CF_3$ | F | H | H | H | H | H |
| -297 | 5 | $CF_3$ | F | F | H | H | H | H |
| -298 | 5 | $CF_3$ | F | F | F | H | H | H |
| -299 | 5 | $CF_3$ | F | F | F | F | H | H |
| -300 | 5 | $CF_3$ | F | H | F | H | H | H |
| -301 | 5 | $CF_3$ | F | H | F | F | H | H |
| -302 | 5 | $CF_3$ | H | H | H | H | F | H |
| -303 | 5 | $CF_3$ | F | H | H | H | F | H |
| -304 | 5 | $CF_3$ | F | F | H | H | F | H |
| -305 | 5 | $CF_3$ | F | F | F | H | F | H |
| -306 | 5 | $CF_3$ | F | F | F | F | F | H |
| -307 | 5 | $CF_3$ | F | H | F | H | F | H |
| -308 | 5 | $CF_3$ | F | H | F | F | F | H |
| -309 | 5 | $OCF_3$ | H | H | H | H | H | H |
| -310 | 5 | $OCF_3$ | F | H | H | H | H | H |
| -311 | 5 | $OCF_3$ | F | F | H | H | H | H |
| -312 | 5 | $OCF_3$ | F | F | F | H | H | H |
| -313 | 5 | $OCF_3$ | F | F | F | F | H | H |
| -314 | 5 | $OCF_3$ | F | H | F | H | H | H |
| -315 | 5 | $OCF_3$ | F | H | F | F | H | H |
| -316 | 5 | $OCF_3$ | H | H | H | H | F | H |
| -317 | 5 | $OCF_3$ | F | H | H | H | F | H |
| -318 | 5 | $OCF_3$ | F | F | H | H | F | H |
| -319 | 5 | $OCF_3$ | F | F | F | H | F | H |
| -320 | 5 | $OCF_3$ | F | F | F | F | F | H |
| -321 | 5 | $OCF_3$ | F | H | F | H | F | H |
| -322 | 5 | $OCF_3$ | F | H | F | F | F | H |
| -323 | 5 | $OCHF_2$ | H | H | H | H | H | H |
| -324 | 5 | $OCHF_2$ | F | H | H | H | H | H |
| -325 | 5 | $OCHF_2$ | F | F | H | H | H | H |
| -326 | 5 | $OCHF_2$ | F | F | F | H | H | H |
| -327 | 5 | $OCHF_2$ | F | F | F | F | H | H |
| -328 | 5 | $OCHF_2$ | F | H | F | H | H | H |
| -329 | 5 | $OCHF_2$ | F | H | F | F | H | H |
| -330 | 5 | $OCHF_2$ | H | H | H | H | F | H |
| -331 | 5 | $OCHF_2$ | F | H | H | H | F | H |
| -332 | 5 | $OCHF_2$ | F | F | H | H | F | H |
| -333 | 5 | $OCHF_2$ | F | F | F | H | F | H |
| -334 | 5 | $OCHF_2$ | F | F | F | F | F | H |
| -335 | 5 | $OCHF_2$ | F | H | F | H | F | H |
| -336 | 5 | $OCHF_2$ | F | H | F | F | F | H |
| -337 | 5 | —CN | H | H | H | H | H | H |
| -338 | 5 | —CN | F | H | H | H | H | H |
| -339 | 5 | —CN | F | F | H | H | H | H |
| -340 | 5 | —CN | F | F | F | H | H | H |
| -341 | 5 | —CN | F | F | F | F | H | H |
| -342 | 5 | —CN | F | H | F | H | H | H |
| -343 | 5 | —CN | F | H | F | F | H | H |
| -344 | 5 | —CN | H | H | H | H | F | H |
| -345 | 5 | —CN | F | H | H | H | F | H |
| -346 | 5 | —CN | F | F | H | H | F | H |
| -347 | 5 | —CN | F | F | F | H | F | H |
| -348 | 5 | —CN | F | F | F | F | F | H |
| -349 | 5 | —CN | F | H | F | H | F | H |
| -350 | 5 | —CN | F | H | F | F | F | H |

*The radical $C_nH_{2n+1}$ is unbranched.

A further subject-matter according to the invention is a process for the preparation of pyran derivatives, in particular of the general formula I.

The process according to the invention is characterized in that it includes, as one process step, a ring-closing metathesis reaction of a compound of the general formula II

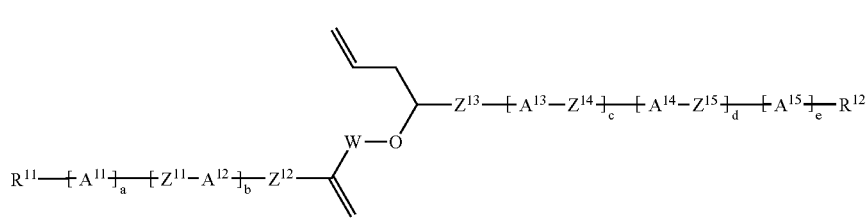

to give a pyran derivative of the formula I

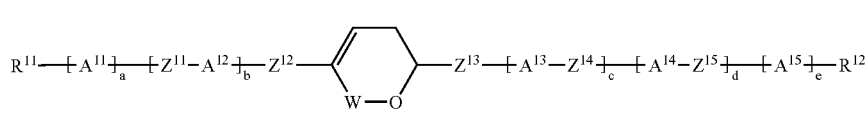

in the presence of a metathesis catalyst, where a, b, c, d, e, W, $R^{11}$, $R^{12}$, $Z^{11}$, $Z^{12}$, $Z^{13}$, $Z^{14}$, $Z^{15}$, $A^{11}$, $A^{12}$, $A^{13}$, $A^{14}$ and $A^{15}$ in the formulae I and II are as defined for the formula I above; with the proviso that, in the case of direct linking of $Z^{13}$ and $R^{12}$ to give $—Z^{13}—R^{12}$, $R^{12}$ is H, aralkyl or alkanyl if $Z^{13}$ is $—C(\!=\!O)—$, $R^{12}$ is aralkyl or alkanyl if $Z^{13}$ is $—C(\!=\!O)—O—$, and $Z^{13}$ is not $—CH_2O—$ or $—CF_2O—$; that, in the case of direct linking of $Z^{14}$ and $R^{12}$ to give $—Z^4—R^{12}$, $R^{12}$ is H, aralkyl or alkanyl if $Z^{14}$ is $—C(\!=\!O)—$, $R^{12}$ is aralkyl or alkanyl if $Z^{14}$ is $—C(\!=\!O)—O—$, and $Z^{14}$ is not $—CH_2O—$ or $—CF_2O—$; that, in the case of direct linking of $Z^{15}$ and $R^{12}$ to give $—Z^{15}—R^{12}$, $R^{12}$ is H, aralkyl or alkanyl if $Z^{15}$ is $—C(\!=\!O)—$, $R^{12}$ is aralkyl or alkanyl if $Z^{15}$ is $—C(\!=\!O)—O—$, and $Z^{15}$ is not $—CH_2O—$ or $—CF_2O—$; that $R^{11}$ is not H if a and b are both simultaneously zero and $Z^{12}$ is a single bond; that $R^{11}$ is not $CH_3$ if simultaneously a and b are both zero, $Z^{12}$ and $Z^{13}$ are each a single bond, W is $—CH_2—$ and $-[-A^{13}-Z^{14}-]_c-[-A^{14}-Z^{15}]_d-[-A^{15}-]_e-R^{12}$ is unsubstituted phenyl.

Metathesis reactions (frequently also known as olefin metathesis) for the synthesis of carbocyclic compounds (or of (poly)olefins from carbocyclic compounds) are well known in the prior art (see, inter alia, R. H. Grubbs and S. Chang, *Tetrahedron* 54 (1998) 4413; T. M. Trnka and R. H. Grubbs, *Acc. Chem. Res.* 2001, 34, 18; S. K. Armstrong, *J. Chem. Soc., Perkin Trans. I*, 1998, 371; A. Fürstner et al., *Chem. Eur. J.* 2001, 7, 3236, and the references cited therein). They can be used to form new C—C bonds and thus more complex molecules by simultaneous breaking and formation of unsaturated carbon-carbon bonds, in particular in the presence of selected metal-carbene complexes.

A distinction can be made here between various ring-closing and ring-opening metathesis reaction types. Besides ring-opening metathesis polymerisation (ROMP), which is of no further interest here, (intramolecular) ring-closing metathesis (RCM), cross metathesis (CM) and enyne metathesis (enyne), in particular, are of particular importance. The said metathesis types are illustrated in scheme 1 using the example of a hydrocarbon:

Scheme 1

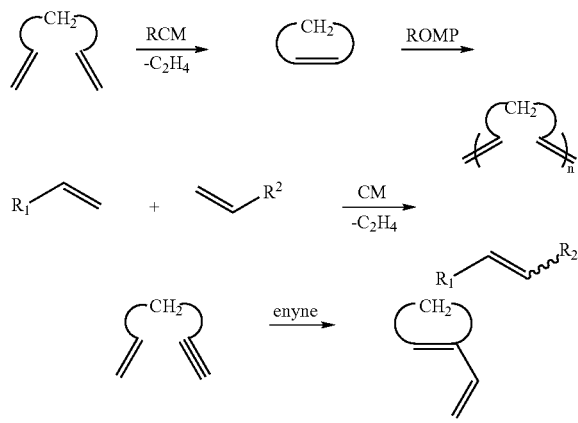

The metathesis reactions are preferably catalyzed by so-called Schrock (or Grubbs) carbene complexes (metal-alkylidene complexes) of transition metals, such as tungsten, molybdenum and in particular ruthenium. These complexes usually have a structure which can be reproduced by the following formula COMP-A (cf., inter alia, WO 96/04289, WO 97/06185, WO 99/00396 and WO 99/00397):

COMP-A

where Met is a transition metal, $(L)_x$ stands for a plurality of identical or different ligands, and $R_y$ is an organic radical, usually aryl, alkanyl or alkenyl.

The ring-closing metathesis reactions mentioned have also been employed to form heterocyclic ring systems and to prepare corresponding compounds. Thus, nitrogen heterocyclic compounds are accessible in large number by olefin metathesis. According to the literature, oxygen heterocyclic compounds can also be prepared with the aid of this synthetic methodology, but apparently in a significantly smaller structural breadth.

Thus, metathesis processes for the synthesis of pyran derivatives containing both an exocyclic substituent on a carbon atom of the endocyclic C=C double bond formed by metathesis and a 2,5-disubstituted

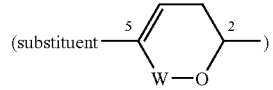

and having industrially useful properties and which can be used, for example, as mesogenic materials or as precursors for the preparation of other compounds having mesogenic properties which contain a pyran ring starting from readily accessible starting compounds have hitherto not been described in the prior art. This is possibly attributable to the fact that the ring-closure reaction to give O-heterocyclic compounds under metathesis conditions has, until the present invention, usually not succeeded or not succeeded reproducibly if one of the carbon atoms of one of the reacting C=C double bonds of the starting compound(s) is disubstituted (cf. also S. K. Armstrong, *J. Chem. Soc., Perkin Trans. I*, 1998, 371, in particular p. 376).

It is therefore particularly surprising that the ring-closing metathesis starting from compounds of the formula II in the presence of a metathesis catalyst leads reliably and efficiently to the pyran derivatives of the formula I according to the invention.

Preferred metathesis catalysts for the ring-closing metathesis are the transition-metal-alkylidene complexes of the general formula COMP-A described in the prior art (see, inter alia, R. H. Grubbs and S. Chang, *Tetrahedron* 54 (1998) 4413; T. M. Trnka and R. H. Grubbs, Acc. Chem. Res. 2001, 34, 18; S. K. Armstrong, *J. Chem. Soc., Perkin Trans. I*, 1998, 371; A. Fürstner et al., *Chem. Eur. J.* 2001, 7, 3236, and the references cited therein). This is preferably a complex of the formula COMP-A where Met=tungsten, molybdenum or ruthenium. Oxo-tungsten complexes of the trans-W(=O)Cl$_2$(aryl)$_2$ type (where aryl is preferably 2,6-dibromophenyl), which have been described, inter alia, by W. A Nugent et al., J. Am. Chem. Soc., 1995, 117, 8992, are furthermore used as metathesis catalysts in the processes according to the invention.

Preferred molybdenum metathesis catalysts are those of the formulae COMP-Mo1, COMP-Mo2, COMP-Mo3 and COMP-Mo4, while the formula COMP-W1 shows a preferred tungsten metathesis catalyst:

COMP-Mo1

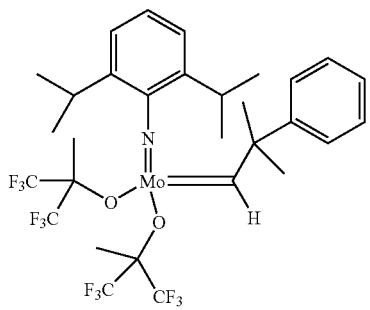

COMP-Mo2

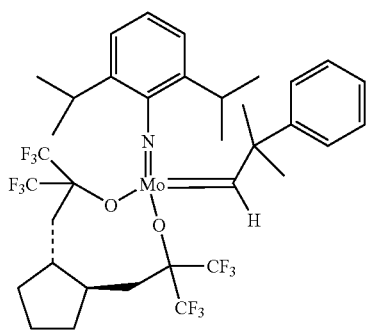

COMP-Mo3

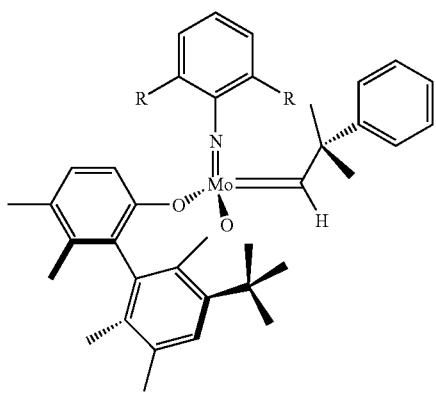

a: R = i-propyl
b: R = methyl
c: R = chlorine

COMP-Mo4

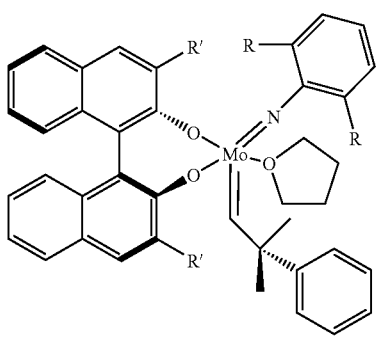

-continued

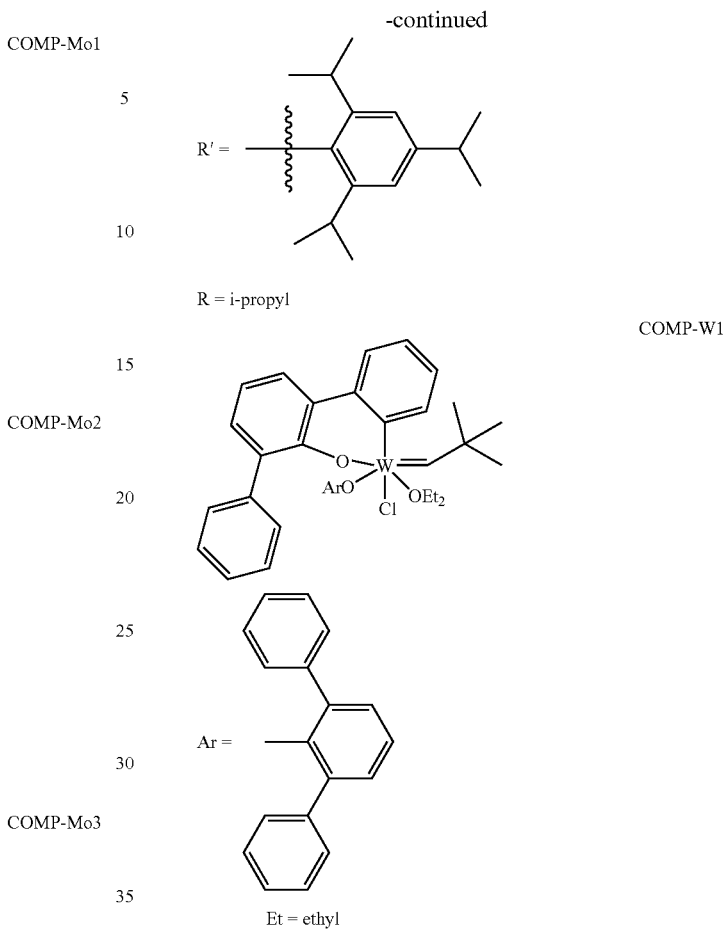

R = i-propyl

COMP-W1

Et = ethyl

Particularly preferred complexes for use as metathesis catalyst in the process according to the invention are ruthenium-alkylidene complexes of the COMP-RuA type, which are known per se from the literature (see, inter alia, WO 96/04289, WO 97/06185, WO 99/00396, WO 99/00397, WO 99/29701, WO 99/51344, WO 00/15339, EP 1 022 282 A2, WO 00/58322, WO 00/71554, WO 02/14336, WO 02/14376, WO 02/083742):

COMP-RuA

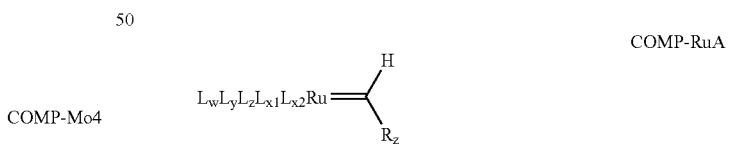

$L_{x1}$ and/or $L_{x2}$ here are preferably anionic ligands, preferably bromine, iodine or in particular chlorine, if desired also e-aralkyl, while $L_y$ and $L_z$ are preferably other, usually neutral ligands, such as, for example, $PPh_3$ (Ph=phenyl), $P(i-Pr)_3$ (i-Pr=isopropyl), $PCy_3$ (Cy=cyclohexyl), $P(Cp)_3$ (Cp=cyclopentadienyl), unsubstituted or substituted pyridyl, $Im^1$, $Im^2$ or alkoxy coordinated via the oxygen atom. $L_w$ is an optionally present ligand, i.e. w is 0 or 1, where this usually has the same meaning as $L_{x1}$, $L_{x2}$, $L_y$ and/or $L_z$. $R_z$ is an organic radical, in particular aryl, alkanyl or alkenyl.

Im¹

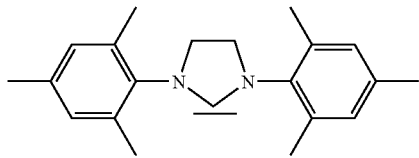

Im²

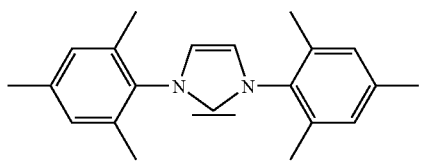

These ruthenium complexes are generally less sensitive to atmospheric oxygen and tolerate both traces of moisture and also slight impurities. Of the ruthenium-alkylidene complexes COMP-RuA, those of the following formulae COMP-Ru1 to COMP-Ru13 may be mentioned by way of example:

COMP-Ru1

[structure]

a: R = H
b: R = 3-Br
c: R = 4-phenyl

COMP-Ru2

[structure]

a: R = Cy
b: R = phenyl
c: R = p-CF₃—phenyl

COMP-Ru3

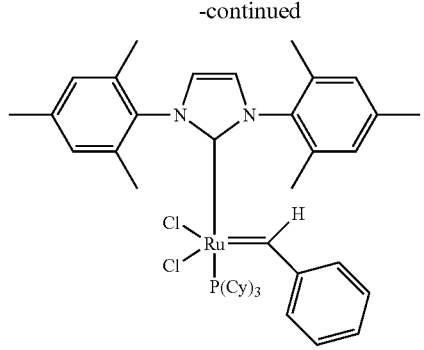

COMP-Ru4

COMP-Ru5

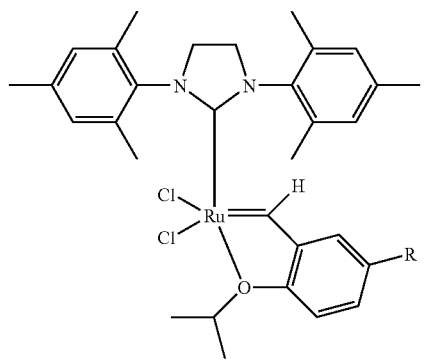

a: R = H
b: R = Br
c: R = NO₂

COMP-Ru6

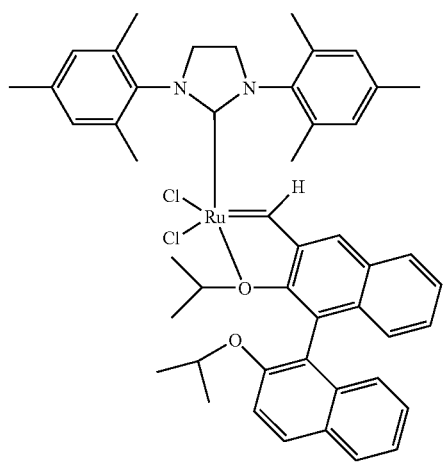

-continued

COMP-Ru7

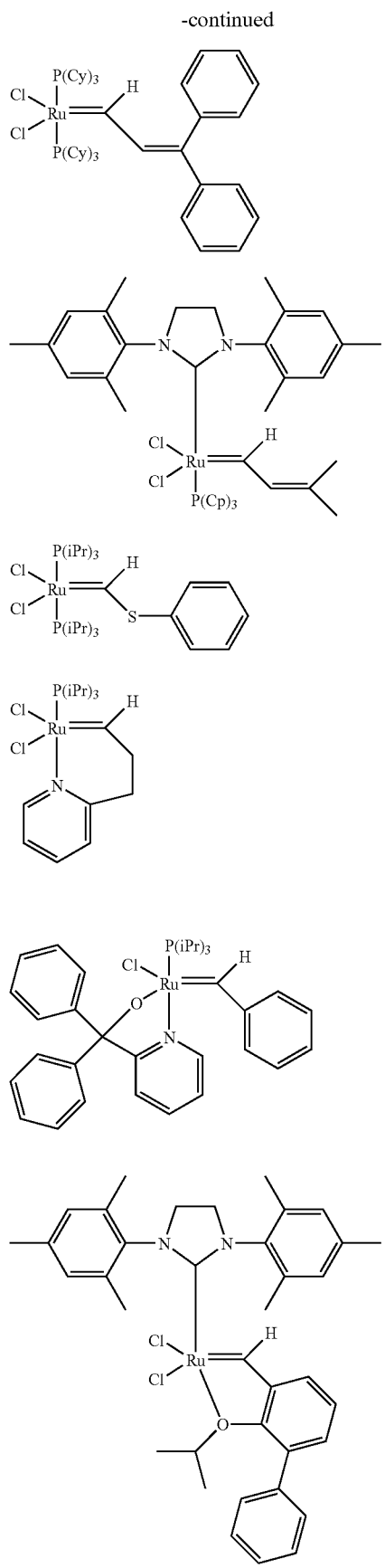

COMP-Ru8

COMP-Ru9

COMP-Ru10

COMP-Ru11

COMP-Ru12

-continued

COMP-Ru13

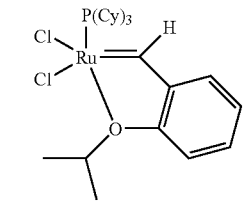

The alkylidene complexes employed as metathesis catalysts are either prepared by processes known from the literature (besides WO 96/04289, WO 97/06185, WO 99/00396, WO 99/00397, WO 99/29701, WO 99/51344, WO 00/15339, EP 1 022 282 A2, WO 00/58322, WO 00/71554, WO 02/14336, WO 02/14376, WO 02/083742, see, inter alia, also R. H. Grubbs and S. Chang, *Tetrahedron* 54 (1998) 4413; T. M. Trnka and R. H. Grubbs, Acc. Chem. Res. 2001, 34, 18; S. K. Armstrong, *J. Chem. Soc., Perkin Trans. I,* 1998, 371; A. Fürstner et al., *Chem. Eur. J.* 2001, 7, 3236; J. A. Love et al., Angew. Chem. 2002, 114, 4207; K. Grela et al., Angew. Chem. 2002, 114, 4210; G. S. Weatherhead et al., Tetrahedron Lett. 41 (2000) 9553; J. S. Kingsbury et al., J. Am. Chem. Soc. 1999, 121, 791, and the references indicated therein) or are commercially available, for example from Sigma-Aldrich, Inc. (USA), or Strem Chemicals Inc. (Kehl, Germany).

Some of these catalysts can also be attached to immobilising supports, for example made from polystyrene (for example COMP-Ru3: M. Ahmed et al., Synlett 2000, 1007; or COMP-Ru5a and complexes derived therefrom: St. Randl et al., Synlett 2001, 1547) or glass (for example COMP-Ru5 and complexes derived therefrom: J. S. Kingsbury et al., Angew. Chem. 2001, 113, 4381).

Apart from the above-mentioned molybdenum and tungsten complexes, the catalyst used for the ring-closing metathesis step of the process according to the invention is very particularly preferably a metal complex selected from the group consisting of complexes of the formulae COMP-Ru1, -Ru2, -Ru3, -Ru4, -Ru5, -Ru6, -Ru7, -Ru8, -Ru9, -Ru10, -Ru11, -Ru12 and -Ru13, in particular of the formulae COMP-Ru2a, -Ru3, -Ru5a, -Ru6, -Ru11 and -Ru13. The molar ratio of compound of the formula II to catalyst is generally from 0.001 to 20 mol % (based on the compound of the formula II), preferably from 0.01 to 10 mol %, very particularly preferably from 0.01 to 2 mol % and in particular from 0.01 mol %, to 0.1 mol %.

The ring-closing metathesis of the process according to the invention is carried out under conventional conditions for metal complex-catalyzed reactions of this type. The reaction is carried out without a solvent or in a suitable solvent. The solvent used is an inert solvent, preferably an aromatic and/or halogenated organic solvent and in particular toluene, benzene, chlorobenzene or dichloromethane. The reaction is generally carried out at temperatures from room temperature to the boiling point of the solvent (for example from about 20° C. to 40° C. (dichloromethane) or up to 80° C. or 110° C. (toluene)). The reaction temperature is preferably from 40° C. to 60° C. The reaction time is not crucial per se since the metathesis reaction generally proceeds with complete conversion of the starting material of the formula II and gives the desired pyran derivative of the formula I in good yields. The reaction duration is usually from 10 minutes to 2 days, preferably from 1 hour to 24 hours, in particular from 2 hours to 8 hours.

It is furthermore advantageous to add the catalyst to the reaction mixture in portions, which allows better control of the reaction and results in a reduction in the total amount of catalyst.

In a preferred embodiment of the process according to the invention, compounds of the formula I-A (i.e. compounds of the formula I where W=—C(=O)—) in which $Z^{13}$, $Z^{14}$ and $Z^{15}$ are not —C(O)— are subjected to a reduction reaction for conversion into a pyran derivative of the formula I in which W is a methylene group (i.e. a pyran derivative of the formula I-B) in a further reaction step after the metathesis reaction step according to the invention. This reduction reaction can be carried out using suitable reducing agents, for example diisobutylaluminium hydride (DIBAH) or boron trifluoride etherate+lithium aluminium hydride or lithium borohydride or sodium borohydride (see J. March: Advanced Organic Chemistry; John Wiley & Sons, New York inter alia, 3rd Edn., 1985, p. 1100, 9-41). Other carboxyl functions (C(=O)O) present in the molecule are also reduced to ether functions (CH$_2$O) at the same time.

A further preferred embodiment of the process according to the invention includes, as a further reaction step taking place before the ring-closing metathesis step, the reaction of an acrylic compound or allyl compound of the formula IV with a homoallyl compound of the formula V with formation of the compound of the formula II tion step according to the invention is generally carried out under the conditions of the Williamson ether synthesis (see, for example, J. March: Advanced Organic Chemistry; John Wiley & Sons, New York inter alia, 3rd Edn., 1985, p. 342, 0-14), i.e. under basic reaction conditions and at temperatures from room temperature to about 60° C. in suitable solvents, for example ethers, such as tetrahydrofuran (THF), methyl tert-butyl ether (MTBE), dioxane or dimethoxyethane. A particularly preferred variant of this reaction works with granulated NaOH in THF in the presence of a phase-transfer catalyst and a little water, with the allyl compound of the formula IV-B where $X^{11}$=bromine or chlorine and the homoallyl alcohol of the formula V being warmed at from 40° C. to 60° C. for from 4 to 48 hours. This variant is particularly suitable for homoallyl alcohols of the formula V which do not contain a carboxyl function (i.e. homoallyl alcohols of the formula V in which $Z^{13}$, $Z^{14}$ and $Z^{15}$ are not $CO_2$). Alternatively, the base employed can be sodium hydride, preferably in an organic solvent.

The acrylic compounds or allyl compounds of the formula IV and homoallyl compounds of the formula V employed in the process according to the invention are—if they are known from the literature—either commercially available or are prepared by methods known per se, as described in the literature (for example the standard works, such as Houben-Weyl, Methoden der Organischen Chemie [Methods of Organic

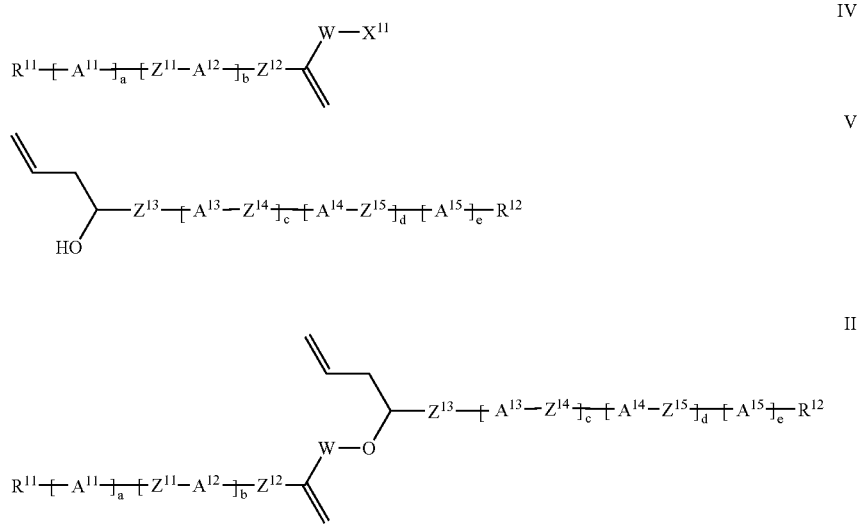

where $X^{11}$ is a leaving group, and a, b, c, d, e, W. $R^{11}$, $R^{12}$, $Z^{11}$, $Z^{12}$, $Z^{13}$, $Z^{14}$, $Z^{15}$, $A^{11}$, $A^{12}$, $A^{13}$, $A^{14}$ and $A^{15}$ in the formulae II, IV and V are as defined for the formula I above.

If W is —C(=O)— (i.e. the compound of the formula IV is an acrylic derivative (formula IV-A)), $X^{11}$ is preferably methoxy, ethoxy, propoxy, t-butoxy, chlorine, bromine or an anhydride radical, in particular acetoxy. The process step then proceeds under the usual conditions for ester formation reactions of this type (cf., inter alia, J. March: Advanced Organic Chemistry; John Wiley & Sons, New York inter alia, 3rd Edn., 1985, pp. 346-351, 0-22, 0-23 and 0-24).

W is preferably —CH$_2$— (i.e. the compound of the formula IV is an allyl derivative (formula IV-B)). In this case, $X^{11}$ is preferably chlorine, bromine, iodine or a sulfonic acid radical, for example $CF_3$—$SO_3$—, $CH_3$—$SO_3$—, $C_4F_9$—$SO_3$— or p-$CH_3$—$C_6H_4$—$SO_3$—. The ether formation reac- Chemistry], Georg-Thieme-Verlag, Stuttgart), to be precise under reaction conditions which are known and suitable for the reactions mentioned therein. Use can also be made here of variants which are known per se, but are not mentioned here in greater detail.

The allyl compounds of the formula IV-Ba where a=b=0 can be obtained, inter alia, via the allyl alcohols of the formula IV-Ba1, which are accessible in accordance with a Weigand and Brückner process (S. Weigand, R. Brückner, Synthesis 1996, 475) as shown in scheme 2. The conversion of formula IV-Ba1 into the allyl compounds of the formula IV-Ba2 is carried out by known processes, for example using bromine/triphenylphosphine for $X^{11}$=Br and by means of trifluoromethanesulfonyl chloride or trifluoromethanesulfonic anhydride for $X^{11}$=$CF_3SO_3$.

Scheme 2

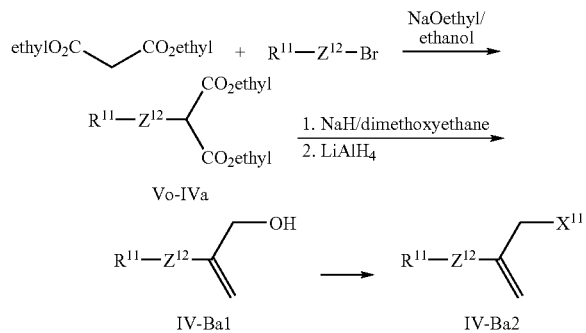

The synthesis of the allyl derivatives of the formula IV-Bb where a and/or b are 1, which were hitherto unknown, is carried out analogously and is shown in scheme 3:

Scheme 3

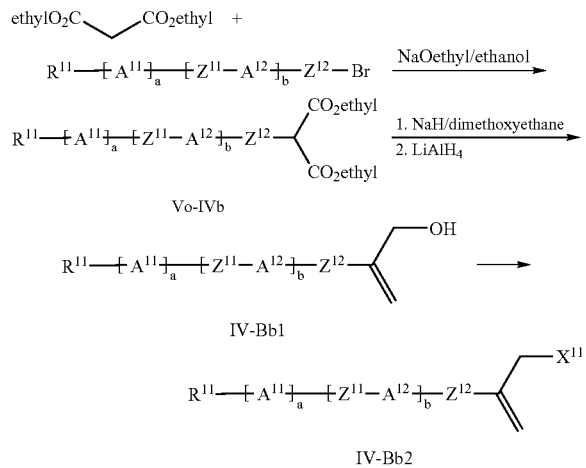

Instead of the substituted malonic acid diesters Vo-IVa or Vo-IVb, the allyl derivatives of the formula IV-B can also be prepared using the corresponding diols of the formula Vo-IVc, which are known from the literature or are accessible analogously to known processes (see, inter alia, P. Kirsch and E. Poetsch, Adv. Mater. 1998, 10, 602, and the references indicated therein; C. Tschierske et al., Mol. Cryst. Liq. Cryst. 1990, 191, 295; EP 400 846 A1). The precursor Vo-IVc gives, for example after dihalogenation and treatment with 1 equivalent of potassium tert-butoxide, the allyl compound IV-B where $X^{11}$=halogen.

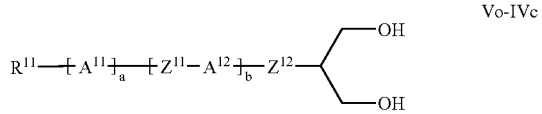

The allyl alcohols of the formulae IV-Ba1 and IV-Ba2 are also accessible analogously to a process of H. Mitzutani et al. (Tetrahedron 58 (2002) 8929) from the corresponding acrolein derivatives with $NaBH_4/CeCl_3$; the acrolein derivatives are themselves obtained from the corresponding aldehyde $R^{11}$—$Z^{12}$—$CH_2$—CHO or $R^{11}$-[-$A^{11}$]$_a$-[-$Z^{11}$-$A^{12}$-]$_b$-$Z^{12}$—$CH_2$—CHO using Eschenmoser's reagent.

The novel allyl derivatives of the formula IV-Bb

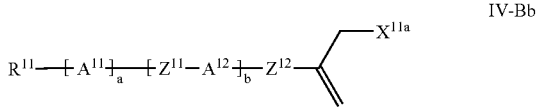

where a is zero and b is 1 or a is 1 and b is zero or a and b are both 1;
$X^{11a}$ is chlorine, bromine, iodine, a sulfonic acid radical, —OH, alkoxy or O-aralkyl, or $X^{11a}$ is =O;
$R^{11}$, $Z^{11}$ and $Z^{12}$ are as defined for the formula I above; and
$A^{11}$ and $A^{12}$ are as defined for the formula I above and are preferably 1,4-cyclohexylene;

are likewise a subject-matter of the present invention as useful intermediates for the preparation of the compounds of the formula I according to the invention. They are prepared as described above and in the attached examples; the compounds of the formula IV-Bb where $X^{11a}$=alkoxy or O-aralkyl are accessible, inter alia, by reaction of the corresponding compounds of the formula IV-Bb where $X^{11a}$=Cl, Br, I or a sulfonic acid radical with a corresponding alcohol (alkyl-O—H or aralkyl-O—H). The aldehydes of the formula IV-Bb (where —$X^{11a}$ is =O) according to the invention are also accessible from the allyl alcohols of the formula IV-Bb (where $X^{11a}$ is —OH) by mild oxidation using, for example, manganese dioxide.

The corresponding acrylic derivatives of the formula IV-A are accessible, inter alia, by oxidation of the corresponding allyl alcohols of the formula IV-Ba1 or IV-Bb1 using a strong oxidant, such as a chromium(VI) oxidant (J. March: Advanced Organic Chemistry; John Wiley & Sons, New York inter alia, 3rd Edn., 1985, p. 1084, 9-22). Alternatively, the allyl alcohols may also firstly be converted into the corresponding aldehydes (acrolein derivatives) using a relatively mild oxidant, such as manganese dioxide ($MnO_2$), which are then converted into the acrylic derivatives of the formula IV-A, for example using an alkaline $Ag_2O$ or silver nitrate solution or by means of atmospheric oxygen.

The homoallyl compounds of the formula V are accessible as shown in scheme 4 by reaction of aldehydes of the formula Vo-Va with allyl bromide (it also being possible to use other allyl halides, in particular allyl chloride, instead of the bromide):

Scheme 4

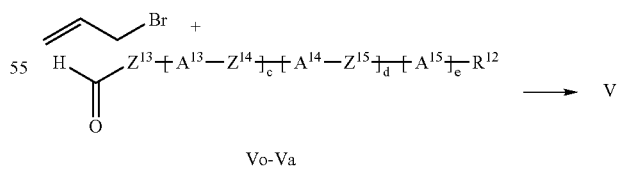

The requisite activation of the allyl halide can be carried out in various ways: for example, addition of allyl bromide to indium powder in a suitable reaction medium, for example water or water/tetrahydrofuran, firstly forms a corresponding intermediate allylindium compound (by the method of T.-P. Loh et al., Tetrahedron Letters 42 (2001) 8701 and 8705) which then reacts with the aldehyde Vo-Va with formation of the corresponding homoallyl alcohol V. Allyl bromide can also be converted into the corresponding intermediate allyllithium or allylmagnesium bromide compound using lithium or an organolithium base or using magnesium, usually in excess, or a reactive Grignard base with halogen-metal exchange, and this intermediate then reacts with the aldehyde Vo-Va to give the homoallyl alcohol V. If the aldehyde Vo-Va additionally contains an ester or nitrile function, it is advantageous to transmetallate the intermediate allyllithium or allylmagnesium bromide compound in a known manner using zinc or titanium salts, since the corresponding allylzinc or allyltitanium compounds only react chemoselectively with the aldehydic carbonyl function and not with the ester carboxyl or the nitrile function.

It is furthermore also possible to employ allyl derivatives of other metals and semimetals, for example allyl derivatives of chromium, tin, zinc, samarium, boron and silicon, for the preparation of the homoallyl compounds V. Starting from allyl mesylate (bromine in allyl bromide is replaced by a mesylate radical (—OSO$_2$CH$_3$)), the corresponding allyl stannanes are accessible by transmetallation using, for example, LiSn(butyl)$_3$, and can also be prepared by reaction of allyl bromide with tin(II) chloride and potassium iodide in water (cf. V. V. Samoshin et al., Tetrahedron Lett. 43 (2002) 6329) or with tin metal under the action of ultrasound and water (cf. P. C. Andrews, Tetrahedron Lett. 43 (2002) 7541) and can be reacted with the aldehyde Vo-V to give the homoallyl alcohol V.

Correspondingly, the allylzinc compound is obtainable, inter alia, using zinc dust in tetrahydrofuran (cf. B. C. Ranu et al., Tetrahedron Lett. 36 (1995), 4885), the allylsamarium compound is obtainable using SmI$_2$ in tetrahydrofuran (cf. B. Hamann-Gaudinet et al., Tetrahedron Lett. 38 (1997) 6585) or the allylchromium compound, which can be reacted with an aldehyde Vo-V to give homoallyl alcohols V, is obtainable using Cr(II)Cl$_2$/Mn.

Since the aldehydes of the formula Vo-V have a prochiral center on the carbonyl carbon atom, a center of chirality is formed on the carbon atom carrying the hydroxyl function in the reaction with the activated allyl derivative formed from allyl bromide to give the homoallyl alcohol V. In general, a racemate of the optical antipodes of the homoallyl alcohol V forms in the process. However, it is also possible to prepare one of the optical isomers of the homoallyl alcohol V stereoselectively or alternatively to isolate it from the racemic mixture.

The stereoselective synthesis is preferably carried out by catalytic asymmetric allylation of the aldehyde of the formula Vo-V using an allyltin compound, usually allyltributylstannane, in the presence of a chiral catalyst. Suitable chiral catalysts are, in particular, complexes of chiral binaphthol (BINOL) compounds with zirconium (for example (R,R)- or (S,S)-BINOL-Zr(O-tert-butyl)$_4$: M. Kurosu et al., Tetrahedron Lett. 43 (2002) 1765) or titanium (for example bis(((S)(naphthoxy)(isopropoxy)titanium oxide: H. Hanawa et al., J. Am. Chem. Soc. 2003, 125, 1708) or corresponding boronates (cf., for example, S. Thormeier et al., J. Organomet. Chem. 657 (2002) 136). In principle, the R- or S-isomer is accessible selectively in this way—depending on the choice of the chiral catalyst.

The enantiomers are isolated from the racemic mixture by conventional methods, for example by crystallization with a chiral base or chromatography on a chiral column material.

Through use of an enantiomerically pure homoallyl alcohol of the formula V accessible in this way, the corresponding pyran derivative of the formula I, which has a center of asymmetry in the 2-position, is obtained in enantiomerically pure form via the intermediate II after the ring-closing metathesis reaction according to the invention. A further possibility for obtaining one of the optical antipodes of the pyran derivative of the formula I stereoselectively consists in the use of a chiral metathesis catalyst, for example COMP-Mo3 or COMP-Mo4 (G. S. Weatherhead et al., Tetrahedron Lett. 41 (2000) 9553).

Aldehydes of the formula Vo-Va are known as such from the literature (see, inter alia, EP 0 122 389 A2) or can be prepared analogously thereto. Aldehydes of the formula Vo-Va where $Z^{13}$=CF$_2$O are synthesised, for example, starting from the acid chloride

ethyl-O—C(=O)—C(=O)—Cl     Vo-Vb by reaction with firstly NaS—(CH$_2$)$_3$—SH. The resultant thiol thioester is reacted with trifluoromethanesulfonic acid (analogously to the processes described by P. Kirsch et al., Angew. Chem. 2001, 113, 1528, and WO 01/64667) to give the corresponding bis(alkylthio)carbenium salt

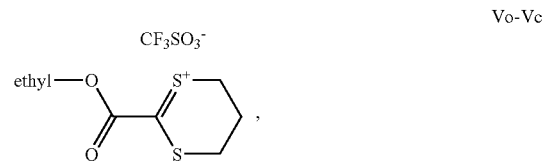

Vo-Vc which is then subjected to oxidative fluorodesulfuration (as described by P. Kirsch et al., Angew. Chem. 2001, 113, 1528, and WO 01/64667) by reacting the bis(alkylthio)carbenium salt of the formula Vo-Vc firstly at low temperatures with NEt$_3$.3 HF (Et=ethyl) and an alcohol of the formula

HO-[A$^{13}$-Z$^{14}$]$_c$-[A$^{14}$-Z$^{15}$]$_d$-[A$^{15}$]$_e$-R$^{12}$     Vo-Vd, then with 1,3-dibromo-5,5-dimethylhydantoin (DBH) or N-bromosuccinimide (NBS) or bromine and finally with aqueous caustic lye to give the ester

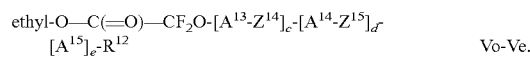

ethyl-O—C(=O)—CF$_2$O-[A$^{13}$-Z$^{14}$]$_c$-[A$^{14}$-Z$^{15}$]$_d$-
    [A$^{15}$]$_e$-R$^{12}$     Vo-Ve.

The final introduction of the aldehyde function to give the aldehyde of the formula Vo-Va is carried out either by direct reduction of the ester using a suitable reducing agent, such as diisobutylaluminium hydride, in an inert solvent, for example methylene chloride, or via reduction of the ester to give the corresponding alcohol and subsequent oxidation to the aldehyde using a suitable oxidant, for example Dess-Martin reagent.

An alternative synthetic route which is suitable, in particular, for the preparation of aldehydes of the formula Vo-Va in which the difluorooxymethylene bridge is linked to an aromatic radical starts from the ester ethyl-O—C(=O)—CF$_2$Br, which is converted into the desired aldehyde Vo-Va using a suitable phenoxide in the presence of, for example, hexamethylenephosphoric tribromide or with Pd$^0$ complex catalysis with formation of the CF$_2$O bridge and after final reduction of the ester function.

If the aldehyde of the formula V-IV is a phenanthrene derivative of the formula

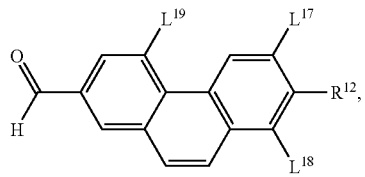

this is accessible in accordance with scheme 5 below:

Scheme 5

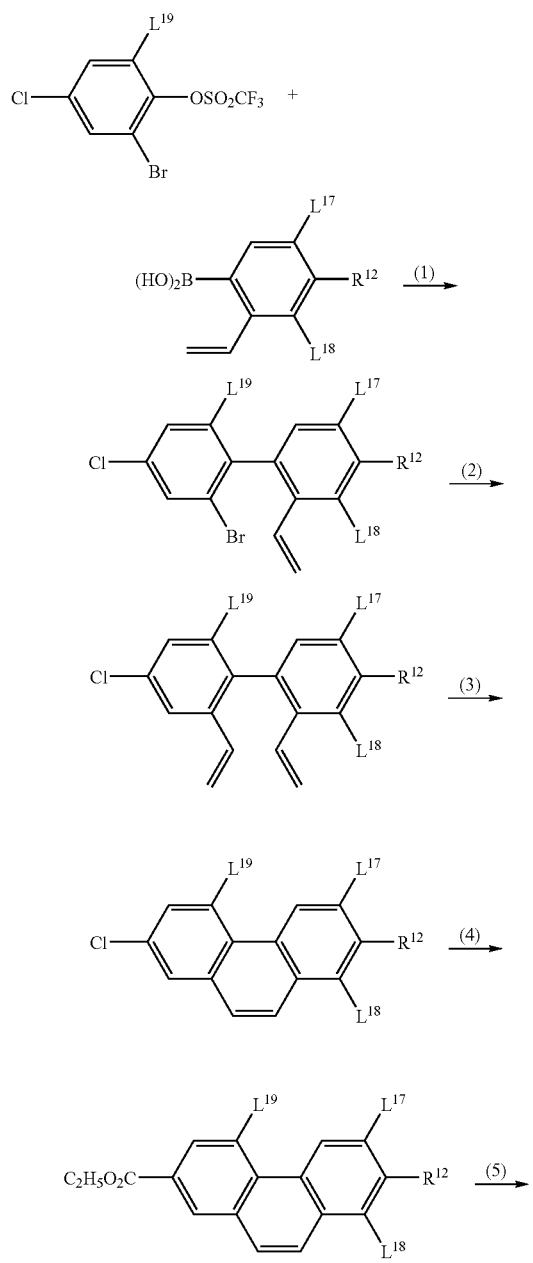

In step (1), C—C coupling is carried out with Pd⁰ catalysis to give the biphenyl, which is converted into the divinyl derivative in step (2) using vinylmagnesium bromide or vinylzinc bromide in the presence of a palladium complex ($PdCl_2$.bis-(diphenylphosphino)ferrocene). In step (3), an intramolecular cross metathesis to give the phenanthrene derivative is carried out in the presence of a ruthenium-alkylidene complex COMP-RuA, preferably COMP-Ru2a-c or COMP-Ru4. The chlorophenanthrene is subsequently converted into the ethyl ester in step (4) using CO/ethanol at 70° C. and 5 bar in the presence of $PdCl_2.[2P(cyclohexyl)_3]$ as catalyst, and this ethyl ester gives the desired phenanthrene aldehyde after final reduction using DIBAH in step (5).

For the preparation of the phenanthrene aldehyde of the formula

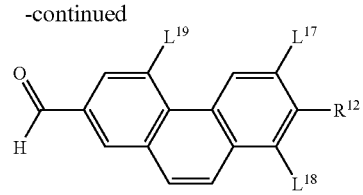

the chlorine-substituted compound in step (1) of scheme 5 is replaced by the corresponding benzyloxy compound

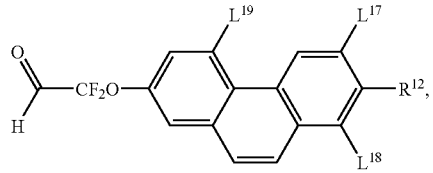

which is correspondingly converted into the corresponding benzyloxy-substituted phenanthrene compound in steps (1) to (4). After reductive removal of the benzyloxy protecting group (using hydrogen and Pd/C), the resultant hydroxyphenanthrene is converted into the desired aldehyde as described above using ethyl-O—C(=O)—$CF_2$Br and after final reduction of the ester function. The starting compounds for these phenanthrene syntheses are either commercially available or readily accessible by known synthetic methods.

The starting compounds necessary for the preparation of compounds of the formula I-G according to the invention by the process according to the invention by ring-closing metathesis reaction are also accessible by a further process which is illustrated in scheme 6:

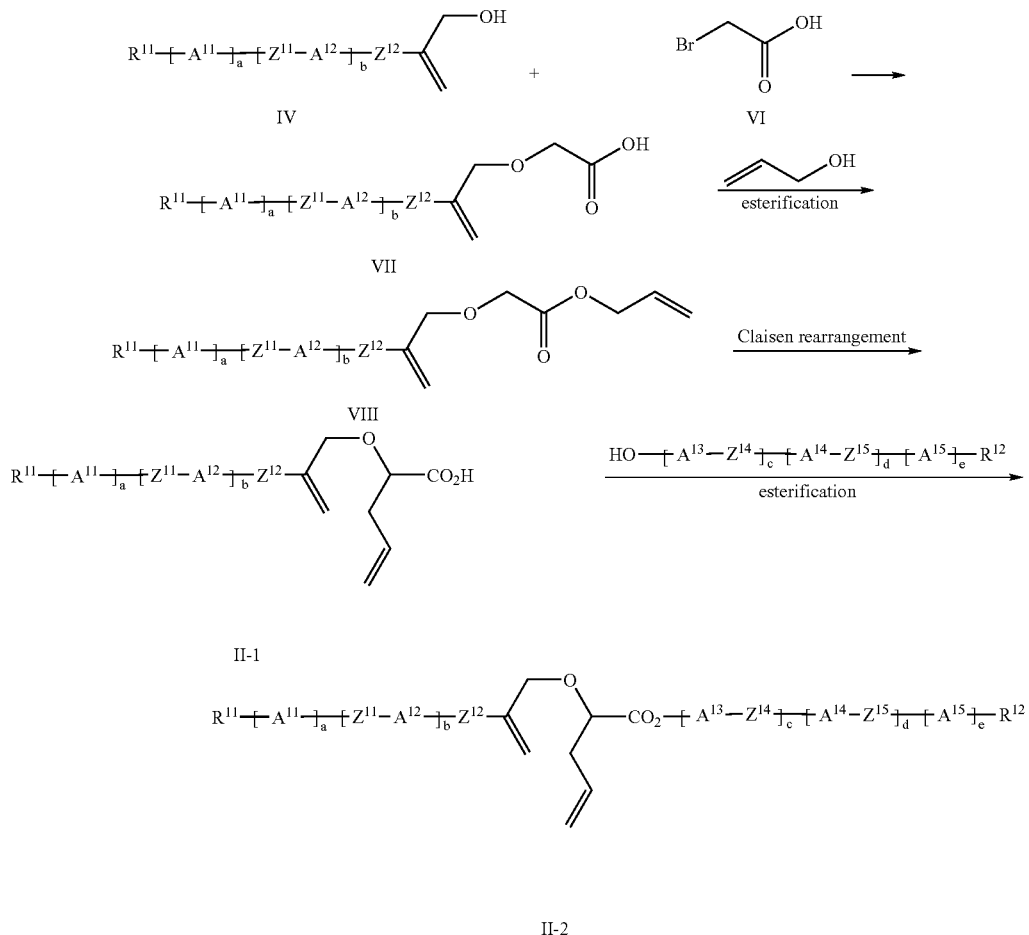

Scheme 6

In this process, firstly the acid VII is prepared, for example, from the allyl alcohol IV and bromoacetic acid VI (as described, for example, in J. March: Advanced Organic Chemistry; John Wiley & Sons, New York inter alia, 3rd Edn., 1985, p. 342, 0-14), and subsequently converted into the compound VIII using allyl alcohol under conventional conditions (cf., inter alia, J. March: Advanced Organic Chemistry; John Wiley & Sons, New York inter alia, 3rd Edn., 1985, pp. 346-351, 0-22, 0-23 and 0-24).

This is subsequently subjected to a Claisen rearrangement (see, for example, J. March: Advanced Organic Chemistry; John Wiley & Sons, New York inter alia, 3rd Edn., 1985, p. 1028, 8-37), for example by firstly adding lithium diisopropylamide (LDA) and then a 1:1 mixture of trimethylsilyl chloride and triethylamine to a solution of VIII in THF at very low temperatures (about −100° C.), slowly thawing the mixture, adding aqueous base or acid, and subjecting the mixture to conventional work-up to give the acid II-1. The ring-closing metathesis reaction according to the invention is preferably carried out using an ester II-2 instead of the free carboxylic acid II-1, this ester being prepared by conventional esterification methods and giving, after the metathesis reaction, the compounds of the formula I-G according to the invention.

It goes without saying that firstly precursors and starting compounds of the formulae II, IV and V for compounds of the formula I according to the invention can be prepared from other suitable precursors and starting compounds of the formulae II, IV and V, and secondly compounds of the formula I according to the invention can also be converted, after the ring closure, into other pyran derivatives of the formula I according to the invention. Carboxylic acid, benzyloxy and halogen derivatives have proven particularly useful here.

Thus, for example, the carboxylic acid ester of the formula II-2 (where $c=d=e=0$ and $R^{12}$ is aralkyl, alkanyl or alkenyl) can firstly be subjected to a ring-closing metathesis reaction with formation of the corresponding pyran derivative of the formula I-G (where $c=d=e=0$ and $R^{12}$ is aralkyl, alkanyl or alkenyl). Transesterification of this ester with synthetic units of the HO-$[A^{13}$-$Z^{14}]_c$-$[A^{14}$-$Z^{15}]_d$-$[A^{15}]_e$-$R^{12}$ type then enables other compounds of the formula I-G according to the invention to be obtained. However, a corresponding esterification can also, if desired, be carried out with precursor II-1 before the ring-closing metathesis reaction.

The carboxylic acids of the formula I-G according to the invention (where $R^{12}=H$ and $c=d=e=0$), which are prepared from the corresponding esters by basic or acidic saponification, can be employed in order to obtain the corresponding $CF_2O$-bridged pyran derivative of the formula I-H via the corresponding bis(alkylthio)carbenium salt followed by oxidative fluorodesulfuration (cf. WO 01/64667). The oxidative fluorodesulfuration can of course also be used for compounds of the formula I according to the invention in which the carboxyl function is not linked directly to the central pyran ring, i.e. if $Z^{14}$ or $Z^{15}$=—$CO_2H$; in this way, —$CF_2O$-[$A^{14}$-$Z^{15}$]$_d$-[$A^{15}$]$_e$-$R^{12}$— or —$CF_2O$-$A^{15}$-$R^{12}$— radicals respectively are then introduced.

Aldehydes of the formula I according to the invention where $Z^{13}$—$R^{12}$=—C(=O)—H are accessible from the carboxylic acid esters of the formula I-G according to the invention where $R^{12}$≈H and c=d=e=0 either by direct reduction, for example using a suitable metal hydride, or in two steps by reduction to the primary alcohol followed by gentle oxidation using, for example, Dess-Martin reagent. The reduction to pyran derivatives according to the invention containing an aldehyde function can of course also be carried out with compounds of the formula I in which the carboxylic acid ester function is not linked directly to the central pyran ring, i.e. if $Z^{14}$ or $Z^{15}$=—$CO_2R^{12}$. In this way, the —C(=O)—H function is introduced as radical $Z^{14}$—$R^{12}$ or $Z^{15}$—$R^{12}$.

The corresponding compounds of the formula I according to the invention where $Z^{13}$, $Z^{14}$ or $Z^{15}$=—CH=CH— are accessible from the aldehydes of the formula I accessible in this way, for example by means of a Wittig or Wittig-Horner reaction with molecules of the $R^x$-[$A^{13}$-$Z^{14}$]$_c$-[$A^{14}$-$Z^{15}$]$_d$-[$A^{15}$]$_e$-$R^{12}$ type (where $R^x$ is, for example, (phenyl)$_3$P=CH— or (ethyl-O)$_2$P(=O)—$CH_2$—).

The ketones of the formula I according to the invention where $Z^{13}$—$R^{12}$, $Z^{14}$—$R^{12}$ or $Z^{15}$—$R^{12}$=—C(O)—$R^{12}$ and $R^{12}$=alkanyl, alkenyl or aralkyl are prepared, for example, by reaction of the corresponding carboxylic acid ester of the formula I-G with a suitable organometallic reagent, for example with a compound $R^{12}$—Mg—Br by the Grignard method (see, for example, J. March: Advanced Organic Chemistry, John Wiley & Sons, New York inter alia, 3rd Edn., 1985, p. 434, 0-107). Further ketones of the formula I where, for example, $Z^{13}$-[$A^{13}$-$Z^{14}$]$_c$-[$A^{13}$-$Z^{15}$]$_d$-[$A^{15}$]$_e$-$R^{12}$ is —C(O)-[$A^{13}$-$Z^{14}$]$_c$-[$A^{14}$-$Z^{15}$]$_d$-[$A^{15}$]$_e$-$R^{12}$ are also accessible analogously by reaction with a suitable organometallic reagent Met*-[$A^{13}$-$Z^{14}$]$_c$-[$A^{14}$-$Z^{15}$]$_d$-[$A^{15}$]$_e$-$R^{12}$ (where "Met*" is, for example, Br—Mg or Li). If $Z^{14}$ and $Z^{15}$ are not $CO_2$ and $R^{12}$ does not contain a carboxyl function, the ketones of the formula I are obtainable by reduction of the corresponding esters of the formula I-G. Keto functions can also be introduced analogously as $Z^{14}$ or $Z^{15}$.

Compounds of the formula I-K according to the invention are also highly suitable for further derivatisations. Reaction on the cyclohexanone ring with, for example, trimethylsilyl-1,3-dithiane in THF in the presence of n-butyllithium (in accordance with the method of J. Mlynarski and A. Banaszek, Tetrahedron 55 (1999) 2785) or analogously to the processes of P. Kirsch et al., Angew. Chem. 2001, 113, 1528, gives the corresponding ketene dithioketals (containing the structural unit

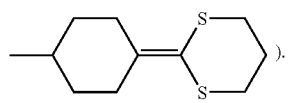

).

Oxidative fluorodesulfuration (by the method of P. Kirsch et al., Angew. Chem. 2001, 113, 1528) then gives compounds of the formula I according to the invention containing

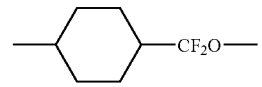

as structural unit.

The cyclohexanones of the formula I-K according to the invention can also be reacted with a suitable Grignard reagent, for example of the Br—Mg—$Z^{14}$-$A^{14}$-$R^{12}$ type where $Z^{14}$ is, for example, —$CH_2$— or —$CH_2CH_2$—, to give the corresponding tertiary alcohols, in this example containing the structural unit

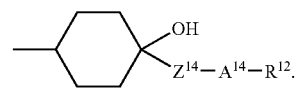

Subsequent reduction of the alcohol using triethylsilane and boron trifluoride etherate gives the corresponding 1,4-disubstituted cyclohexane derivative (in the example mentioned containing the structural unit

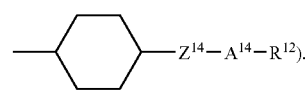

Compounds of the formula I according to the invention which contain a terminal phenyl ring where $R^{12}$=halogen, in particular bromine or iodine, for example corresponding compounds of the formula I-CBI, I-CBII, I-CBIIIc, I-GII, I-GIII, I-HI, I-HII or I-J, can likewise be employed as starting compounds for the preparation of further compounds of the formula I according to the invention. Thus—after metallation with metal-halogen exchange, for example using an organometallic base, such as n-butyl-lithium—the intermediate metallated compound can be reacted further with various reagents, for example with $CO_2$ with formation of the corresponding carboxylic acid, with boric acid esters or related boron compounds with formation of the corresponding arylboron compounds, or in the presence of suitable catalysts with reactants which undergo C—C cross-coupling reactions, for example of the Heck or Suzuki reaction type.

The said arylboron compounds or the halogenated compounds themselves can also be reacted in cross-coupling reactions of this type which are known from the literature (see, for example, N. Miyaura, A. Suzuki, Chem. Rev. 1995, 95, 2457). It should furthermore be noted that certain precursors and starting compounds of the processes according to the invention, for example those in which an aromatic ring $A^{13}$ is linked directly to an aromatic ring $A^{14}$ (or $A^{15}$) via $Z^{14}$ (or $Z^{15}$)=single bond, can also be prepared with the aid of these cross-coupling reactions.

It is furthermore preferred in the process according to the invention, after the ring-closing metathesis reaction step, to carry out, as a further reaction step, a catalytic hydrogenation to give a pyran derivative of the general formula III:

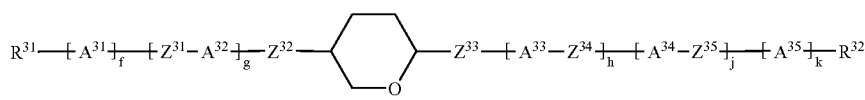

III in which f, g, h, j and k are each, independently of one another, 0 or 1;

$R^{31}$ is H, an alkyl radical having from 1 to 15 carbon atoms which is unsubstituted or mono- or polysubstituted, identically or differently, by halogen or —CN, where, in addition, one or more $CH_2$ groups in this radical may be replaced by —O—, —S—, —C(O)—O and/or —O—C(O)— in such a way that hetero atoms (O and S) are not linked directly to one another;

$R^{32}$ is H, halogen, —CN, —NCS, aralkyl or an alkyl radical having from 1 to 15 carbon atoms which is unsubstituted or mono- or polysubstituted, identically or differently, by halogen or —CN, where, in addition, one or more $CH_2$ groups in this radical may be replaced by —O—, —S—, —C(O)—O— and/or —O—C(O)— in such a way that hetero atoms (O and S) are not linked directly to one another;

$Z^{31}$ and $Z^{32}$, independently of one another, are a single bond, —$CH_2$—, —$CH_2CH_2$—, —$CF_2CH_2$—, —$CH_2CF_2$— or —$CF_2CF_2$—;

$Z^{33}$, $Z^{34}$ and $Z^{35}$ are each, independently of one another, a single bond, —$CH_2CH_2$—, —$CF_2CH_2$—, —$CH_2CF_2$—, —$CF_2CF_2$—, —$CH_2O$—, —$CF_2O$—, —C(O)— or —C(O)—O—;

$A^{31}$ and $A^{32}$, independently of one another, are

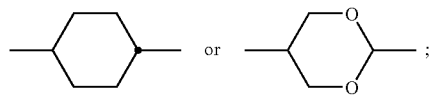

or $A^{33}$ and $A^{34}$, independently of one another, are

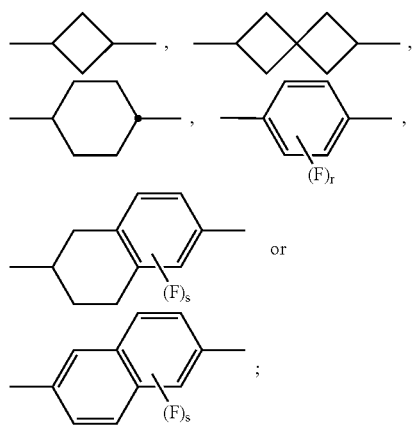

or $A^{35}$ is

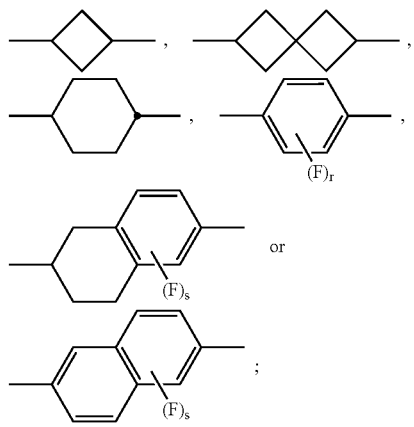

or $A^{35}$-$R^{32}$ together are

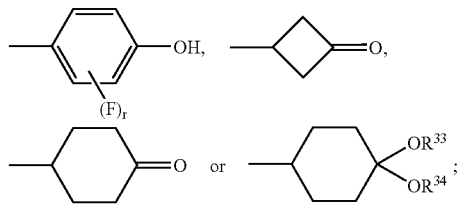

or $Z^{33}$-[-$A^{33}$-$Z^{34}$-]$_h$-[-$A^{34}$-$Z^{35}$-]$_j$-[-$A^{35}$-]$_k$-$R^{32}$ is

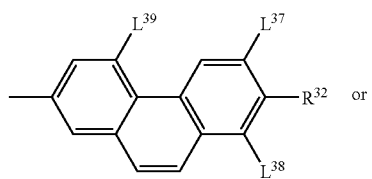

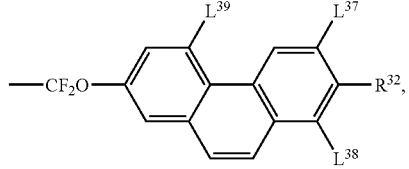

where $R^{32}$ is as defined above, and $L^{37}$, $L^{38}$ and $L^{39}$, independently of one another, are H or F;

r is 0, 1, 2, 3 or 4;

s is 0, 1, 2 or 3;

$R^{33}$ and $R^{34}$, independently of one another, are an alkanyl radical having from 1 to 7 carbon atoms or together are an alkylene bridge having from 2 to 7 carbon atoms;

with the proviso that, in the case of direct linking of $Z^{33}$ and $R^{32}$ to give —$Z^{33}$—$R^{32}$, $R^{32}$ is H, aralkyl or alkanyl if $Z^{33}$ is —C(=O)—, $R^{32}$ is aralkyl or alkanyl if $Z^{33}$ is —C(=O)—O—, and $Z^{33}$ is not —CH$_2$O— or —CF$_2$O—; that, in the case of direct linking of $Z^{34}$ and $R^{32}$ to give —$Z^{34}$—$R^{32}$, $R^{32}$ is H, aralkyl or alkanyl if $Z^{35}$ is —C(=O)—, $R^{32}$ is aralkyl or alkanyl if $Z^{34}$ is —C(=O)—O—, and $Z^{34}$ is not —CH$_2$O— or —CF$_2$O—; that, in the case of direct linking of $Z^{35}$ and $R^{32}$ to give —$Z^{35}$—$R^{32}$, $R^{32}$ is H, aralkyl or alkanyl if $Z^{35}$ is —C(=O)—, $R^{32}$ is aralkyl or alkanyl if $Z^{35}$ is —C(=O)—O—, and $Z^{35}$ is not —CH$_2$O— or —CF$_2$O—; that $R^{31}$ is not H if simultaneously f and g are both zero and $Z^{32}$ is a single bond.

Starting compounds which can be employed for the preparation of a pyran derivative of the general formula III are in principle all compounds of the formula I according to the invention where W=—CH$_2$— (i.e. compounds of the formula I-B). Besides the (endocyclic) C=C double bond in the central pyran ring, further aliphatic C=C double bonds optionally present in the compound of the formula I-B are also hydrogenated to a C—C single bond during the hydrogenation. Thus, for example, catalytic hydrogenation of a compound of the formula I-CB gives the corresponding compound of the formula III-CB (see scheme 7), where the meaning of f, g, h, j, k, $R^{31}$, $R^{32}$, $Z^{31}$, $Z^{33}$, $Z^{34}$, $Z^{35}$, $A^{31}$, $A^{32}$, $A^{33}$, $A^{34}$ and $A^{35}$ in the formula III-CB corresponds to the meaning of a, b, c, d, e, $R^{11}$, $R^{12}$, $Z^{11}$, $Z^{13}$, $Z^{14}$, $Z^{15}$, $A^{11}$, $A^{12}$, $A^{13}$, $A^{14}$ and $A^{15}$ respectively in the formula I-CB and $Z^{12}$=$Z^{32}$=single bond, with the proviso that, if $Z^{11}$, $Z^{13}$, $Z^{14}$ and/or $Z^{15}$ are —CH=CH— or $R^{11}$ and/or $R^{12}$ contain a —CH=CH— group, these aliphatic —CH=CH— groups are converted into CH$_2$—CH$_2$ groups.

for example, Raney nickel, 5% or 10% platinum on carbon and 5% palladium on activated carbon, in a suitable solvent, such as, for example, n-heptane, ethyl acetate, toluene, ethanol, methanol or THF. The reaction time is not crucial per se; the hydrogenation is usually carried out to complete conversion of the respective starting compound. The reaction temperature is generally in the range between room temperature and 100° C.

In the hydrogenation of the pyran derivative I to the pyran derivative III, a further chiral center is formed in the 5-position in addition to the center of asymmetry in the 2-position of the pyran ring. If the starting compound employed for the catalytic hydrogenation for formation of the tetrahydropyran III is a pyran derivative of the formula I which, after corresponding stereoselective synthesis described above or purification, is in enantiomerically pure (or enantiomerically enriched) form, only 2 of the 4 theoretically conceivable diastereomers of III are usually obtained (depending on the absolute configuration on the C-2 atom having the 2R,5R- and 2R,5S- or 2S,5R- and 2S,5S-configuration). These two isomers, which behave as diastereomers to one another, can be separated from one another by conventional methods, such as fractional crystallization or chromatography, enabling the tetrahydropyran of the formula III also to be obtained in enantiomerically pure form. The isomerically pure compounds of the formula III, like the isomerically pure compounds of the formula I, are used, inter alia, as chiral dopants for nematic liquid-crystalline media which effect the twisted arrangement of the compounds present in the liquid-crystalline media which is necessary for various electro-optical applications.

Scheme 7

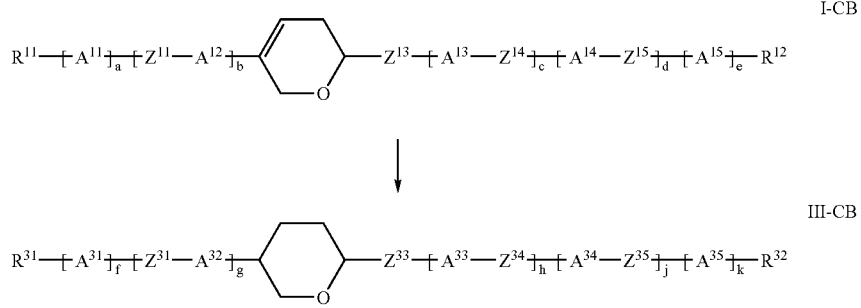

Analogously, the compounds of the formula I-DB according to the invention give the corresponding hydrogenated compounds III-DB, I-EB give III-EB, I-FB give III-FB, I-GB give III-GB, I-JB give III-JB, I-KB give III-KB, I-LB give III-LB, I-MB give III-MB, I-NB give III-NB, I-OB give III-OB, I-PB give III-PB, I-QB give III-QB, I-RB give III-RB, I-SB give III-SB and I-TB give III-TB. Illustrative compounds of the formula III are those which are derived from the pyran derivatives of the formula I shown in Tables 1 to 6 and differ therefrom in that they do not contain a C=C double bond in the central pyran ring. (For simplicity and better congruence, compounds of the formula III are also referred to as compounds of the formula III-B).

The catalytic hydrogenation is usually carried out at a hydrogen partial pressure of from 1 bar to 10 bar. The hydrogenation catalysts employed are usually transition-metal catalysts comprising nickel, platinum or palladium, such as, It is of course possible for compounds of the formula III themselves to be converted into other compounds of the formula III, by means of the same synthetic processes explained in detail above for the compounds of the formula I according to the invention. As also in the case of the compounds of the formula I according to the invention which contain a carboxyl function, carboxylic acid esters of the formula III-GB, in particular those of the formula III-GBI, are particularly suitable for this purpose. They can be saponified, for example, to give the corresponding free carboxylic acid, debenzylated by hydrogenation or desalylated with palladium catalysis and then further derivatised in order to facilitate, for example, the introduction of a difluorooxymethylene bridge. Of many other derivatisation possibilities, mention should also be made here by way of example of the possibility of reducing the ester of the formula III-GBI to the corresponding aldehyde, which can itself be reacted in a Wittig or Wittig-Horner reaction with introduction of an aliphatic C=C double bond.

Furthermore, the compounds of the formula III-KB are not only accessible directly by hydrogenation of corresponding compounds of the formula I-KB. They can also, for example, be prepared by firstly hydrogenating a pyran derivative of the formula I-B containing a terminal phenyl ring where $R^{12}$=O-aralkyl, such as, for example, compounds of the formula I-CBIIa where $R^{12a}$=aralkyl, with simultaneous debenzylation to give the corresponding compound of the formula III-B containing a terminal phenol ring, and subsequently converting the product into the corresponding compound of the formula III-KB containing a terminal cyclohexanone ring using suitable reducing agents (see, for example, J. March: Advanced Organic Chemistry; John Wiley & Sons, New York inter alia, 3rd Edn., 1985, p. 700, 5-11). For the illustrative compounds, this procedure is shown by scheme 8. The compounds of the formula III-KB are particularly suitable for the introduction of $CF_2O$ bridges, the details of which are described above for the reaction of the cyclohexanone derivatives of the formula I-KB, which are likewise in accordance with the invention.

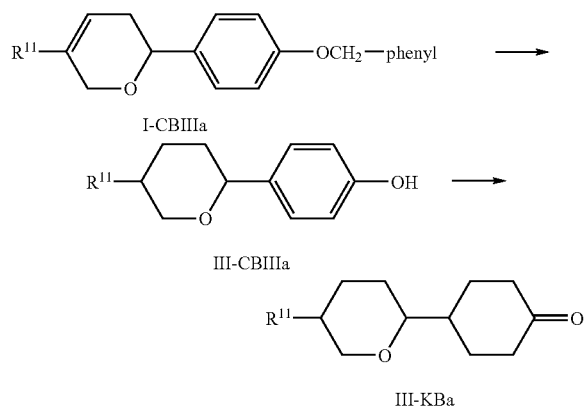

Scheme 8

Owing to the 2,5-disubstitution of the central pyran ring, the compound of the formula III can be in the form of either the cis- or the trans isomer. The trans isomer, which is generally preferred for many uses, is occasionally obtained as the only hydrogenation product. If the pyran of the formula III is formed predominantly as the cis isomer or as a mixture of the two isomers, the preferred trans isomer is obtained from the cis isomer by treatment with a strong base, for example potassium tert-butoxide in N-methylpyrrolidone, or with a strong acid, for example sulfuric acid in dioxane.

The compounds of the formula III are mesogenic, preferably liquid-crystalline, and are used in liquid-crystalline media.

The present invention furthermore relates to the use of a pyran derivative of the above formula I or of the formula III as constituent of a liquid-crystalline medium which is employed, in particular, in electro-optical display devices, such as TN, STN and active-matrix displays. These electro-optical display devices are, for example, displays of mobile radio equipment, screens of portable computers (notebooks) and TFT flat-panel screens.

The abbreviation m.p. denotes melting point, and cl.p. denotes clearing point. Furthermore, C=crystalline state, N=nematic phase, S=smectic phase and I=isotropic phase. $S_C$ denotes a smectic C phase, $S_B$ a smectic B phase, $S_A$ a smectic A phase. Δn denotes the optical anisotropy (Δn=$n_e$-$n_o$, where $n_e$ denotes the refractive index of the extraordinary ray and $n_o$ denotes the refractive index of the ordinary ray) (589 nm, 20° C.). ΔЄ denotes the dielectric anisotropy (ΔЄ=Є$_∥$-Є$_⊥$, where Є$_∥$ denotes the dielectric constant parallel to the longitudinal molecular axes, and Є$_⊥$ denotes the dielectric constant perpendicular thereto) (1 kHz, 20° C.). The optical data are measured at 20° C., unless expressly stated otherwise. The rotational viscosity $γ_1$ [mPa·s] is likewise determined at 20° C. The physical parameters are determined experimentally as described in "Licristal, Physical Properties Of Liquid Crystals, Description of the measurement methods", Ed. W. Becker, Merck KGaA, Darmstadt, revised edition, 1998, with the properties of individual compounds in some cases being determined after measurement of a defined amount of the compound (usually 5 or 10% by weight) in a defined host mixture having known properties followed by extrapolation.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLES

The starting compounds, reagents and solvents employed in the illustrative syntheses are either purchased or prepared by processes known from the literature. The illustrative syntheses are usually carried out in dry apparatuses with exclusion of moisture and—if required by the reaction in question—also under a protective-gas atmosphere for exclusion of air.

The course of reactions is generally monitored by thin-layer chromatography or gas chromatography. The reaction products are worked up and purified by conventional methods, for example by column chromatography or crystallization. Their structural identity is ensured by mass spectrometry and $^1$H-NMR spectroscopy. The yields are not optimized.

Example 1

Ring-Closing Metathesis

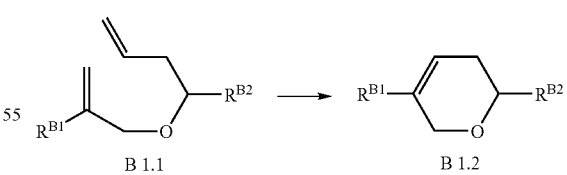

General Working Procedure B1 (GWP B1)

Compound B 1.1 (100 mmol), as a solid or dissolved in toluene, is warmed to from 40 to 60° C. under a nitrogen atmosphere. Tricyclohexylphosphine-(1,3-bis(2,4,6-trimethylphenyl)-4,5-dihydroimidazol-2-ylidenebenzylideneruthenium dichloride (COMP-Ru2a) (from 0.1 to 0.5 mmol; Strem Chemicals Inc., Kehl, Germany) is then added in one portion, whereupon very vigorous gas evolution immediately commences. The mixture is stirred at 60° C. for 15 minutes. After the gas evolution due to the ethene formed by the reaction has subsided, some more catalyst (0.05-0.1 mmol) is added in order to ensure the end of the reaction due to the continuing foaming. The reaction mixture is purified on silica gel, giving product B 1.2 after crystallization or vacuum distillation. Yields: 45-75%.

Some of the compounds prepared as described in GWP B1 are shown in Table B1.

(If the reaction is carried out on a larger scale, the catalyst is added in portions (usually from 4 to 8 portions of about 0.0025 mol % each). The end of the reaction is indicated by gas evolution no longer being observed after repeated addition of catalyst).

TABLE B1

| Compound B 1.2 No. | $R^{B1}$ | $R^{B2}$ |
|---|---|---|
| -1 | 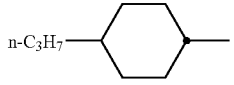 n-C$_3$H$_7$—◯— | 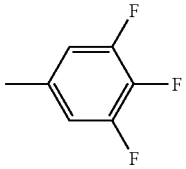 —⌬(F,F,F) |
| -2 | n-C$_3$H$_7$—◯— | —⌬(F,F)—OCF$_3$ |
| -3 | n-C$_3$H$_7$—◯—◯— | —⌬(F,F,F) |
| -4 | n-C$_3$H$_7$ | —◯—⌬(F,F,F) |
| -5 | n-C$_3$H$_7$ | —⌬(F,F,F) |
| -6 | C$_2$H$_5$—◯— | —⌬(F,F)—OCF$_3$ |
| -7 | CH$_3$—◯— | —⌬(F,F)—OCF$_3$ |

TABLE B1-continued
| Compound B 1.2 No. | $R^{B1}$ | $R^{B2}$ |
|---|---|---|
| -8 | $CH_3$ | 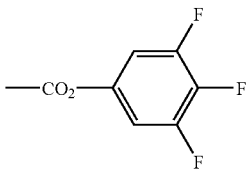 |
| -9 | $CH_3$ | 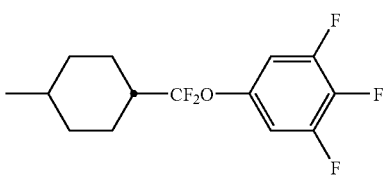 |
| -10 | $CH_3$ | 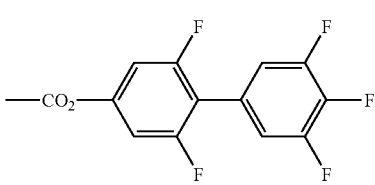 |
| -11 | $C_2H_5$ —⌬— | —⌬—$OCF_3$ |
| -12 | $CH_3$—⌬— | —⌬—$OCF_3$ |
| -13 | $C_2H_5$ | 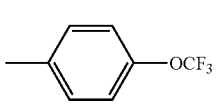 |
| -14 | n-$C_3H_7$ | 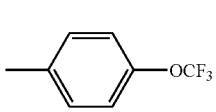 |
| -15 | n-$C_3H_7$ | 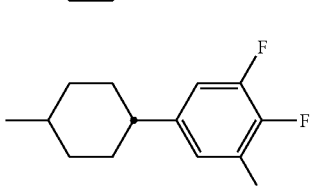 |
| -16 | $C_2H_5$ | 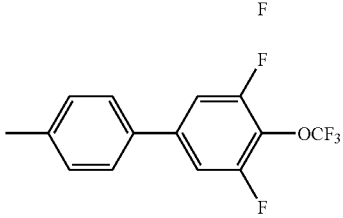 |

TABLE B1-continued
| Compound B 1.2 No. | $R^{B1}$ | $R^{B2}$ |
|---|---|---|
| -17 | $C_2H_5$ | 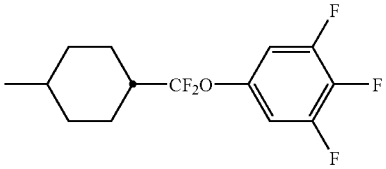 |
| -18 | n-$C_3H_7$ | 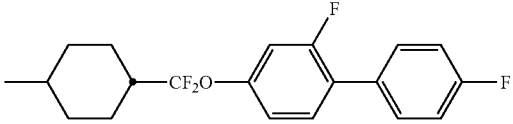 |
| -19 | n-$C_3H_7$ | 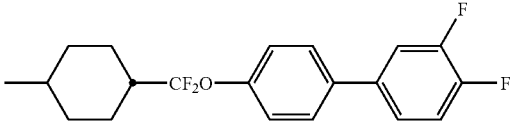 |
| -20 | n-$C_3H_7$ | 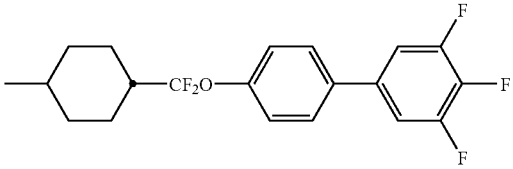 |
| -21 | $C_3H_7$ | 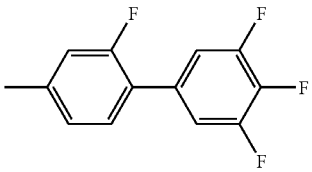 |
| -22 | n-$C_2H_7$ | 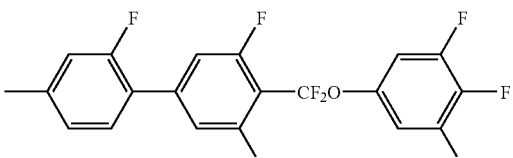 |
| -23 | n-$C_3H_7$ | 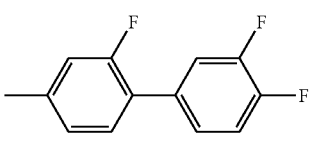 |
| -24 | n-$C_5H_{11}$ | 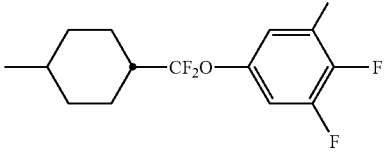 |
| -25 | n-$C_3H_7$ | 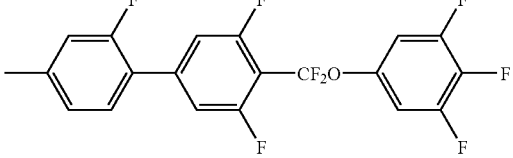 |

TABLE B1-continued
| Compound B 1.2 No. | $R^{B1}$ | $R^{B2}$ |
|---|---|---|
| -26 | n-C$_3$H$_7$ | 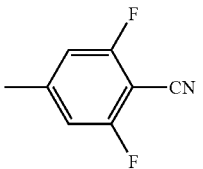 |
| -27 | n-C$_3$H$_7$ | 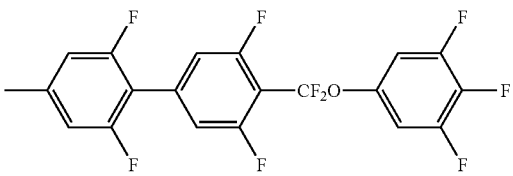 |
| -28 | n-C$_4$H$_9$ | 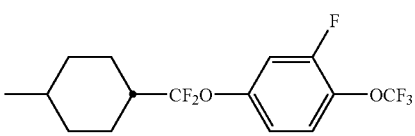 |
| -29 | n-C$_4$H$_9$ | 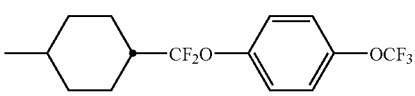 |
| -30 | n-C$_3$H$_7$ | 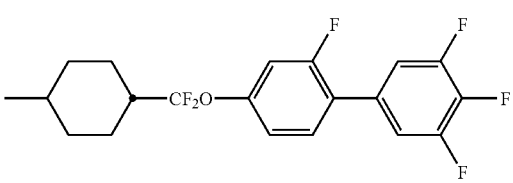 |
| -31 | n-C$_3$H$_7$ | 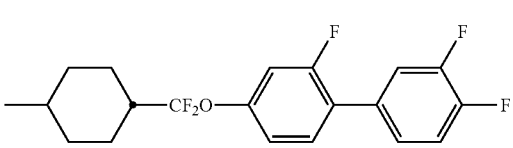 |
| -32 | C$_2$H$_5$ | 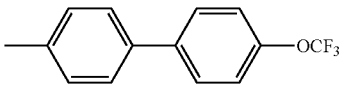 |
| -33 | n-C$_3$H$_7$ | 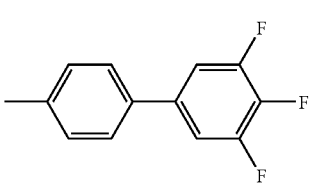 |
| -34 | n-C$_3$H$_7$ | 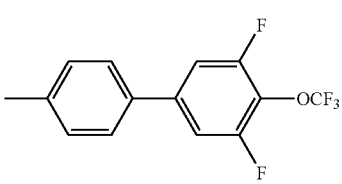 |

TABLE B1-continued

| Compound B 1.2 No. | R$^{B1}$ | R$^{B2}$ |
|---|---|---|
| -35 | n-C$_3$H$_7$ | cyclohexyl-3,4,5-trifluorophenyl |
| -36 | n-C$_3$H$_7$ | cyclohexyl-CF$_2$O-3,4,5-trifluorophenyl |
| -37 | C$_2$H$_5$ | phenyl-CO$_2$-3,4,5-trifluorophenyl |
| -38 | C$_2$H$_5$ | phenyl-(2,6-difluorophenyl)-CF$_2$O-3,4,5-trifluorophenyl |
| -39 | C$_2$H$_5$ | biphenyl-3,4,5-trifluoro |
| -40 | n-C$_3$H$_7$ | biphenyl-3,4,5-trifluoro |
| -41 | C$_2$H$_5$ | cyclohexyl-3,4,5-trifluorophenyl |
| -42 | C$_2$H$_5$ | biphenyl-3,4,5-trifluoro |

TABLE B1-continued
| Compound B 1.2 No. | $R^{B1}$ | $R^{B2}$ |
|---|---|---|
| -43 | n-$C_3H_7$ | 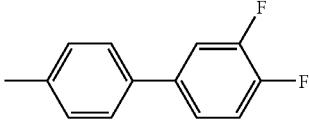 |
| -44 | n-$C_3H_7$ | 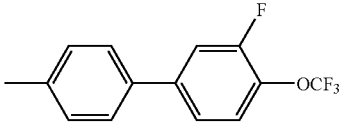 |
| -45 | n-$C_3H_7$ | 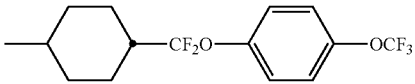 |
| -46 | n-$C_3H_7$ | 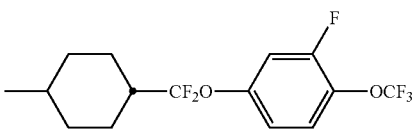 |
| -47 | n-$C_3H_7$ | 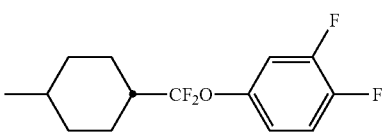 |
| -48 | n-$C_3H_7$ | 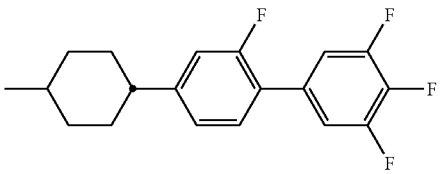 |
| -49 | $C_2H_5$ | 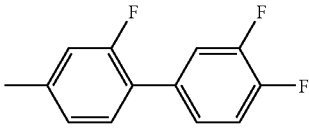 |
| -50 | $C_2H_5$ | 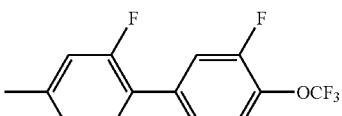 |
| -51 | $C_2H_5$ | 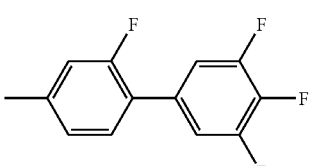 |
| -52 | n-$C_3H_7$ | 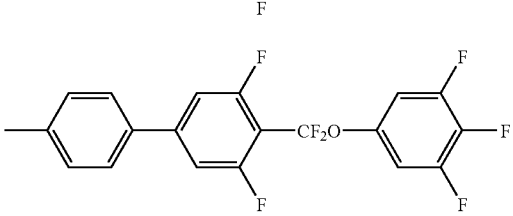 |

TABLE B1-continued

| Compound B 1.2 No. | R<sup>B1</sup> | R<sup>B2</sup> |
|---|---|---|
| -53 | n-C$_3$H$_7$ | 2,6-difluorophenyl-3,5-difluorophenyl-CF$_2$O-2,6-difluorophenyl-CF$_3$ |
| -54 | n-C$_3$H$_7$ | 2-fluoro-4-CN-phenyl |
| -55 | n-C$_3$H$_7$ | 2,6-difluorophenyl-3,5-difluorophenyl-CF$_2$O-2,6-difluorophenyl-CN |
| -56 | n-C$_3$H$_7$ | 2,6-difluorophenyl-3,5-difluorophenyl-CF$_2$O-phenyl-CF$_3$ |
| -57 | n-C$_3$H$_7$-(1,3-dioxane-2-yl) | 3,4,5-trifluorophenyl |
| -58 | n-C$_3$H$_7$ | 2,6-difluorophenyl-3,5-difluorophenyl-CF$_2$O-2,6-difluorophenyl-OCF$_3$ |
| -59 | n-C$_3$H$_7$ | 2,6-difluorophenyl-3,5-difluorophenyl-CF$_2$O-phenyl-OCF$_3$ |
| -60 | n-C$_3$H$_7$ | 2,6-difluorophenyl-CO$_2$-3,5-difluoro-4-CN-phenyl |

TABLE B1-continued

| Compound B 1.2 No. | R^{B1} | R^{B2} |
|---|---|---|
| -61 | n-C$_3$H$_7$ | (4-methyl-2,6-difluorophenyl)-(3,5-difluorophenyl)-CF$_2$O-(phenyl)-(3,4,5-trifluorophenyl) |
| -62 | CH$_3$ | (4-methyl-2-fluorophenyl)-(3,4,5-trifluorophenyl) |
| -63 | n-C$_3$H$_7$-cyclohexyl-(2-methyl-1,3-dioxan-5-yl)- | 2,3,4-trifluorophenyl |
| -64 | n-C$_3$H$_7$ | (4-methyl-2,6-difluorophenyl)-(3,5-difluorophenyl)-CF$_2$O-(2-fluorophenyl)-(3,4,5-trifluorophenyl) |
| -65 | n-C$_3$H$_7$ | 4-(trifluoromethyl)cyclohexyl |
| -66 | n-C$_4$H$_9$-cyclohexyl-(2-methyl-1,3-dioxan-5-yl)- | 2,3,4-trifluorophenyl |
| -67 | n-C$_3$H$_7$ | (4-methyl-2,6-difluorophenyl)-(3,5-difluorophenyl)-CF$_2$O-(2,6-difluorophenyl)-(3,4,5-trifluorophenyl) |
| -68 | n-C$_3$H$_7$ | (4-methyl-2,6-difluorophenyl)-(3,5-difluorophenyl)-CF$_2$O-(3-fluoro-4-OCF$_3$-phenyl) |
| -69 | n-C$_5$H$_{11}$ | (4-methyl-2,6-difluorophenyl)-CO$_2$-(3,5-difluoro-4-cyanophenyl) |

TABLE B1-continued
| Compound B 1.2 No. | $R^{B1}$ | $R^{B2}$ |
|---|---|---|
| -70 | $C_2H_5$ | 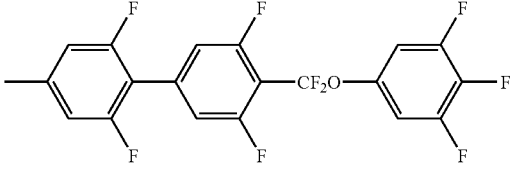 |
| -71 | $C_2H_5$ | 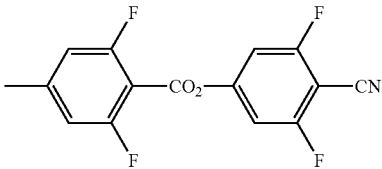 |
| -72 | n-$C_4H_9$ | 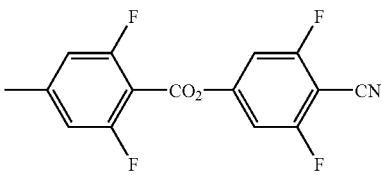 |
| -73 | n-$C_3H_7$ | 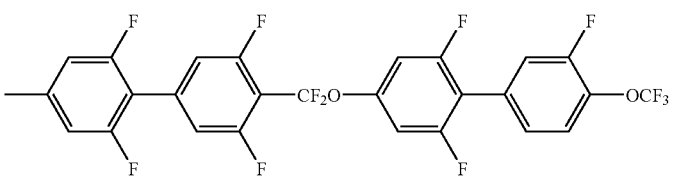 |
| -74 | n-$C_3H_7$ | 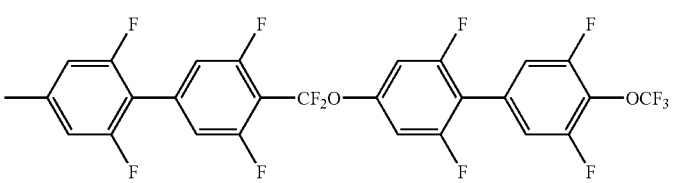 |
| -75 | $C_2H_5$ | 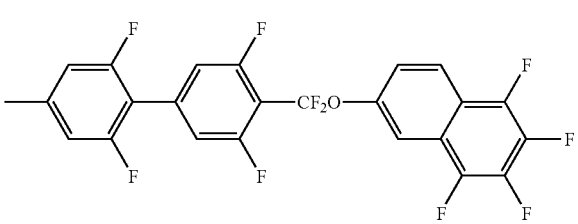 |
| -76 | $C_2H_5$ | 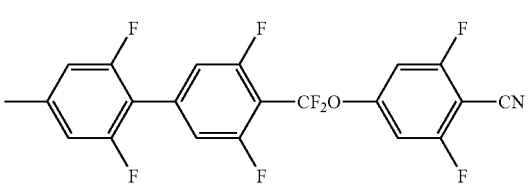 |
| -77 | n-$C_5H_{11}$ | 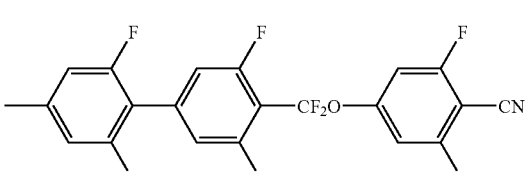 |

TABLE B1-continued

| Compound B 1.2 No. | R^{B1} | R^{B2} |
|---|---|---|
| -78 | n-C$_4$H$_9$ | 2,2',3,5,3''-pentafluoro-4'-(difluoromethyleneoxy)-4''-cyano biphenyl derivative |
| -79 | n-C$_7$H$_{15}$ | 2,2',3,5,3''-pentafluoro-4'-(difluoromethyleneoxy)-4''-cyano biphenyl derivative |
| -80 | n-C$_4$H$_9$ | 2,2',3,5,3'',4'',5''-heptafluoro-4'-(difluoromethyleneoxy) biphenyl derivative |
| -81 | n-C$_5$H$_{11}$ | 2,2',3,5,3'',4'',5''-heptafluoro-4'-(difluoromethyleneoxy) biphenyl derivative |
| -82 | n-C$_7$H$_{13}$ | 2,2',3,5,3'',4'',5''-heptafluoro-4'-(difluoromethyleneoxy) biphenyl derivative |
| -83 | CH$_3$ | cyclohexyl-3,4,5-trifluorophenyl |
| -84 | n-C$_4$H$_9$ | 2',3,4,5-tetrafluoro biphenyl |
| -85 | n-C$_3$H$_7$ | 2,2',3,5-tetrafluoro-4'-(difluoromethyleneoxy)-4''-isothiocyanato biphenyl derivative |

TABLE B1-continued

| Compound B 1.2 No. | $R^{B1}$ | $R^{B2}$ |
|---|---|---|
| -86 | n-C$_3$H$_7$ | 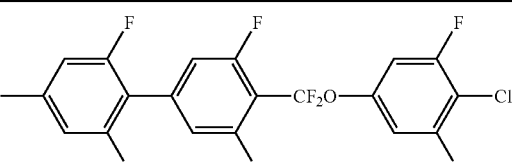 |
| -87 | n-C$_6$H$_{13}$ | 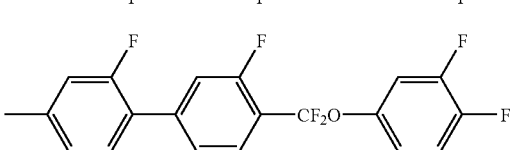 |
| -88 | n-C$_3$H$_7$ | 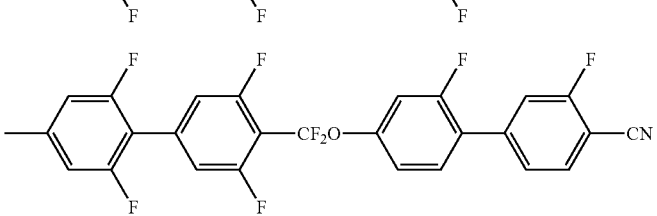 |

Example 2

Hydrogenation

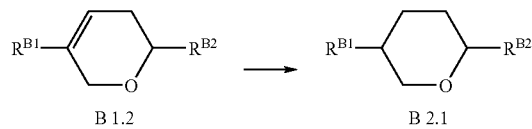

General Working Procedure B2 (GWP B2)

Compound B1.2 (100 mmol) is dissolved in heptane, hydrogenation catalyst (10% platinum on activated carbon or 5% Pd/C) is added, and the compound is hydrogenated at a temperature between room temperature and 50° C. under a hydrogen partial pressure of 5 bar. The reaction solution is concentrated and filtered, and the crude product B2.1 is isomerised if necessary and chromatographed and subsequently distilled under reduced pressure and/or crystallized. The cis/trans isomerization is carried out either by stirring for two hours with 15 mol % of potassium tert-butoxide in N-methylpyrrolidone or using a Lewis acid, such as MgBr$_2$, in toluene at between −10° C. and room temperature or using a Brönsted acid, such as trifluoromethanesulfonic acid, at room temperature for 24 hours.

Some of the compounds prepared in accordance with GWP B2 are shown in Table B2.

TABLE B2

| Compound B 2.1 No. | $R^{B2}$ | $R^{B2}$ |
|---|---|---|
| -1 | n-C$_3$H$_7$—⬡— | (3,4,5-trifluorophenyl) |
| -2 | n-C$_3$H$_7$—⬡— | (2,6-difluoro-4-OCF$_3$-phenyl) |

TABLE B2-continued

| Compound B 2.1 No. | R$^{B2}$ | R$^{B2}$ |
|---|---|---|
| -3 | n-C$_3$H$_7$-[cyclohexyl]-[cyclohexyl]- | -[3,4,5-trifluorophenyl] |
| -4 | n-C$_3$H$_7$ | -[cyclohexyl]-[2,3,4-trifluorophenyl] |
| -5 | n-C$_3$H$_7$ | -[3,4,5-trifluorophenyl] |
| -6 | C$_2$H$_5$-[cyclohexyl]- | -[3,5-difluoro-4-OCF$_3$-phenyl] |
| -7 | CH$_3$-[cyclohexyl]- | -[3,5-difluoro-4-OCF$_3$-phenyl] |
| -8 | CH$_3$ | -CO$_2$-[3,4,5-trifluorophenyl] |
| -9 | CH$_3$ | -[cyclohexyl]-CF$_2$O-[3,4,5-trifluorophenyl] |
| -10 | CH$_3$ | -CO$_2$-[2,6-difluorophenyl]-[3,4,5-trifluorophenyl] |
| -11 | C$_2$H$_5$-[cyclohexyl]- | -[4-OCF$_3$-phenyl] |

TABLE B2-continued

| Compound B 2.1 No. | R$^{B2}$ | R$^{B2}$ |
|---|---|---|
| -12 | CH$_3$–[cyclohexyl]– | –[phenyl]–OCF$_3$ |
| -13 | C$_2$H$_5$ | –[cyclohexyl]–[phenyl with 3,4,5-triF] |
| -14 | n-C$_3$H$_7$ | –[phenyl]–[phenyl with 3,5-diF, 4-OCF$_3$] |
| -15 | n-C$_3$H$_7$ | –[cyclohexyl]–CF$_2$O–[phenyl with 3,4,5-triF] |
| -16 | C$_2$H$_5$ | –[phenyl]–[phenyl with 3,5-diF, 4-CF$_2$O–[phenyl with 3,4,5-triF]] |
| -17 | C$_2$H$_5$ | –[cyclohexyl]–CF$_2$O–[phenyl with 3,4,5-triF] |
| -18 | n-C$_3$H$_7$ | –[cyclohexyl]–CF$_2$O–[phenyl with 2-F]–[phenyl with 4-F] |
| -19 | n-C$_3$H$_7$ | –[cyclohexyl]–CF$_2$O–[phenyl]–[phenyl with 3,4-diF] |
| -20 | n-C$_3$H$_7$ | –[cyclohexyl]–CF$_2$O–[phenyl]–[phenyl with 3,4,5-triF] |

TABLE B2-continued
| Compound B 2.1 No. | $R^{B2}$ | $R^{B2}$ |
|---|---|---|
| -21 | n-C$_3$H$_7$ | 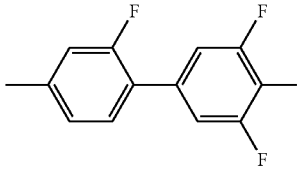 |
| -22 | C$_2$H$_5$ | 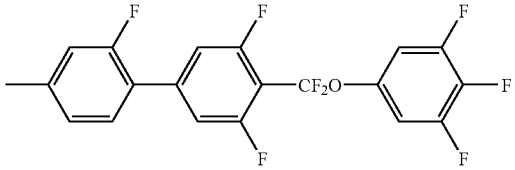 |
| -23 | n-C$_3$H$_7$ | 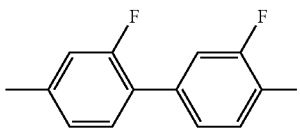 |
| -24 | n-C$_5$H$_{11}$ | 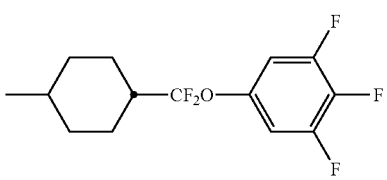 |
| -25 | n-C$_3$H$_7$ | 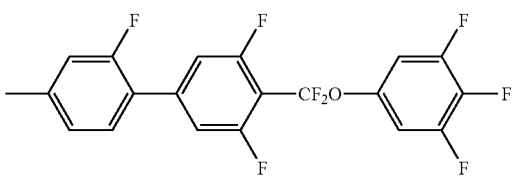 |
| -26 | n-C$_3$H$_7$ | 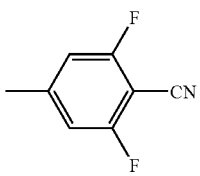 |
| -27 | n-C$_3$H$_7$ | 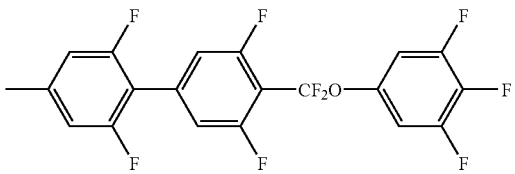 |
| -28 | n-C$_4$H$_9$ | 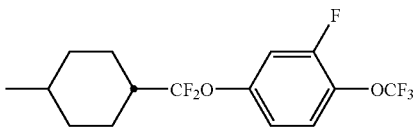 |
| -29 | n-C$_4$H$_9$ | 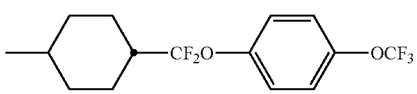 |

TABLE B2-continued
| Compound B 2.1 No. | $R^{B2}$ | $R^{B2}$ |
|---|---|---|
| -30 | n-$C_3H_7$ | 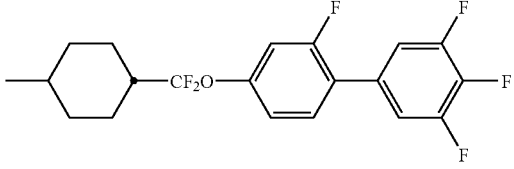 |
| -31 | n-$C_3H_7$ | 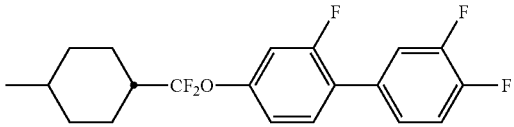 |
| -32 | $C_2H_5$ | 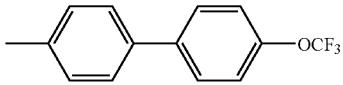 |
| -33 | n-$C_3H_7$ | 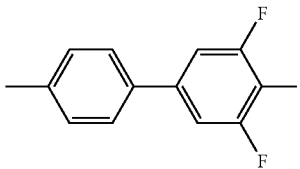 |
| -34 | n-$C_3H_7$ | 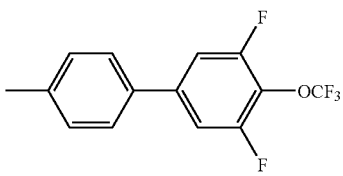 |
| -35 | n-$C_3H_7$ | 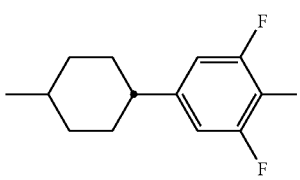 |
| -36 | n-$C_3H_7$ | 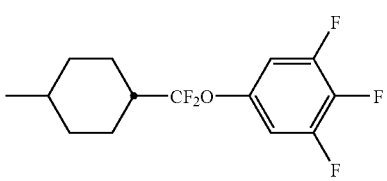 |
| -37 | $C_2H_5$ | 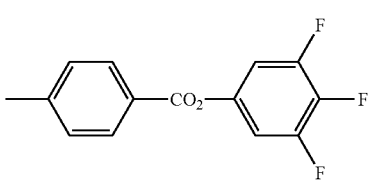 |
| -38 | $C_2H_5$ | 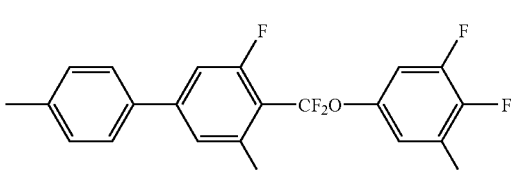 |

TABLE B2-continued

| Compound B 2.1 No. | $R^{B2}$ | $R^{B2}$ |
|---|---|---|
| -39 | $C_2H_5$ | 3,4,5-trifluoro-biphenyl |
| -40 | n-$C_3H_7$ | 3,4,5-trifluoro-biphenyl |
| -41 | $C_2H_5$ | cyclohexyl-(3,4,5-trifluorophenyl) |
| -42 | $C_2H_5$ | 3,4,5-trifluoro-biphenyl |
| -43 | n-$C_3H_7$ | 3,4-difluoro-biphenyl |
| -44 | n-$C_3H_7$ | 3-fluoro-4-OCF$_3$-biphenyl |
| -45 | n-$C_3H_7$ | cyclohexyl-CF$_2$O-(4-OCF$_3$-phenyl) |
| -46 | n-$C_3H_7$ | cyclohexyl-CF$_2$O-(3-fluoro-4-OCF$_3$-phenyl) |
| -47 | n-$C_3H_7$ | cyclohexyl-CF$_2$O-(3,4-difluorophenyl) |

TABLE B2-continued
| Compound B 2.1 No. | $R^{B2}$ | $R^{B2}$ |
|---|---|---|
| -48 | n-C$_3$H$_7$ | 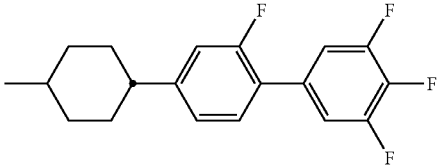 |
| -49 | C$_2$H$_5$ | 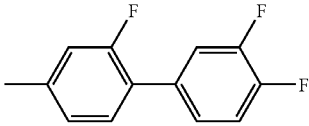 |
| -50 | C$_2$H$_5$ | 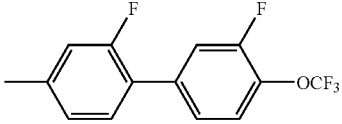 |
| -51 | C$_2$H$_5$ | 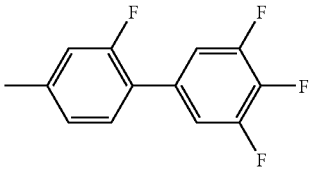 |
| -52 | n-C$_3$H$_7$ | 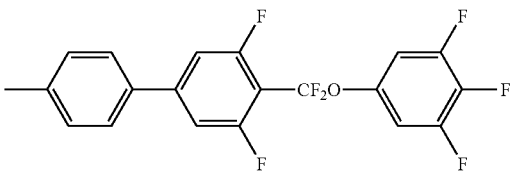 |
| -53 | n-C$_3$H$_7$ | 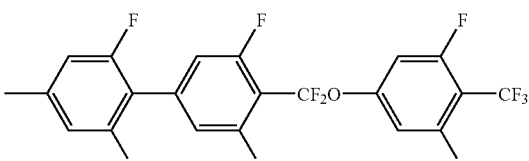 |
| -54 | n-C$_3$H$_7$ | 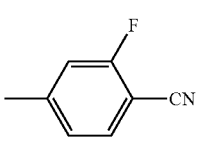 |
| -55 | n-C$_3$H$_7$ | 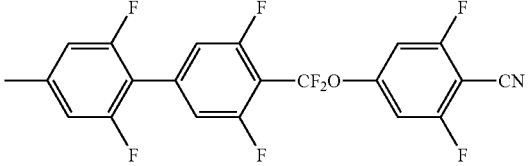 |
| -56 | n-C$_3$H$_7$ | 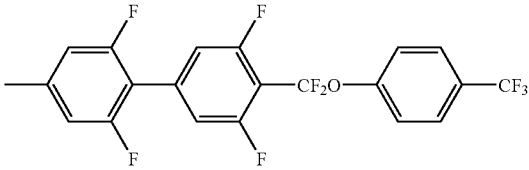 |

TABLE B2-continued

| Compound B 2.1 No. | $R^{B2}$ | $R^{B2}$ |
|---|---|---|
| -57 | n-C₃H₇-[1,3-dioxane]-2-yl (2-methyl) | 3,4,5-trifluorophenyl |
| -58 | n-C₃H₇ | 2,6-difluoro-4-[3,5-difluoro-4-(CF₂O-3,5-difluoro-4-OCF₃-phenyl)]biphenyl |
| -59 | n-C₃H₇ | 2,6-difluoro-4-[3,5-difluoro-4-(CF₂O-4-OCF₃-phenyl)]biphenyl |
| -60 | n-C₃H₇ | 2,6-difluorophenyl-CO₂-3,5-difluoro-4-CN-phenyl |
| -61 | n-C₃H₇ | 2,6-difluoro-4-[3,5-difluoro-4-(CF₂O-4-(3,4,5-trifluorophenyl)phenyl)]biphenyl |
| -62 | CH₃ | 2',3,4,5-tetrafluorobiphenyl |
| -63 | n-C₃H₇-cyclohexyl-[1,3-dioxan]-2-yl (2-methyl) | 3,4,5-trifluorophenyl |
| -64 | n-C₃H₇ | 2,6-difluoro-4-[3,5-difluoro-4-(CF₂O-2-fluoro-4-(3,4,5-trifluorophenyl)phenyl)]biphenyl |
| -65 | n-C₃H₇ | 4-CF₃-cyclohexyl |

TABLE B2-continued
| Compound B 2.1 No. | R$^{B2}$ | R$^{B2}$ |
|---|---|---|
| -66 | 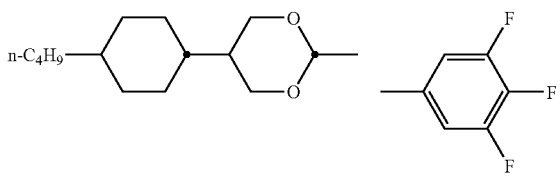 | 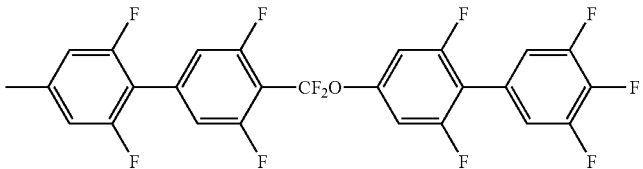 |
| -67 | n-C$_3$H$_7$ | 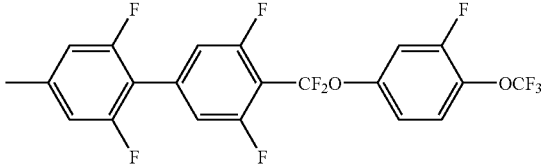 |
| -68 | n-C$_3$H$_7$ | 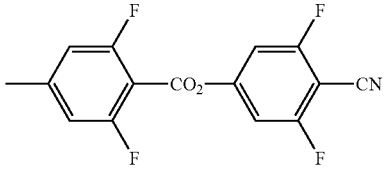 |
| -69 | n-C$_5$H$_{11}$ | 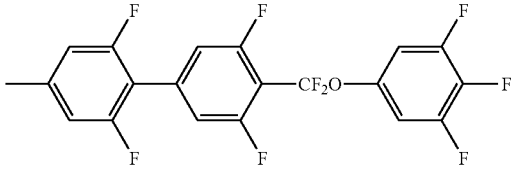 |
| -70 | C$_2$H$_5$ | 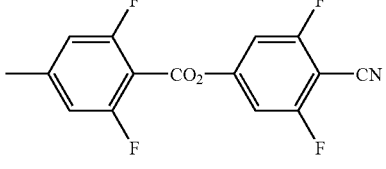 |
| -71 | C$_2$H$_5$ | 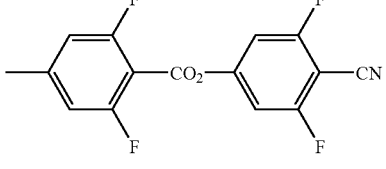 |
| -72 | n-C$_4$H$_9$ | 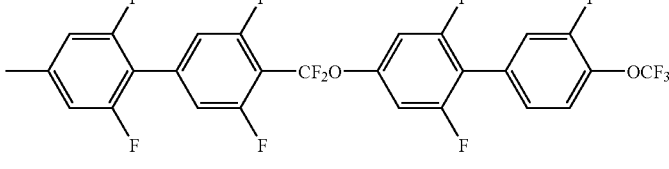 |
| -73 | n-C$_3$H$_7$ | |

TABLE B2-continued

| Compound B 2.1 No. | $R^{B2}$ | $R^{B2}$ |
|---|---|---|
| -74 | n-C$_3$H$_7$ | (tetrafluoro-biphenyl)-CF$_2$O-(difluoro-phenyl)-(difluoro-phenyl)-OCF$_3$ |
| -75 | C$_2$H$_5$ | (tetrafluoro-biphenyl)-CF$_2$O-(tetrafluoro-naphthyl) |
| -76 | C$_2$H$_5$ | (tetrafluoro-biphenyl)-CF$_2$O-(difluoro-phenyl)-CN |
| -77 | n-C$_5$H$_{11}$ | (tetrafluoro-biphenyl)-CF$_2$O-(difluoro-phenyl)-CN |
| -78 | n-C$_4$H$_9$ | (tetrafluoro-biphenyl)-CF$_2$O-(difluoro-phenyl)-CN |
| -79 | n-C$_7$H$_{15}$ | (tetrafluoro-biphenyl)-CF$_2$O-(difluoro-phenyl)-CN |
| -80 | n-C$_4$H$_9$ | (tetrafluoro-biphenyl)-CF$_2$O-(difluoro-phenyl)-F |
| -81 | n-C$_5$H$_{11}$ | (tetrafluoro-biphenyl)-CF$_2$O-(difluoro-phenyl)-F |

TABLE B2-continued

| Compound B 2.1 No. | $R^{B2}$ | $R^{B2}$ |
|---|---|---|
| -82 | n-C$_3$H$_7$ | 2,6-difluorophenyl—2',3'-difluorophenyl—CF$_2$O—3,4,5-trifluorophenyl |
| -83 | CH$_3$ | cyclohexyl—3,4,5-trifluorophenyl |
| -84 | n-C$_4$H$_9$ | 2'-fluorophenyl—3,4,5-trifluorophenyl |
| -85 | n-C$_3$H$_7$ | 2,6-difluorophenyl—2',3'-difluorophenyl—CF$_2$O—4-isothiocyanatophenyl |
| -86 | n-C$_3$H$_7$ | 2,6-difluorophenyl—2',3'-difluorophenyl—CF$_2$O—3,5-difluoro-4-chlorophenyl |
| -87 | n-C$_6$H$_{13}$ | 2,6-difluorophenyl—2',3'-difluorophenyl—CF$_2$O—3,4,5-trifluorophenyl |
| -88 | n-C$_3$H$_7$ | 2,6-difluorophenyl—2',3'-difluorophenyl—CF$_2$O—2''-fluorophenyl—3''',4'''-difluoro-CN |

Example 3

Synthesis of Allyl Compounds of the Formula IV a)

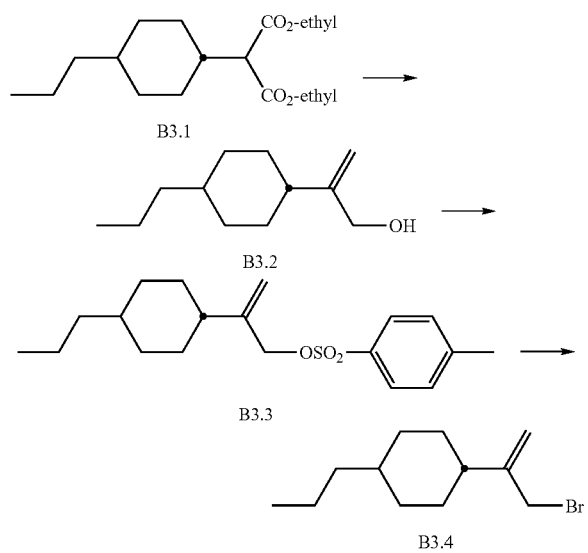

Diethyl 4-trans-propyl-1-cyclohexylmalonate B3.1 (0.2 mol) in anhydrous dimethoxyethane is added dropwise to a suspension of sodium hydride (0.24 mol) in dimethoxyethane. The mixture is refluxed for 5 hours, and lithium aluminium hydride (0.5 mol) is then added at 0° C. The mixture is subsequently refluxed for a further 3 hours. After cooling to 0° C., ethyl formate, then water, aqueous sodium hydroxide solution and again water are added. The mixture is filtered, and the aqueous phase is extracted with tert-butyl methyl ether. The combined organic phases are dried and evaporated, and the residue is filtered through silica gel. Removal of the solvent gives the allyl alcohol B3.2. Yield: 76%.

4-Dimethylaminopyridine (0.4 mol) in tetrahydrofuran is added dropwise at 0° C. with stirring to a solution of p-toluenesulfonyl chloride (0.2 mol) and 2-(4-trans-propyl-1-cyclohexylallyl alcohol B3.2 (0.2 mol) in tetrahydrofuran. When the addition is complete, the mixture is allowed to warm to room temperature and is then refluxed for a further 12 hours. After cooling, the mixture is poured into a mixture of ice and concentrated hydrochloric acid. The organic phase is separated off, and the aqueous phase is extracted three times with tert-butyl methyl ether. The combined organic phases are dried and evaporated, and the residue is chromatographed on silica gel. The allyltosyl ester B3.3 is obtained as an oil. Yield: 87%. The corresponding allyl methanesulfonate can be prepared analogously using methanesulfonyl chloride and the corresponding allyl trifluoromethanesulfonate can be prepared analogously using trifluoromethanesulfonic anhydride.

The allyltosyl ester B3.3 (0.1 mol) is taken up in acetone and refluxed for 36 hours with lithium bromide (0.1 mol). After cooling, the precipitate is filtered off, the filtrate is evaporated, and the residue formed is filtered through silica gel. Evaporation gives 2-(4-trans-propyl-1-cyclohexylallyl bromide B3.4. Yield: 68%.

b)

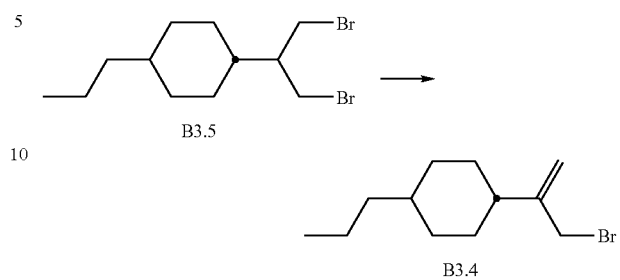

Compound B3.5 (0.553 mol) and potassium tert-butoxide (0.692 mol) are combined in toluene and stirred overnight at 80° C. After cooling, water is added, and the mixture is extracted with methyl tert-butyl ether. The organic phase is separated off, dried and evaporated. The residue is taken up in pentane and filtered through silica gel. Evaporation gives the allyl bromide B3.4. Yield: 73%.

c)

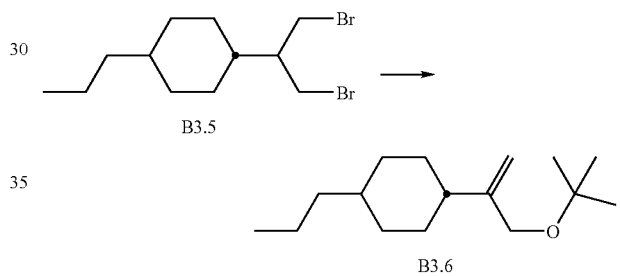

2-(4-trans-Propyl-1-cyclohexyl)-1,3-dibromopropane B3.5 (0.5 mol) is stirred for 16 hours at 80° C. in toluene together with potassium tert-butoxide (1.25 mol). After cooling, water is added, tert-butyl methyl ether is added, and the mixture is extracted. The organic phase is dried and evaporated, and the residue is filtered through silica gel. 2-(4-trans-Propyl-1-cyclohexyl)allyl tert-butyl ether B3.6 is obtained as an oily product. Yield: 68%.

d)

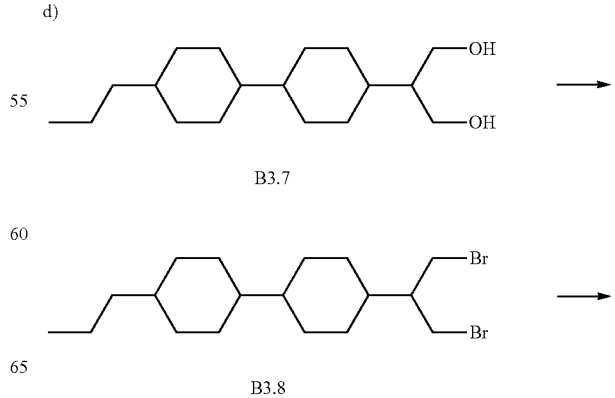

-continued

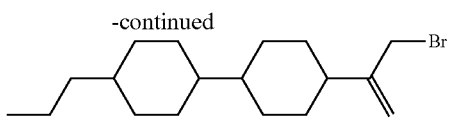

B3.9

Triphenylphosphine (0.4 mol) is suspended in acetonitrile and cooled to 10° C., and bromine (0.39 mol) is added at this temperature. The suspension is stirred for a further 1 hour, and propyldicyclohexylpropane-diol B3.7 (0.2 mol) is then added. The mixture is stirred overnight at room temperature and subsequently refluxed for 4 hours. After cooling to room temperature, water is added, and the mixture is extracted with petroleum ether. The organic phase is dried and evaporated, and the residue is filtered through silica gel. Evaporation gives propyldicyclohexylpropane dibromide B3.8. Yield: 94%.

The dibromide B3.8 (0.402 mol) and potassium tert-butoxide (0.503 mol) are mixed in toluene and stirred at 80° C. overnight. The mixture is cooled, water is added, and the mixture is extracted with methyl tert-butyl ether. The organic phase is dried and evaporated. The residue is filtered through silica gel. Evaporation gives the allyl bromide B3.9. Yield: 90%.

e)

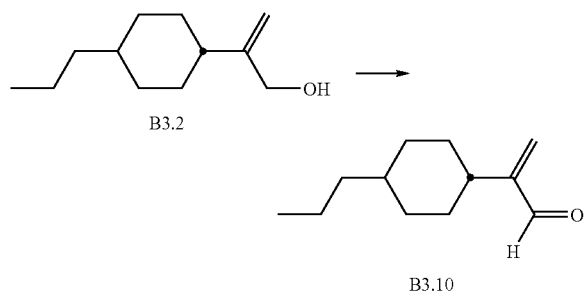

2-(4-trans-Propyl-1-cyclohexyl)allyl alcohol (0.2 mol) is stirred vigorously at room temperature for 24 hours with 105 g of active manganese dioxide in 350 ml of dichloromethane. The mixture is then filtered, the residue is washed with dichloromethane, and the organic phase is evaporated and filtered through silica gel with toluene/methyl tert-butyl ether. Yield of the acrolein B3.10: 64%.

f)

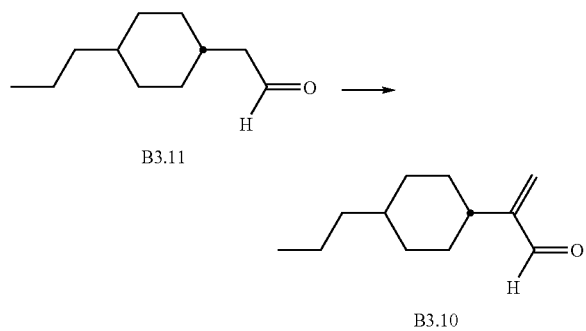

The aldehyde B3.11 (0.321 mol) and N,N-dimethylmethyleneiminium chloride (Eschenmoser's salt; 0.321 mol) are suspended in dichloromethane. Triethylamine is then added dropwise at room temperature, and the mixture is stirred overnight. The mixture is extracted by shaking with water, the organic phase is separated off and evaporated in a rotary evaporator, the residue is taken up in heptane/methyl tert-butyl ether, and the solution is filtered through silica gel. Yield: 40%.

Example 4

Synthesis of Homoallyl Compounds of the Formula V a) General Working Procedure B 4a (GWP B4a)

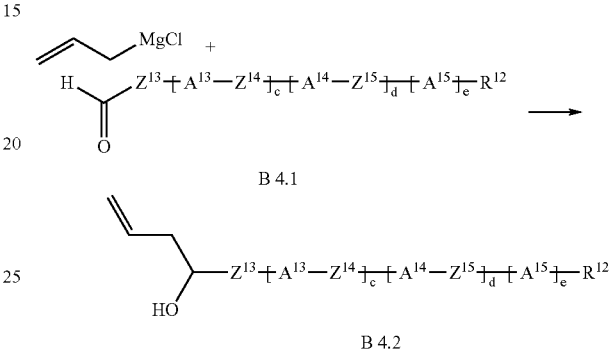

The aldehyde B 4.1, dissolved in 100 ml of THF, is added dropwise with gentle ice-cooling to 200 ml (2 mol) of allylmagnesium chloride in diethyl ether (Aldrich Co.), and the mixture is then stirred at room temperature for 4 hours. The reaction mixture is subsequently poured into 100 ml of 0.5N HCl and stirred for five minutes. The organic phase is separated off, and the aqueous phase is extracted twice with methyl tert-butyl ether. The combined organic extracts are rinsed with water; dried, filtered and evaporated. The crude product, obtained quantitatively, can be used directly in the subsequent reaction owing to its purity.

b) General Working Procedure B 4b (GWP B 4b)

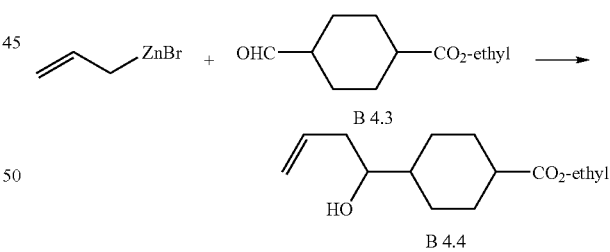

Allylmagnesium chloride (0.40 mol) in 400 ml of diethyl ether (Aldrich Co.) is added dropwise with external cooling to a solution of zinc bromide (0.4 mol) in 200 ml of THF at such a rate that the temperature is between 10 and 15° C. The resultant suspension is stirred at this temperature for a further 2 hours, before 0.4 mol of the aldehyde B 4.3, dissolved in 400 ml of diethyl ether, is added dropwise. The suspension is stirred at room temperature for a further 16 hours and then poured into 600 ml of 0.5N HCl. The organic phase is isolated, dried using sodium sulfate and evaporated. The crude product can be employed without further purification. Instead of zinc bromide, ClTi(i-propoxide)$_3$ can also be used for the transmetallation.

This reaction procedure with transmetallation is particularly suitable for the reaction of aldehydes which, besides the aldehydic carbonyl function, contain a functional group which is reactive towards Grignard reagents, such as a carboxylate or nitrile group.

Example 5

Synthesis of Compounds of the Formula II

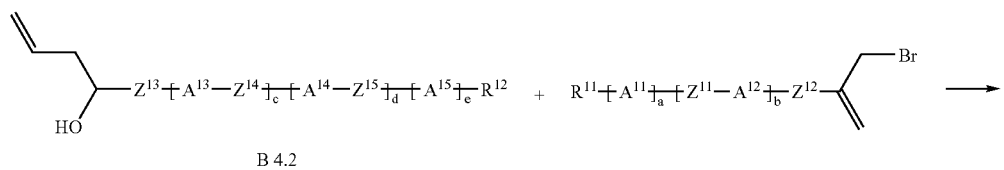

B 4.2

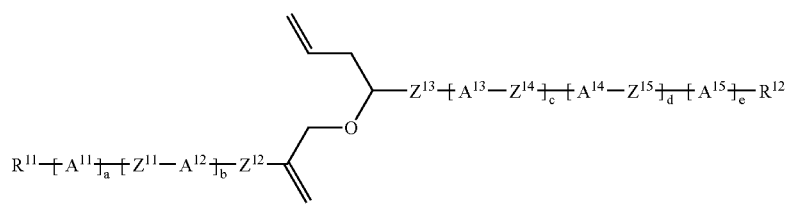

B 5.1 a) General Working Procedure B 5a (GWP B5a)

(For Compounds B 4.2 for which $Z^{13}$, $Z^{14}$ and $Z^{15}$ are not $CO_2$)

0.4 mol of granulated sodium hydroxide is suspended in 200 ml, of THF at room temperature, and 2 ml of water, 0.4 mol of homoallyl alcohol B 4.2 and 0.02 mol of N-cetyl-N,N,N-trimethylammonium bromide are added at 25° C. with stirring. 0.4 mol of the allyl bromide is then added with stirring. The mixture is stirred at from 40 to 50° C. for 20 hours. A further 0.05 to 0.1 mol of allyl bromide is subsequently added to homoallyl alcohol B 4.2 which has not reacted according to TLC in order to complete the reaction after continued stirring (12 hours). After cooling, the mixture is poured into 500 ml of ice-water and extracted twice with methyl tert-butyl ether. The combined organic extracts are dried, evaporated and filtered through silica gel with heptane/toluene. The compounds B 5.1 are usually obtained as an oil. Yield: 70 to 95%.

b) General Working Procedure B 5b (GWP B5b)

0.46 mol of NaH (60% suspension in paraffin oil) is initially introduced in 200 ml of THF. The homoallyl alcohol B 4.2 (0.4 mol) in 200 ml of THF is added dropwise at a temperature between −10 and +20° C. Stirring is continued at between 20 and 30° C. until the evolution of hydrogen is complete. 0.4 mol of the allyl bromide in 200 ml of THF is then added dropwise at room temperature, and, depending on the result of the TLC check, the mixture is stirred at room temperature for from 12 to 48 hours. The reaction mixture is poured into ice-water, extracted with methyl tert-butyl ether, dried, evaporated and filtered through silica gel with heptane/toluene.

c) General Working Procedure B 5c (GWP B5c)

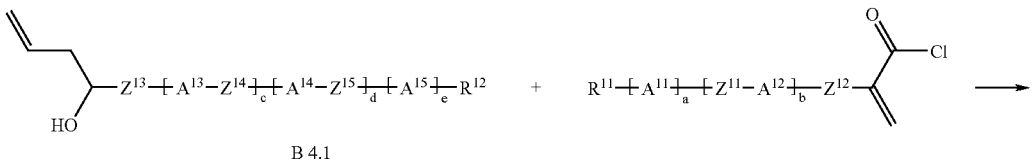

B 4.1

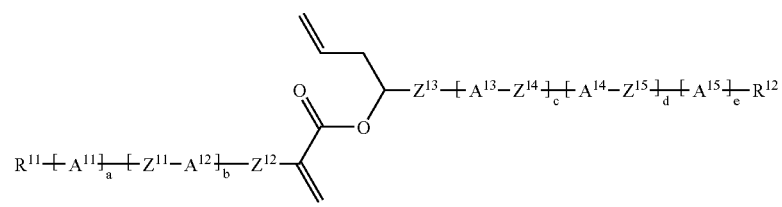

B 5.2

Acrylic acid esters B 5.2 are prepared by process GWP B 5a or GWP B 5b, with the allyl bromide being replaced by the corresponding acid chloride.

Example 6

Physical Parameters of Compounds According to the Invention

Table B3 shows selected physical parameters of some compounds according to the invention which have been prepared by the procedures of the above examples. (The entries in the "Compound" column refer to the names given in Examples 1 to 5).

TABLE B3

| Compound | Δn | Δε | $\gamma_1$ [mPa·s] | m.p. [°C.] | cl.p. [°C.] | Phase transitions |
|---|---|---|---|---|---|---|
| B1.2-1* | 0.0640 | 12.8 | 205 | 48 | 21*** | C 48 I |
| B1.2-2* | 0.0740 | 14.5 | 286 | 35 | 36*** | C 35 N (10.3) I |
| B1.2-3* | 0.1060 | 12.1 | 562 | 98 | 217 | C 98 N 217 I |
| B1.2-4* | 0.0560 | 13.3 | 203 | 74 | 3*** | C 74 I |
| B1.2-7* | 0.0740 | 14.5 | 286 | 35 | 36*** | C 35 N (10.3) I |
| B1.2-8* | −0.0142 | 7.5 | | 62 | | C 62 I |
| B1.2-9* | 0.0520 | 14.8 | 99 | 89 | 25*** | C 89 I |
| B1.2-11* | 0.0760 | 8.2 | 137 | 84 | 63*** | C 84 SmB? 90 I |
| B1.2-12* | 0.0739 | 8.4 | | 79 | 37*** | C 79 SmB (74) I |
| B2.1-1* | 0.0710 | 12.2 | 182 | 57 | 62*** | C 57 N (50.9) I |
| B2.1-2* | 0.0770 | 13.5 | 325 | 69 | 68*** | C 69 N 70 I |
| B2.1-3* | 0.1020 | 11.8 | 582 | 113 | 256 | C 113 N 256 I |
| B2.1-4* | 0.0599 | 14.1 | 136 | 71 | 32*** | C 71 I |
| B2.1-9* | 0.0490 | 34.9 | 142 | 54 | 16*** | C 54 I |
| B2.1-11* | 0.0810 | 8.5 | 149 | 37 | 106 | C 37 SmB 93 N 106 I |
| B2.1-13* | 0.0475 | 14.0 | 140 | 72 | 14*** | C 72 I |
| B2.1-14* | 0.1256 | 18.0 | 239 | 58 | 61 | C 58 SmA (37) N 61 I |
| B2.1-15* | 0.0570 | 13.4 | | 34 | 58 | C 34 N 58 I |
| B2.1-16* | 0.1493 | 27.3 | 287 | 77 | 91 | C 77 N 91 I |
| B2.1-17* | 0.0540 | 14.1 | 124 | 45 | 35*** | C 45 N (35) I |
| B2.1-18* | 0.1390 | 9.4 | | 84 | 232 | C 84 N 232 I |
| B2.1-19* | 0.1370 | 10.7 | | 47 | 238 | C 47 SmB 91 N 238 I |
| B2.1-20* | 0.1291 | 15.7 | 725 | 60 | 207 | C 60 SmB 81 N 207 I |
| B2.1-21* | 0.1071 | 17.3 | 176 | 64 | 13*** | C 64 I |
| B2.1-22* | 0.1310 | 29.9 | | 89 | 69*** | C 89 N (77) I |
| B2.1-23* | 0.1254 | 12.7 | 225 | 43 | 44 | C 43 N 44 I |
| B2.1-24* | 0.0568 | 11.8 | 216 | 39 | 75 | C 39 N 75 I |
| B2.1-25* | 0.1364 | 29.7 | | 70 | 102 | C 70 N 102 I |
| B2.1-26* | 0.0580 | 35.6 | 75 | 27 | −83*** | C 27 I |
| B2.1-27* | 0.1231 | 34.9 | 457 | 81 | 83 | C 81 N 83 I |
| B2.1-28* | 0.0623 | 11.5 | | | 106 | SmB 81 N 106 I |
| B2.1-29* | 0.0689 | 9.1 | | −54 | 117*** | C? −54 SmB 129 I |
| B2.1-30* | 0.1220 | 19.1 | 625 | 61 | 192 | C 61 N 192 I |
| B2.1-31* | 0.1328 | 13.4 | 806 | 44 | 213 | C 44 Sm? 45 B 213 I |
| B2.1-32* | 0.1422 | 10.1 | 116 | 54 | 106*** | C 54 Sm? SmB 154 SmA 168 I |
| B2.1-33* | 0.1243 | 14.8 | 178 | 42 | 44*** | C 41 I |
| B2.1-34* | 0.1256 | 18.0 | 239 | 58 | 61 | C 58 SmA (37) N 61 I |
| B2.1-35* | 0.0599 | 14.1 | 136 | 71 | 32*** | C 71 I |
| B2.1-36* | 0.0570 | 13.4 | 160 | 35 | 66 | C 35 N 66 I |
| B2.1-37* | 0.1070 | 29.7 | 213 | 89 | 48*** | C 89 I |
| B2.1-38* | 0.1493 | 27.3 | 287 | 78 | 92 | C 78 N 92 I |
| B2.1-39* | 0.1159 | 14.5 | 130 | 52 | 17*** | C 52 I |
| B2.1-40* | 0.1243 | 14.8 | 178 | 41 | 44*** | C 41 I |
| B2.1-41* | 0.0475 | 14.0 | 140 | 72 | 14*** | C 72 I |
| B2.1-42* | 0.1159 | 14.5 | 130 | 52 | 17*** | C 52 I |
| B2.1-43* | 0.1430 | 9.6 | 189 | 50 | 99 | C 50 SmA-1 (32) SmA-2 64 N 99 I |
| B2.1-44* | 0.1380 | 12.7 | 236 | 45 | 90*** | C 45 SmA-1 68 SmA-2 118 I |
| B2.1-45* | 0.0780 | 9.1 | 178 | −41 | 129 | C −41 SmB 123 N 129 I |
| B2.1-46* | 0.0701 | 11.7 | 199 | | 106 | SmB 74 N 106 |
| B2.1-47* | 0.0688 | 9.7 | 187 | 41 | 96 | C 41 SmB 51 N 96 I |
| B2.1-48* | 0.1384 | 19.7 | | 74 | 198 | C 74 N 198 I |
| B2.1-49* | 0.1157 | 12.3 | | 28 | 25*** | C 28 N (11) I |
| B2.1-50* | 0.1100 | 15.2 | 177 | 37 | 39 | C 37 SmA (35) N 39 I |
| B2.1-52* | 0.1450 | 23.2 | 300 | 75 | 118 | C 75 N 118 I |
| B2.1-53** | 0.1190 | 40.8 | 529 | 91 | 47*** | C 91 I |
| B2.1-54* | 0.0800 | 28.2 | 128 | 32 | −50*** | C 32 I |
| B2.1-57* | 0.0550 | 23.7 | 241 | 87 | 20*** | C 87 I |
| B2.1-58* | 0.1158 | 35.6 | 541 | 74 | 101 | C 74 N 101 I |

TABLE B3-continued

| Compound | Δn | Δε | γ₁ [mPa·s] | m.p. [°C.] | cl.p. [°C.] | Phase transitions |
|---|---|---|---|---|---|---|
| B2.1-59* | 0.1330 | 25.3 | 466 | 80 | 120 | C 80 N 120 I |
| B2.1-60* | 0.1230 | 61.4 | 625 | 79 | 91 | C 79 N 91 I |
| B2.1-61* | 0.1706 | 35.4 | | 115 | 198 | C 115 N 198 I |
| B2.1-62* | 0.0950 | 18.9 | 160 | 58 | −30*** | C 58 I |
| B2.1-63* | 0.0871 | 21.7 | | 106 | 207 | C 106 N 207 I |
| B2.1-64** | 0.1649 | 37.9 | | 98 | 193 | C 98 N 193 I |
| B2.1-65* | 0.0049 | 7.7 | 76 | 7 | −78*** | C 7 SmB 15 I |
| B2.1-66* | 0.0880 | 21.3 | | 91 | 203 | C 91 SmH (63) N 203 I |
| B2.1-67** | 0.1510 | 42.1 | | 144 | 181 | C 144 N 181 I |
| B2.1-68* | 0.1180 | 29.8 | 541 | 48 | 105 | C 48 SmA (46) N 105 I |
| B2.1-69* | 0.1279 | 57.4 | | 50 | 95 | C 50 N 95 I |
| B2.1-70* | 0.1149 | 35.0 | 356 | 91 | 38*** | C 91 N (59) I |
| B2.1-71* | 0.1202 | 64.0 | 536 | 77 | 38*** | C 77 N (66) I |
| B2.1-72* | 0.1270 | 58.0 | 534 | 76 | 90 | C 76 N 90 I |
| B2.1-73** | 0.1634 | 37.7 | | 121 | 205 | C 121 N 205 I |
| B2.1-74** | 0.1411 | 43.8 | | 128 | 201 | C 128 N 201 I |
| B2.1-75** | 0.1431 | 29.8 | | 113 | 149 | C 113 N 149 I |
| B2.1-76* | 0.1459 | 67.8 | | 98 | 128 | C 98 N 128 I |
| B2.1-77* | 0.1490 | 61.8 | | 65 | 142 | C 65 SmC (44) N 142 I |
| B2.1-78* | 0.1477 | 64.2 | | 79 | 139 | C 79 N 139 I |
| B2.1-79* | 0.1459 | 58.5 | | 64 | 131 | C 64 N 131 I |
| B2.1-80* | 0.1171 | 32.4 | 381 | 90 | 54*** | C 90 N (81) I |
| B2.1-81* | 0.1205 | 31.9 | 589 | 82 | 89 | C 82 N 89 I |
| B2.1-82* | 0.1130 | 30.3 | 662 | 83 | 86 | C 83 N 86 I |
| B2.1-83* | 0.0459 | 14.5 | 126 | 72 | −19*** | C 72 I |
| B2.1-84* | 0.0960 | 16.4 | 185 | 55 | 14*** | C 55 I |
| B2.1-85* | 0.2052 | 31.4 | | 107 | 186 | C 107 N 186 I |
| B2.1-86* | 0.1372 | 31.5 | 607 | 80 | 107 | C 80 N 107 I |
| B2.1-87* | 0.1116 | 30.6 | 473 | 89 | 59*** | C 89 N (83) I |
| B2.1-88* | 0.2125 | 59.4 | | 121 | 269 | C 121 N 269 |

*The parameters Δn, Δε and γ₁ are determined by measurement of a mixture of 10% by weight of the compound in the host ZLI-4792 (Merck KGaA, Darmstadt) followed by extrapolation.
**The parameters Δn, Δε and γ₁ are determined with 5% by weight of the compound in ZLI-4792.
***The clearing point is determined by measurement of a mixture of 10 or 5% by weight of the compound in the host ZLI-4792 followed by extrapolation.

The entire disclosure[s] of all applications, patents and publications, cited herein and of corresponding German application No. 10324312.7, filed May 27, 2003 is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula I

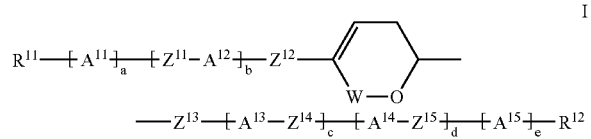

wherein
a, b, c, d and e are each, independently of one another, 0 or 1, and the sum of a+b+c+d+e is ≧1;
W is —CH₂—;
$R^{11}$ is an alkyl radical having 1 to 15 carbon atoms optionally mono- or polysubstituted, identically or differently, by halogen or —CN, wherein optionally, one or more CH₂ groups in this radical may be replaced by —C≡C—, —CH=CH—, —S—, —C(O)—O— and/or —O—C(O)— in such a way that hetero atoms O and S are not linked directly to one another;

$R^{12}$ is halogen, —CN, —NCS, aralkyl, O-aralkyl or an alkyl radical having from 1 to 15 carbon atoms optionally mono- or polysubstituted, identically or differently, by halogen or —CN, wherein optionally, one or more CH₂ groups in this radical may be replaced by —C≡C—, —CH=CH—, —O—, —S—, —C(O)—O— and/or —O—C(O)— in such a way that hetero atoms O and S are not linked directly to one another;

$Z^{11}$ is a single bond, —CH₂—, —CH₂CH₂—, —CF₂CH₂—, —CH₂CF₂—, —CF₂CF₂—, —CH=CH— or —C≡C—;

$Z^{12}$ is a single bond, —CH₂—, —CH₂CH₂—, —CF₂CH₂—, —CH₂CF₂— or —CF₂CF₂—;

$Z^{13}$, $Z^{14}$ and $Z^{15}$ are each, independently of one another, a single bond, —CH₂CH₂—, —CF₂CH₂—, —CH₂CF₂—, —CF₂CF₂—, —CH=CH—, —C≡C—, —CH₂O—, —CF₂O—, —C(O)— or —C(O)—O—;

$A^{11}$ and $A^{12}$, independently of one another, are

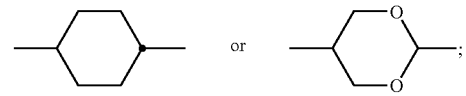

$A^{13}$ and $A^{14}$, independently of one another, are

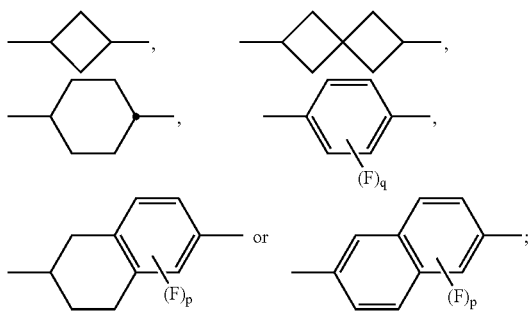

$A^{15}$ is

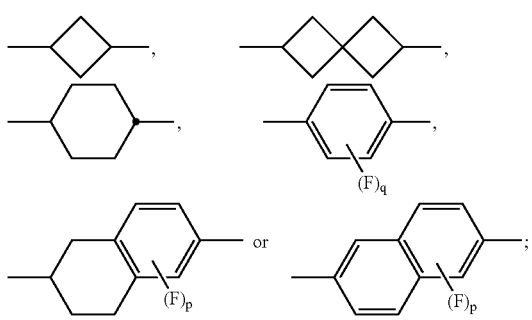

or
$A^{15}$-$R^{12}$ together are

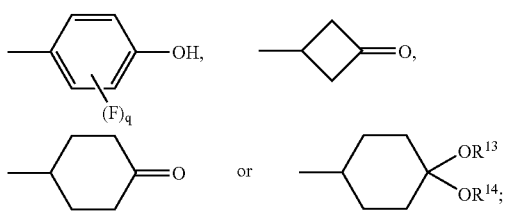

or
$Z^{13}$-[-$A^{13}$-$Z^{14}$-]$_c$-[-$A^{14}$-$Z^{15}$-]$_d$-[-$A^{15}$-]$_e$-$R^{12}$ is

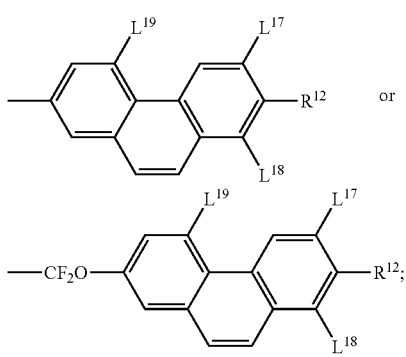

$L^{17}$, $L^{18}$ and $L^{19}$, independently of one another, are H or F;
q is 0, 1, 2, 3 or 4;
p is 0, 1, 2 or 3; and $R^{13}$ and $R^{14}$, independently of one another, are an alkanyl radical having from 1 to 7 carbon atoms or together are an alkylene bridge having from 2 to 7 carbon atoms; with the provisos that:
(a) if $Z^{13}$ is directly linked to $R^{12}$ to give —$Z^{13}$—$R^{12}$, then (i) $Z^{13}$ is not —CH$_2$O— or —CF$_2$O—, and (ii) if $Z^{13}$ is —C(=O)—O— or —C(=O)—, then $R^{12}$ is H, aralkyl, alkanyl or alkenyl;
(b) if $Z^{14}$ is directly linked to $R^{12}$ to give —$Z^{14}$—$R^{12}$, then (i) $Z^{14}$ is not —CH$_2$O— or —CF$_2$O—, and (ii) if $Z^{14}$ is —C(=O)—O— or —C(=O)—, then $R^{12}$ is H, aralkyl, alkanyl or alkenyl;
(c) if $Z^{15}$ is directly linked to $R^{12}$ to give —$Z^{15}$—$R^{12}$, then (i) $Z^{15}$ is not —CH$_2$O— or —CF$_2$O—, and (ii) if $Z^{15}$ is —C(=O)—O— or —C(=O)—, then $R^{12}$ is H, aralkyl, alkanyl or alkenyl; and
(d) $R^{11}$ is not CH$_3$ if a and b are both simultaneously zero, $Z^{12}$ and $Z^{13}$ are each a single bond, and -[-$A^{13}$-$Z^{14}$-]$_c$-[-$A^{14}$-$Z^{15}$-]$_d$-[-$A^{15}$-]$_e$-$R^{12}$ is unsubstituted phenyl;

wherein alkanyl is an unsaturated alkyl group which is optionally mono- or polysubstituted, identically or differently, by halogen or —CN.

2. A compound according to claim 1, wherein a+b+c+d+e≦3.

3. A compound according to claim 1, wherein $Z^{12}$ is a single bond.

4. A compound according to claim 1, wherein
b is 1;
$Z^{11}$ is a single bond; and
$A^{12}$ is

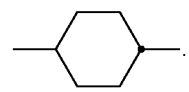

5. A compound according to claim 1, wherein
a is 1; and
$A^{11}$ is

6. A compound according to claim 1, wherein $Z^{13}$ is a single bond, —C(O)—O— or —CF$_2$O—.

7. A compound according to claim 1, wherein
e is 1;
$A^{15}$ is

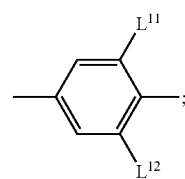

and
$L^{11}$ and $L^{12}$, independently of one another, are H or F.

8. A compound according to claim 1, wherein
e is 1; and
$A^{15}$-$R^{12}$ is

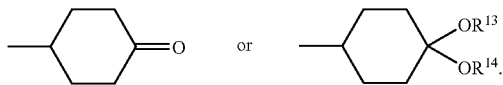

9. A compound according to claim 1, wherein
c is 1;
$Z^{14}$ is a single bond, —C(O)—O— or —CF$_2$O—;
$A^{13}$ is

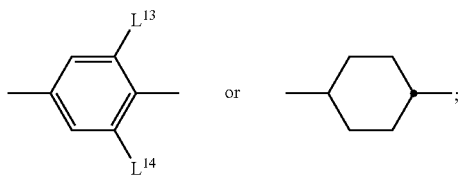

and
$L^{13}$ and $L^{14}$, independently of one another, are H or F.

10. A compound according to claim 1, wherein
d is 1;
$Z^{15}$ is —CF$_2$O—;
$A^{14}$ is

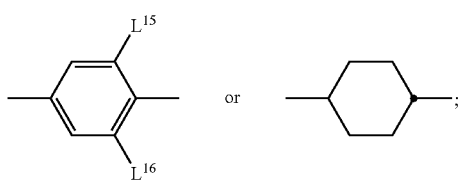

and
$L^{15}$ and $L^{16}$, independently of one another, are H or F.

11. A process for the preparation of a compound according to claim 1, comprising:
performing a metathesis ring-closing of a compound of formula II in the presence of a metathesis catalyst 12. A process according to claim 11, wherein the metathesis catalyst is a ruthenium-alkylidene complex.

13. A process according to claim 11, further comprising after the metathesis reaction step, reducing the compound of the formula I wherein W is —C(=O)— and $Z^{13}$, $Z^{14}$ and $Z^{15}$ are not —C(O)—, into a compound of the formula I, wherein W is —CH$_2$—;

$R^{11}$ is an alkyl radical having from 1 to 15 carbon atoms optionally mono- or polysubstituted, identically or differently, by halogen or —CN, optionally one or more CH$_2$ groups in this radical may be replaced by —C≡C—, —CH=CH—, and/or —S— in such a way that hetero atoms O and S are not linked directly to one another;

$R^{12}$ is H, halogen, —CN, —NCS, aralkyl, O-aralkyl or an alkyl radical having from 1 to 15 carbon atoms, optionally mono- or polysubstituted, identically or differently, by halogen or —CN, optionally one or more CH$_2$ groups in this radical may be replaced by —C≡C—, —CH=CH—, —O— and/or —S— in such a way that hetero atoms O and S are not linked directly to one another; and $Z^{13}$, $Z^{14}$ and $Z^{15}$ are each, independently of one another, a single bond, —CH$_2$CH$_2$—, —CF$_2$CH$_2$—, —CH$_2$CF$_2$—, —CF$_2$CF$_2$—, —CH=CH—, —C≡C—, —CH$_2$O— or —CF$_2$O—.

14. A process according to claim 11, further comprising, after the metathesis ring-closing reaction, catalytically hydrogenating the resultant compound to obtain a compound of formula III:

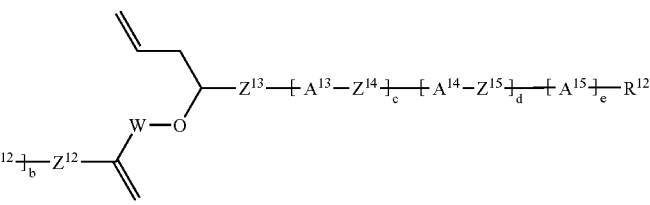

to give a compound of formula I

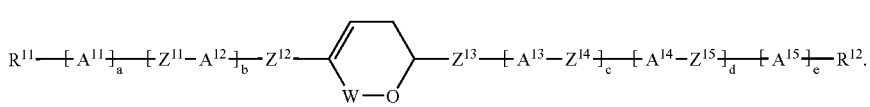

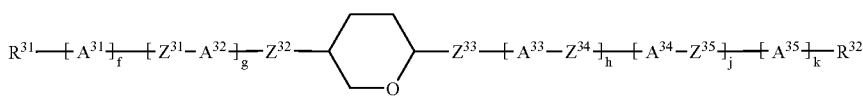 III wherein
  f, g, h, j and k are each, independently of one another, 0 or 1;
  $R^{31}$ is an alkyl radical having from 1 to 15 carbon atoms optionally mono- or polysubstituted, identically or differently, by halogen or —CN, wherein, optionally one or more $CH_2$ groups in this radical may be replaced by —S—, —C(O)—O— and/or —O—C(O)— in such a way that hetero atoms O and S are not linked directly to one another;
  $R^{32}$ is H, halogen, —CN, —NCS, aralkyl or an alkyl radical having from 1 to 15 carbon atoms optionally mono- or polysubstituted, identically or differently, by halogen or —CN, wherein optionally one or more $CH_2$ groups in this radical may be replaced by —O—, —S—, —C(O)—O— and/or —O—C(O)— in such a way that hetero atoms O and S are not linked directly to one another;
  $Z^{31}$ and $Z^{32}$, independently of one another, are a single bond, —$CH_2$—, —$CH_2CH_2$—, —$CF_2CH_2$—, —$CH_2CF_2$— or —$CF_2CF_2$—;
  $Z^{33}$, $Z^{34}$ and $Z^{35}$ are each, independently of one another, a single bond, —$CH_2CH_2$—, —$CF_2CH_2$—, —$CH_2CF_2$—, —$CF_2CF_2$—, —$CH_2O$—, —$CF_2O$—, —C(O)— or —C(O)—O—;
  $A^{31}$ and $A^{32}$, independently of one another, are

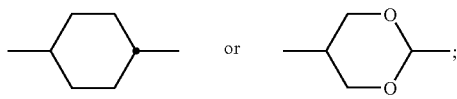

$A^{33}$ and $A^{34}$, independently of one another, are

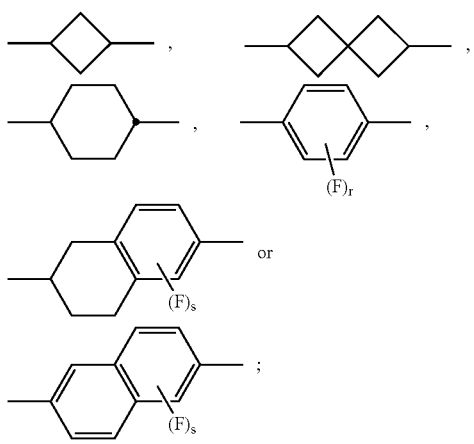

$A^{35}$ is

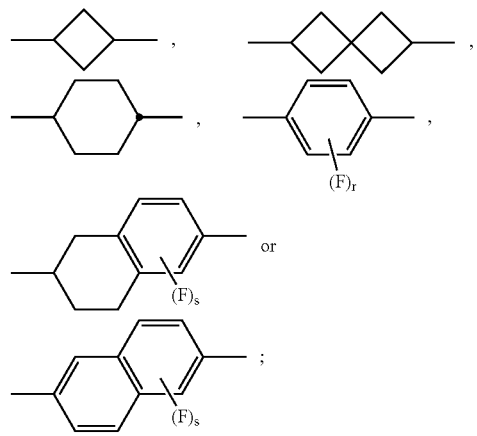

or
  $A^{35}$-$R^{32}$ together are

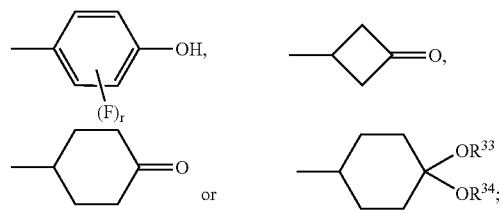

or
  $Z^{33}$-[-$A^{33}$-$Z^{34}$-]$_h$-[-$A^{34}$-$Z^{35}$-]$_j$-[-$A^{35}$-]$_k$-$R^{32}$ is

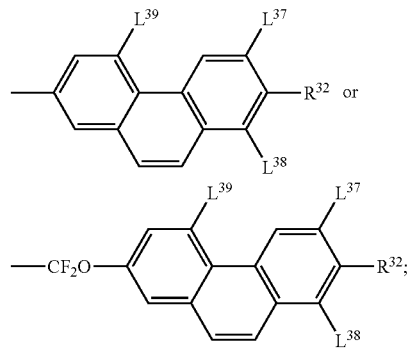

$L^{37}$, $L^{38}$ and $L^{39}$, independently of one another, are H or F;
  r is 0, 1, 2, 3 or 4;
  s is 0, 1, 2 or 3; and
  $R^{33}$ and $R^{34}$, independently of one another, are an alkanyl radical having from 1 to 7 carbon atoms or together are an alkylene bridge having from 2 to 7 carbon atoms;

with the provisos:

that, in the case of direct linking of $Z^{33}$ and $R^{32}$ to give —$Z^{33}$—$R^{32}$, $R^{32}$ is H, aralkyl or alkanyl if $Z^{33}$ is —C(=O)—, $R^{32}$ is aralkyl or alkanyl if $Z^{33}$ is —C(=O)—O—, and $Z^{33}$ is not —CH$_2$O— or —CF$_2$O—;

that, in the case of direct linking of $Z^{34}$ and $R^{32}$ to give —$Z^{34}$—$R^{32}$, $R^{32}$ is H, aralkyl or alkanyl if $Z^{34}$ is —C(=O)—, $R^{32}$ is aralkyl or alkanyl if $Z^{34}$ is —C(=O)—O—, and $Z^{34}$ is not —CH$_2$O— or —CF$_2$O—;

that, in the case of direct linking of $Z^{35}$ and $R^{32}$ to give —$Z^{35}$—$R^{32}$, $R^{32}$ is H, aralkyl or alkanyl if $Z^{35}$ is —C(=O)—, $R^{32}$ is aralkyl or alkanyl if $Z^{35}$ is —C(=O)—O—, and $Z^{35}$ is not —CH$_2$O— or —CF$_2$O—;

wherein alkanyl is an unsaturated alkyl group which is optionally mono- or polysubstituted, identically or differently, by halogen or —CN.

15. A process according to claim 11, further comprising, before the metathesis ring-closing, reacting a compound of the formula IV with a homoallyl compound of formula V

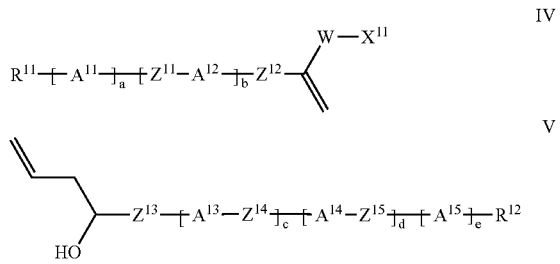

to form a compound of formula II

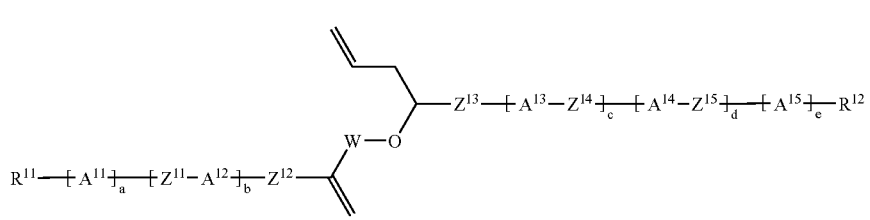

wherein $X^{11}$ is a leaving group.

16. A process according to claim 15, wherein

W is —CH$_2$—; and $X^{11}$ is chlorine, bromine, iodine or a sulfonic acid radical.

17. An allyl compound of the formula IV-Bb

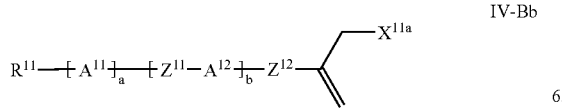

wherein a is zero and b is 1 or a is 1 and b is zero or a and b are both 1;

$X^{11a}$ is chlorine, bromine, iodine, a sulfonic acid radical, —OH, alkoxy or O-aralkyl, or —$X^{11a}$ is =O;

$R^{11}$ is H, an alkyl radical having from 1 to 15 carbon atoms optionally mono- or polysubstituted, identically or differently, by halogen or —CN, wherein optionally one or more CH$_2$ groups in this radical may be replaced by —C≡C—, —CH=CH—, —O—, —S—, —C(O)—O— and/or —O—C(O)— in such a way that hetero atoms O and S are not linked directly to one another;

$Z^{11}$ is a single bond, —CH$_2$—, —CH$_2$CH$_2$—, —CF$_2$CH$_2$—, —CH$_2$CF$_2$—, —CF$_2$CF$_2$—, —CH=CH— or —C≡C—;

$Z^{12}$ is a single bond, —CH$_2$—, —CH$_2$CH$_2$—, —CF$_2$CH$_2$—, —CH$_2$CF$_2$— or —CF$_2$CF$_2$—; and $A^{11}$ and $A^{12}$, independently of one another, are

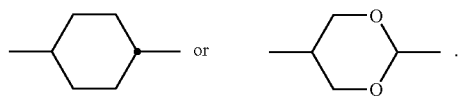

18. An electro-optical display device, comprising a liquid crystalline medium, in turn comprising a compound according to claim 1.

19. An allyl compound according to claim 17, wherein $A^{11}$ and $A^{12}$ are 1,4-cyclohexylene.

20. An electro-optical display device, comprising a liquid-crystalline medium, in turn comprising a compound made by the process of claim 14.

21. A process according to claim 13, further comprising, after the metathesis ring-closing reaction and the reduction reaction, catalytically hydrogenating the resultant compound to obtain a compound of formula III:

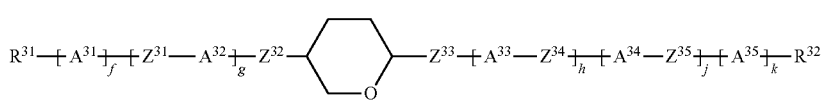

wherein
- f, g, h, j and k are each, independently of one another, 0 or 1;
- $R^{31}$ is an alkyl radical having from 1 to 15 carbon atoms optionally mono- or polysubstituted, identically or differently, by halogen or —CN, wherein, optionally one or more $CH_2$ groups in this radical may be replaced by —S—, —C(O)—O— and/or —O—C(O)— in such a way that hetero atoms O and S are not linked directly to one another;
- $R^{32}$ is H, halogen, —CN, —NCS, aralkyl or an alkyl radical having from 1 to 15 carbon atoms optionally mono- or polysubstituted, identically or differently, by halogen or —CN, wherein optionally one or more $CH_2$ groups in this radical may be replaced by —O—, —S—, —C(O)—O— and/or —O—C(O)— in such a way that hetero atoms O and S are not linked directly to one another;
- $Z^{31}$ and $Z^{32}$, independently of one another, are a single bond, —$CH_2$—, —$CH_2CH_2$—, —$CF_2CH_2$—, —$CH_2CF_2$— or —$CF_2CF_2$—;
- $Z^{33}$, $Z^{34}$ and $Z^{35}$ are each, independently of one another, a single bond, —$CH_2CH_2$—, —$CF_2CH_2$—, —$CH_2CF_2$—, —$CF_2CF_2$—, —$CH_2O$—, —$CF_2O$—, —C(O)— or —C(O)—O—;
- $A^{31}$ and $A^{32}$, independently of one another, are

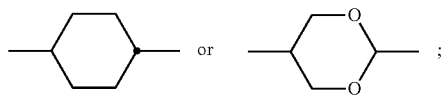

- $A^{33}$ and $A^{34}$, independently of one another, are

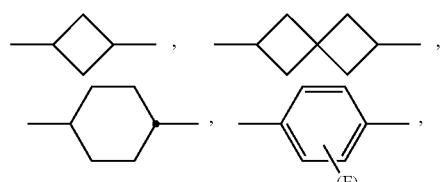

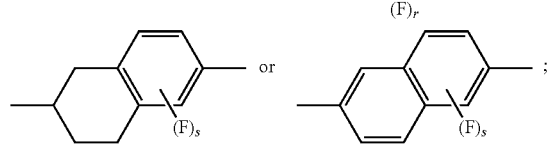

- $A^{35}$ is

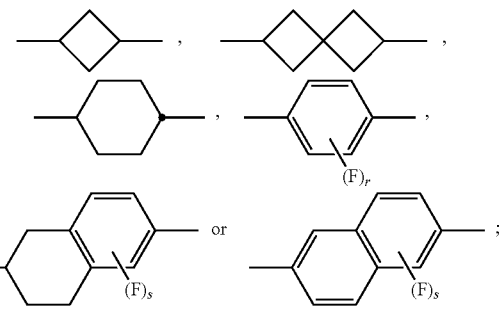

or
- $A^{35}$-$R^{32}$ together are

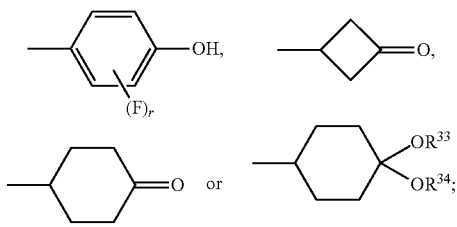

or
- $Z^{33}$-[-$A^{33}$-$Z^{34}$-]$_h$-[-$A^{34}$-$Z^{35}$-]$_j$-[-$A^{35}$-]$_k$-$R^{32}$ is

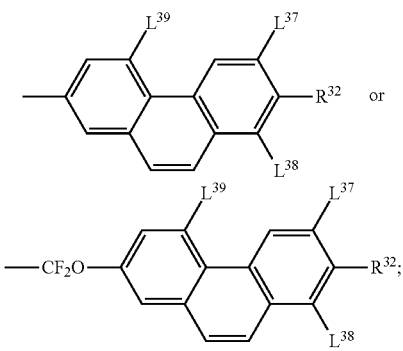

- $L^{37}$, $L^{38}$ and $L^{39}$, independently of one another, are H or F;
- r is 0, 1, 2, 3 or 4;
- s is 0, 1, 2 or 3; and
- $R^{33}$ and $R^{34}$, independently of one another, are an alkanyl radical having from 1 to 7 carbon atoms or together are an alkylene bridge having from 2 to 7 carbon atoms;

with the provisos:

that, in the case of direct linking of $Z^{33}$ and $R^{32}$ to give —$Z^{33}$—$R^{32}$, $R^{32}$ is H, aralkyl or alkanyl if $Z^{33}$ is —C(=O)—, $R^{32}$ is aralkyl or alkanyl if $Z^{33}$ is —C(=O)—O—, and $Z^{33}$ is not —CH$_2$O— or —CF$_2$O—;

that, in the case of direct linking of $Z^{34}$ and $R^{32}$ to give —$Z^{34}$—$R^{32}$, $R^{32}$ is H, aralkyl or alkanyl if $Z^{34}$ is —C(=O)—, $R^{32}$ is aralkyl or alkanyl if $Z^{34}$ is —C(=O)—O—, and $Z^{34}$ is not —CH$_2$O— or —CF$_2$O—;

that, in the case of direct linking of $Z^{35}$ and $R^{32}$ to give —$Z^{35}$—$R^{32}$, $R^{32}$ is H, aralkyl or alkanyl if $Z^{35}$ is —C(=O)—, $R^{32}$ is aralkyl or alkanyl if $Z^{35}$ is —C(=O)—O—, and $Z^{35}$ is not —CH$_2$O— or —CF$_2$O—;

wherein alkanyl is an unsaturated alkyl group which is optionally mono- or polysubstituted identically or differently, by halogen or —CN.

22. A compound according to claim 1, wherein $Z^{12}$ is a single bond, and (a) a and b are 0, (b) a is 1 and b is 0, or (c) a is 0 and b is 1.

23. A compound according to claim 22, wherein a is 0, b is 0, and $R^{11}$ is alkanyl.

24. A compound according to claim 4, wherein $Z^{12}$ is a single bond.

25. A compound according to claim 10, wherein said compound is of Formula I-S

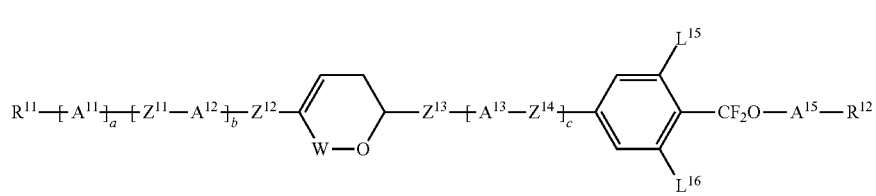

and $A^{15}$ is

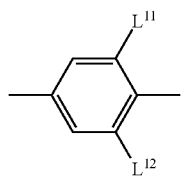

and $Z^{13}$ is a single bond.

26. A compound according to claim 10, wherein c is 1, $Z^{14}$ is a single bond, and $A^{13}$ is

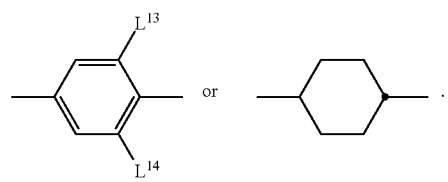

27. A compound according to claim 25, wherein c is 1, $Z^{14}$ is a single bond, and $A^{13}$ is

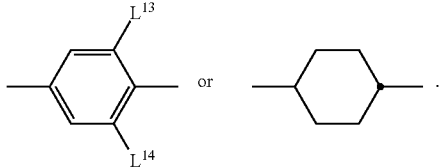

28. A compound according to claim 10, wherein said compound is of formulae I-SBA or I-SBB:

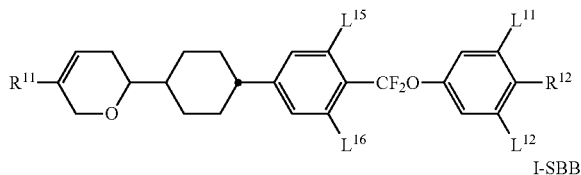

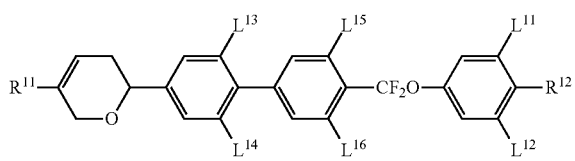

wherein $L^{13}$, $L^{14}$, $L^{15}$ and $L^{16}$ are each, independently of one another, H or F.

29. A compound according to claim 28, wherein $R^{11}$ is a straight-chain alkenyl or alkanyl radical having 1-7 carbon atoms, and $R^2$ is halogen or an unbranched alkanyl or alkoxy radical having 1-5 carbon atoms which is optionally mono- or polysubstituted by halogen.

30. A compound according to claim 28, wherein said compound is of formula I-SBB:

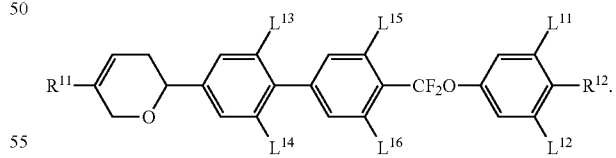

31. A compound according to claim 28, wherein said compound is of formula I-SBBIa:

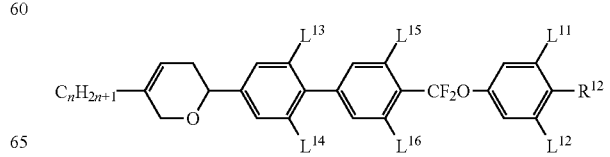

and n is 1, 2, 3, 4, 5, 6 or 7.

32. A compound according to claim 31, wherein n is 1-5, $R^{12}$ is F, $CF_3$, $OCF_3$, $OCHF_2$, or CN, and $L^{14}$ is H.

33. A compound of formula I

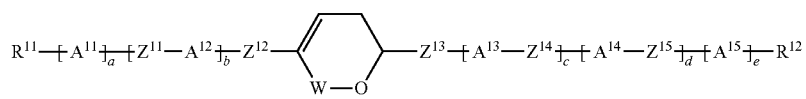

I wherein
- a, b, c, d and e are each, independently of one another, 0 or 1, and the sum of a+b+c+d+e is $\geq 1$;
- W is $-CH_2-$ or $-C(=O)-$;
- $R^{11}$ is an alkyl radical having 1 to 15 carbon atoms optionally mono- or polysubstituted, identically or differently, by halogen or —CN, wherein optionally, one or more $CH_2$ groups in this radical may be replaced by $-C\equiv C-$, $-CH=CH-$, $-S-$, $-C(O)-O-$ and/or $-O-C(O)-$ in such a way that hetero atoms O and S are not linked directly to one another;
- $R^{12}$ is H, halogen, —CN, —NCS, aralkyl, O-aralkyl or an alkyl radical having from 1 to 15 carbon atoms optionally mono- or polysubstituted, identically or differently, by halogen or —CN, wherein optionally, one or more $CH_2$ groups in this radical may be replaced by $-C\equiv C-$, $-CH=CH-$, $-O-$, $-S-$, $-C(O)-O-$ and/or $-O-C(O)-$ in such a way that hetero atoms O and S are not linked directly to one another;
- $Z^{11}$ is a single bond, $-CH_2-$, $-CH_2CH_2-$, $-CF_2CH_2-$, $-CH_2CF_2-$, $-CF_2CF_2-$, $-CH=CH-$ or $-C\equiv C-$;
- $Z^{12}$ is a single bond, $-CH_2-$, $-CH_2CH_2-$, $-CF_2CH_2-$, $-CH_2CF_2-$ or $-CF_2CF_2-$;
- $Z^{13}$, $Z^{14}$ and $Z^{15}$ are each, independently of one another, a single bond, $-CH_2CH_2-$, $-CF_2CH_2-$, $-CH_2CF_2-$, $-CF_2CF_2-$, $-CH=CH-$, $-C\equiv C-$, $-CH_2O-$, $-CF_2O-$, $-C(O)-$ or $-C(O)-O-$;
- $A^{11}$ and $A^{12}$, independently of one another, are

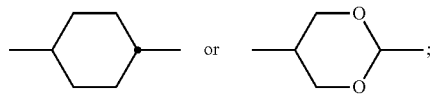

- $A^{13}$ and $A^{14}$, independently of one another, are

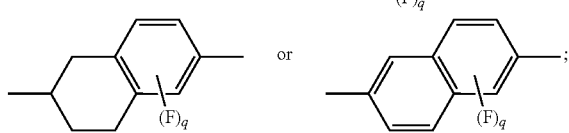

- $A^{15}$ is

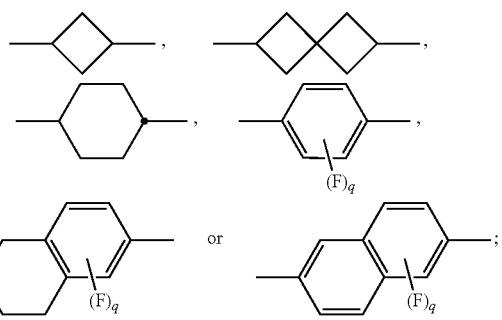

or

- $A^{15}$-$R^{12}$ together are

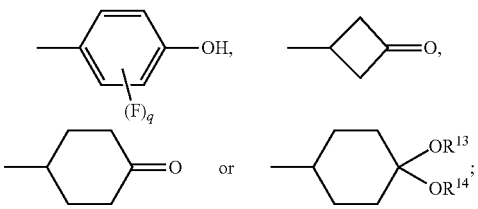

or $Z^{13}$-[-$A^{13}$-$Z^{14}$-$]_c$[-$A^{14}$-$Z^{15}$-$]_d$-[-$A^{15}$-$]_e$-$R^{12}$ is

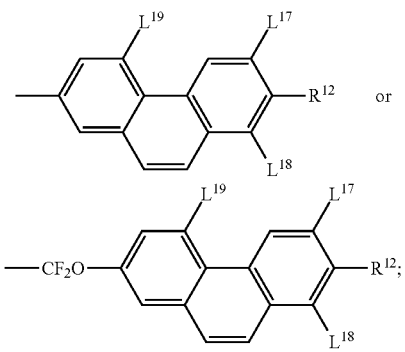

$L^{17}$, $L^{18}$ and $L^{19}$, independently of one another, are H or F;

q is 0, 1, 2, 3 or 4;

p is 0, 1, 2 or 3; and $R^{13}$ and $R^{14}$, independently of one another, are an alkanyl radical having from 1 to 7 carbon atoms or together are an alkylene bridge having from 2 to 7 carbon atoms;

with the provisos that:
(a) if $Z^{13}$ is directly linked to $R^{12}$ to give —$Z^{13}$—$R^{12}$, then
   (i) $Z^{13}$ is not —$CH_2O$— or —$CF_2O$—, and (ii) if $Z^{13}$ is —C(=O)—O— or —C(=O)—, then $R^{12}$ is H, aralkyl, alkanyl or alkenyl;
(b) if $Z^{14}$ is directly linked to $R^{12}$ to give —$Z^{14}$—$R^{12}$, then
   (i) $Z^{14}$ is not —$CH_2O$— or —$CF_2O$—, and (ii) if $Z^{14}$ is —C(=O)—O— or —C(=O)—, then $R^{12}$ is H, aralkyl, alkanyl or alkenyl;
(c) if $Z^{15}$ is directly linked to $R^{12}$ to give —$Z^{15}$—$R^{12}$, then
   (i) $Z^{15}$ is not —$CH_2O$— or —$CF_2O$—, and (ii) if $Z^{15}$ is —C(=O)—O— or —C(=O)—, then $R^{12}$ is H, aralkyl, alkanyl or alkenyl; and
(d) $R^{11}$ is not $CH_3$ if a and b are both simultaneously zero, $Z^{12}$ and $Z^{13}$ are each a single bond, W is —$CH_2$—, and -[-$A^{13}$-$Z^{14}$-]$_c$-[-$A^{14}$-$Z^{15}$-]$_d$-[-$A^{15}$-]$_e$—$R^{12}$ is unsubstituted phenyl;

wherein alkanyl is an unsaturated alkyl group which is optionally mono- or polysubstituted, identically or differently, by halogen or —CN.

34. A compound according to claim 33, wherein a+b+c+d+e is greater than or equal to 1 and less than or equal to 3.

35. A compound according to claim 33, wherein b is 1, $Z^{11}$ is a single bond, and $A^{12}$ is 1,4-cyclohexylene.

36. A compound according to claim 33, wherein a is 1, and $A^{11}$ is 1,4-cyclohexylene.

37. A compound according to claim 33, wherein c is 1; $Z^{14}$ is a single bond, —C(O)—O— or —$CF_2O$—; $A^{13}$ is

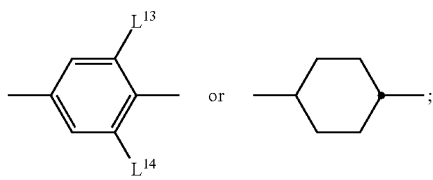

and $L^{13}$ and $L^{14}$, independently of one another, are H or F.

38. A compound according to claim 33, wherein d is 1; $Z^{15}$ is —$CF_2O$—; $A^{14}$ is

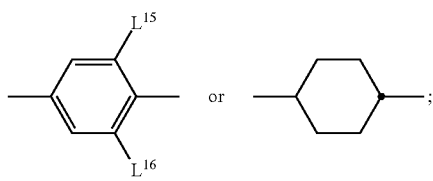

and $L^{15}$ and $L^{16}$, independently of one another, are H or F.

39. A compound of formula I

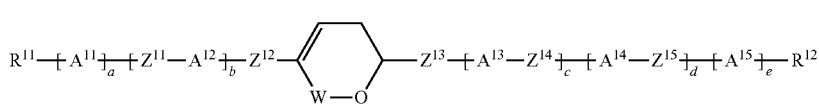

wherein
a, b, c, d and e are each, independently of one another, 0 or 1, and the sum of a+b+c+d+e is $\geq 1$;
W is —$CH_2$— or —C(=O)—;
$R^{11}$ is an alkyl radical having 1 to 15 carbon atoms optionally mono- or polysubstituted, identically or differently, by halogen or —CN, wherein optionally, one or more $CH_2$ groups in this radical may be replaced by —C≡C—, —CH=CH—, —S—, —C(O)—O— and/or —O—C(O)— in such a way that hetero atoms O and S are not linked directly to one another;

$R^{12}$ is halogen, —CN, —NCS, aralkyl, O-aralkyl or an alkyl radical having from 1 to 15 carbon atoms optionally mono- or polysubstituted, identically or differently, by halogen or —CN, wherein optionally, one or more $CH_2$ groups in this radical may be replaced by —C≡C—, —CH=CH—, —O—, —S—, —C(O)—O— and/or —O—C(O)— in such a way that hetero atoms O and S are not linked directly to one another;

$Z^{11}$ is a single bond, —$CH_2$—, —$CH_2CH_2$—, —$CF_2CH_2$—, —$CH_2CF_2$—, —$CF_2CF_2$—, —CH=CH— or —C≡C—;

$Z^{12}$ is a single bond, —$CH_2$—, —$CH_2CH_2$—, —$CF_2CH_2$—, —$CH_2CF_2$— or —$CF_2CF_2$—;

$Z^{13}$, $Z^{14}$ and $Z^{15}$ are each, independently of one another, a single bond, —$CH_2CH_2$—, —$CF_2CH_2$—, —$CH_2CF_2$—, —$CF_2CF_2$—, —CH=CH—, —C≡C—, —$CH_2O$—, —$CF_2O$—, —C(O)— or —C(O)—O—;

$A^{11}$ and $A^{12}$, independently of one another, are

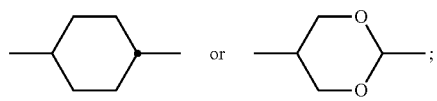

$A^{13}$ and $A^{14}$, independently of one another, are

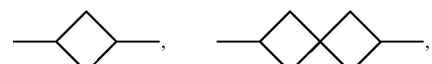

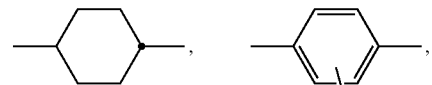

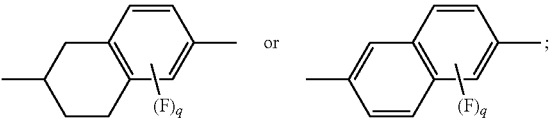

$A^{15}$ is

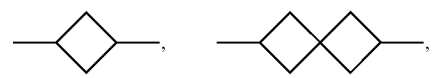

-continued

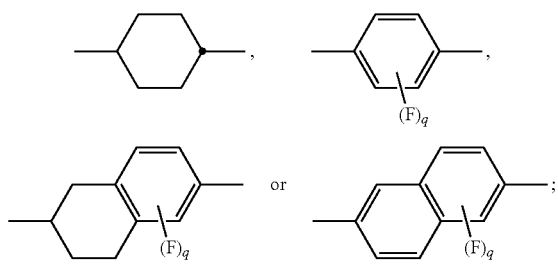

or $A^{15}$-$R^{12}$ together are

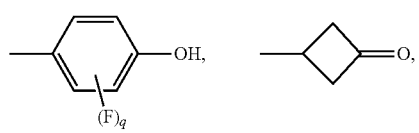

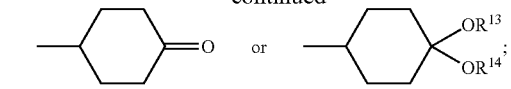

or
$Z^{13}$-[-$A^{13}$-$Z^{14}$-]$_c$-[-$A^{14}$-$Z^{15}$-]$_d$-[-$A^{15}$-]$_e$-$R^{12}$ is

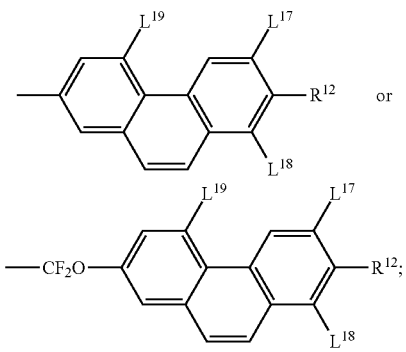

$L^{17}$, $L^{18}$ and $L^{19}$, independently of one another, are H or F;
q is 0, 1, 2, 3 or 4;
p is 0, 1, 2 or 3; and
$R^{13}$ and $R^{14}$, independently of one another, are an alkanyl radical having from 1 to 7 carbon atoms or together are an alkylene bridge having from 2 to 7 carbon atoms;
with the provisos that:
(a) if $Z^{13}$ is directly linked to $R^{12}$ to give —$Z^{13}$—$R^{12}$, then (i) $Z^{13}$ is not —CH$_2$O— or —CF$_2$O—, and (ii) if $Z^{13}$ is —C(=O)—O— or —C(=O)—, then $R^{12}$ is H, aralkyl, alkanyl or alkenyl;

(b) if $Z^{14}$ is directly linked to $R^{12}$ to give —$Z^{14}$—$R^{12}$, then (i) $Z^{24}$ is not —CH$_2$O— or —CF$_2$O—, and (ii) if $Z^{14}$ is —C(=O)—O— or —C(=O)—, then $R^{12}$ is H, aralkyl, alkanyl or alkenyl;
(c) if $Z^{15}$ is directly linked to $R^{12}$ to give —$Z^{15}$—$R^{12}$, then (i) $Z^{15}$ is not —CH$_2$O— or —CF$_2$O—, and (ii) if $Z^{15}$ is —C(=O)—O— or —C(=O)—, then $R^{12}$ is H, aralkyl, alkanyl or alkenyl; and
(d) $R^{11}$ is not CH$_3$ if a and b are both simultaneously zero, $Z^{12}$ and $Z^{13}$ are each a single bond, W is —CH$_2$—, and -[-$A^{13}$-$Z^{14}$-]$_c$-[-$A^{14}$-$Z^{15}$-]$_d$-[-$A^{15}$-]$_e$-$R^{12}$ is unsubstituted phenyl;

wherein alkanyl is an unsaturated alkyl group which is optionally mono- or polysubstituted, identically or differently, by halogen or —CN.

40. A compound according to claim 39, wherein $R^{12}$ is halogen, an unbranched alkanyl having from 1 to 5 carbon atoms which is optionally mono- or polysubstituted by halogen, or alkoxy having from 1 to 5 carbon atoms which is optionally mono- or polysubstituted by halogen.

41. A compound of formula I

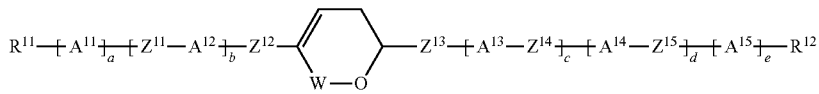

I wherein
a is 1 and b is 0, or a is 0, and b is 1;
c, d and e are each, independently of one another, 0 or 1;
W is —CH$_2$— or —C(=O)—;
$R^{11}$ is an alkyl radical having 1 to 15 carbon atoms optionally mono- or polysubstituted, identically or differently, by halogen or —CN, wherein optionally, one or more CH$_2$ groups in this radical may be replaced by —C≡C—, —CH=CH—, —S—, —C(O)—O— and/or —O—C(O)— in such a way that hetero atoms O and S are not linked directly to one another;
$R^{12}$ is halogen, —CN, —NCS, aralkyl, O-aralkyl or an alkyl radical having from 1 to 15 carbon atoms optionally mono- or polysubstituted, identically or differently, by halogen or —CN, wherein optionally, one or more CH$_2$ groups in this radical may be replaced by —C≡C—, —CH=CH—, —O—, —S—, —C(O)—O— and/or —O—C(O)— in such a way that hetero atoms O and S are not linked directly to one another;
$Z^{11}$ is a single bond, —CH$_2$—, —CH$_2$CH$_2$—, —CF$_2$CH$_2$—, —CH$_2$CF$_2$—, —CF$_2$CF$_2$—, —CH=CH— or —C≡C—;
$Z^{12}$ is a single bond, —CH$_2$—, —CH$_2$CH$_2$—, —CF$_2$CH$_2$—, —CH$_2$CF$_2$— or —CF$_2$CF$_2$—;
$Z^{13}$, $Z^{14}$ and $Z^{15}$ are each, independently of one another, a single bond, —CH$_2$CH$_2$—, —CF$_2$CH$_2$—, —CH$_2$CF$_2$—, —CF$_2$CF$_2$—, —CH=CH—, —C≡C—, —CH$_2$O—, —CF$_2$O—, —C(O)— or —C(O)—O—;

$A^{11}$ and $A^{12}$, independently of one another, are

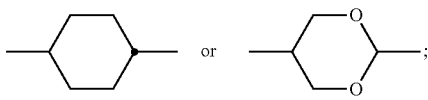

$A^{13}$ and $A^{14}$, independently of one another, are

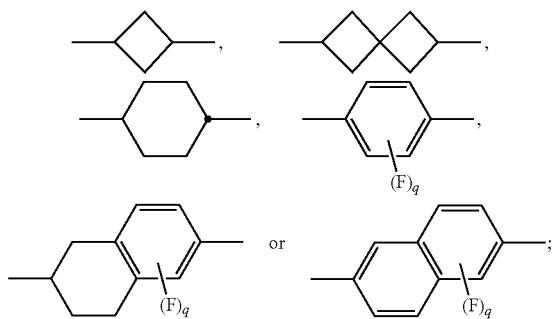

$A^{15}$ is

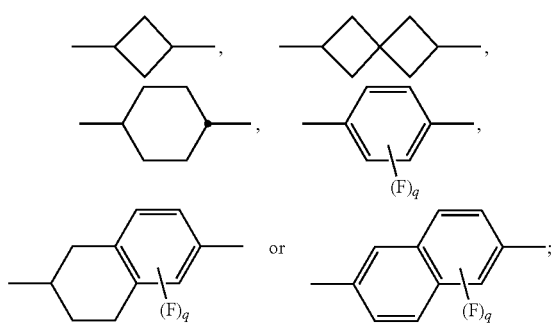

$A^{15}$-$R^{12}$ together are

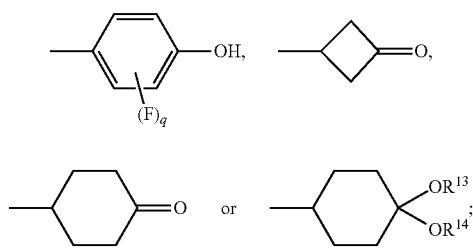

or
$Z^{13}\text{-}[\text{-}A^{13}\text{-}Z^{14}\text{-}]_c\text{-}[\text{-}A^{14}\text{-}Z^{15}\text{-}]_d\text{-}[\text{-}A^{15}\text{-}]_e\text{-}R^{12}$ is

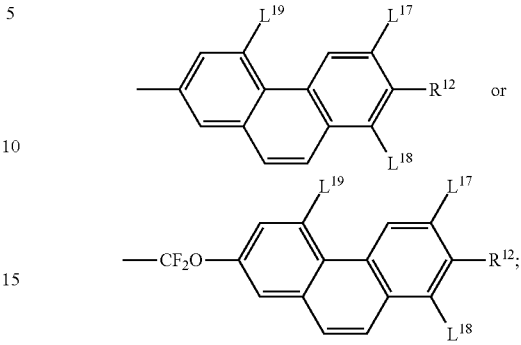

$L^{17}$, $L^{18}$ and $L^{19}$, independently of one another, are H or F;
q is 0, 1, 2, 3 or 4;
p is 0, 1, 2 or 3; and
$R^{13}$ and $R^{14}$, independently of one another, are an alkanyl radical having from 1 to 7 carbon atoms or together are an alkylene bridge having from 2 to 7 carbon atoms;
with the provisos that:
(a) if $Z^{13}$ is directly linked to $R^{12}$ to give —$Z^{13}$—$R^{12}$, then (i) $Z^{13}$ is not —$CH_2O$— or —$CF_2O$—, and (ii) if $Z^{13}$ is —C(=O)—O— or —C(=O)—, then $R^{12}$ is H, aralkyl, alkanyl or alkenyl;
(b) if $Z^{14}$ is directly linked to $R^{12}$ to give —$Z^{14}$—$R^{12}$, then (i) $Z^{14}$ is not —$CH_2O$— or —$CF_2O$—, and (ii) if $Z^{14}$ is —C(=O)—O— or —C(=O)—, then $R^{12}$ is H, aralkyl, alkanyl or alkenyl;
(c) if $Z^{15}$ is directly linked to $R^{12}$ to give —$Z^{15}$—$R^{12}$, then (i) $Z^{15}$ is not —$CH_2O$— or —$CF_2O$—, and (ii) if $Z^{15}$ is —C(=O)—O— or —C(=O)—, then $R^{12}$ is H, aralkyl, alkanyl or alkenyl; and
(d) $R^{11}$ is not $CH_3$ if a and b are both simultaneously zero, $Z^{12}$ and $Z^{13}$ are each a single bond, W is —$CH_2$—, and -[-$A^{13}$-$Z^{14}$-]$_c$-[-$A^{14}$-$Z^{15}$-]$_d$-[-$A^{15}$-]$_e$—$R^{12}$ is unsubstituted phenyl;

wherein alkanyl is an unsaturated alkyl group which is optionally mono- or polysubstituted, identically or differently, by halogen or —CN.

42. A compound according to claim 41, wherein W is —C(=O)—.

43. A compound according to claim 41, wherein W is —$CH_2$—.

44. A process for the preparation of a compound according to claim 41, comprising:
performing a metathesis ring-closing of a compound of formula II in the presence of a metathesis catalyst

II

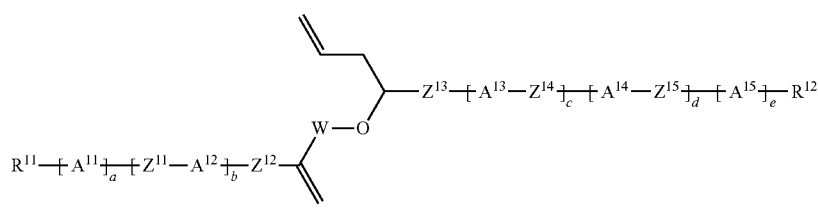

to give a compound of formula I

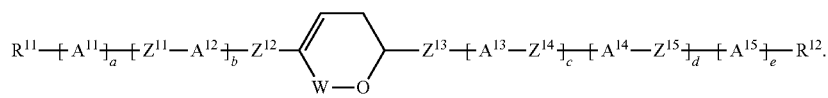

45. A process according to claim 44, wherein the metathesis catalyst is a ruthenium-alkylidene complex.

46. A process according to claim 44, further comprising after the metathesis reaction step, reducing the compound of the formula I wherein W is —C(=O)— and $Z^{13}$, $Z^{14}$ and $Z^{15}$ are not —C(O)—, into a compound of the formula I, wherein W is —CH$_2$—;
   $R^{11}$ is an alkyl radical having from 1 to 15 carbon atoms optionally mono- or polysubstituted, identically or differently, by halogen or —CN, optionally one or more CH$_2$ groups in this radical may be replaced by —C≡C—, —CH=CH—, and/or —S— in such a way that hetero atoms O and S are not linked directly to one another;
   $R^{12}$ is H, halogen, —CN, —NCS, aralkyl, O-aralkyl or an alkyl radical having from 1 to 15 carbon atoms, optionally mono- or polysubstituted, identically or differently, by halogen or —CN, optionally one or more CH$_2$ groups in this radical may be replaced by —C≡C—, —CH=CH—, —O— and/or —S— in such a way that hetero atoms O and S are not linked directly to one another; and
   $Z^{13}$, $Z^{14}$ and $Z^{15}$ are each, independently of one another, a single bond, —CH$_2$CH$_2$—, —CF$_2$CH$_2$—, —CH$_2$CF$_2$—, —CF$_2$CF$_2$—, —CH=CH—, —C≡C—, —CH$_2$O— or —CF$_2$O—.

47. A process according to claim 44, further comprising, after the metathesis ring-closing reaction, catalytically hydrogenating the resultant compound to obtain a compound of formula III:

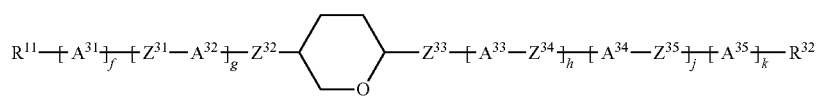

wherein
   f, g, h, j and k are each, independently of one another, 0 or 1;
   $R^{31}$ is an alkyl radical having from 1 to 15 carbon atoms optionally mono- or polysubstituted, identically or differently, by halogen or —CN, wherein, optionally one or more CH$_2$ groups in this radical may be replaced by —S—, —C(O)—O— and/or —O—C(O)— in such a way that hetero atoms O and S are not linked directly to one another;
   $R^{32}$ is H, halogen, —CN, —NCS, aralkyl or an alkyl radical having from 1 to 15 carbon atoms optionally mono- or polysubstituted, identically or differently, by halogen or —CN, wherein optionally one or more CH$_2$ groups in this radical may be replaced by —O—, —S—, —C(O)—O— and/or —O—C(O)— in such a way that hetero atoms O and S are not linked directly to one another;

$Z^{31}$ and $Z^{32}$, independently of one another, are a single bond, —CH$_2$—, —CH$_2$CH$_2$—, —CF$_2$CH$_2$—, —CH$_2$CF$_2$— or —CF$_2$CF$_2$—;
$Z^{33}$, $Z^{34}$ and $Z^{35}$ are each, independently of one another, a single bond, —CH$_2$CH$_2$—, —CF$_2$CH$_2$—, —CH$_2$CF$_2$—, —CF$_2$CF$_2$—, —CH$_2$O—, —CF$_2$O—, —C(O)— or —C(O)—O—;
$A^{31}$ and $A^{32}$, independently of one another, are

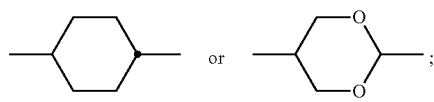

$A^{33}$ and $A^{34}$, independently of one another, are

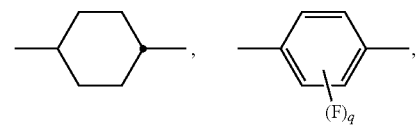

-continued

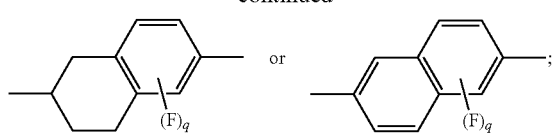

$A^{35}$ is

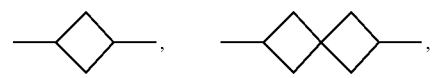

-continued

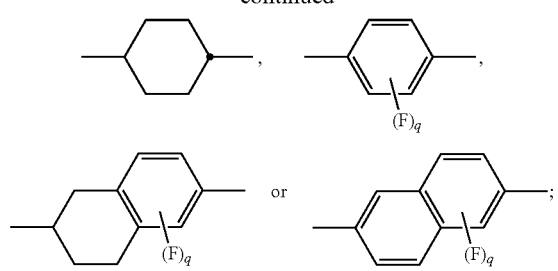

or $A^{35}R^{32}$ together are

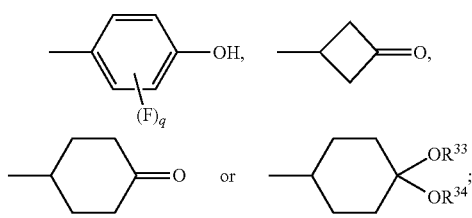

or $Z^{33}\text{-}[\text{-}A^{33}\text{-}Z^{34}\text{-}]_h\text{-}[\text{-}A^{34}\text{-}Z^{35}\text{-}]_j\text{-}[\text{-}A^{35}\text{-}]_k\text{-}R^{32}$ is

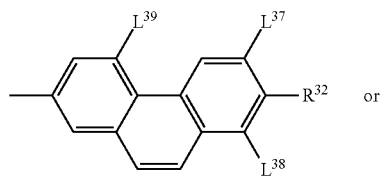

-continued

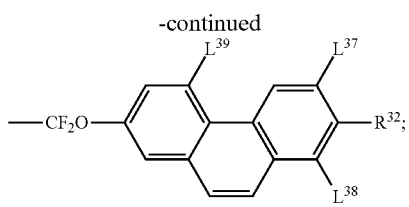

$L^{37}$, $L^{38}$ and $L^{39}$, independently of one another, are H or F;
r is 0, 1, 2, 3 or 4;
s is 0, 1, 2 or 3; and
$R^{33}$ and $R^{34}$, independently of one another, are an alkanyl radical having from 1 to 7 carbon atoms or together are an alkylene bridge having from 2 to 7 carbon atoms;

with the provisos:
that, in the case of direct linking of $Z^{33}$ and $R^{32}$ to give $-Z^{33}-R^{32}$, $R^{32}$ is H, aralkyl or alkanyl if $Z^{33}$ is $-C(=O)-$, $R^{32}$ is aralkyl or alkanyl if $Z^{33}$ is $-C(=O)-O-$, and $Z^{33}$ is not $-CH_2O-$ or $-CF_2O-$;
that, in the case of direct linking of $Z^{34}$ and $R^{32}$ to give $-Z^{34}-R^{32}$, $R^{32}$ is H, aralkyl or alkanyl if $Z^{34}$ is $-C(=O)-$, $R^{32}$ is aralkyl or alkanyl if $Z^{34}$ is $-C(=O)-O-$, and $Z^{34}$ is not $-CH_2O-$ or $-CF_2O-$;
that, in the case of direct linking of $Z^{35}$ and $R^{32}$ to give $-Z^{35}-R^{32}$, $R^{32}$ is H, aralkyl or alkanyl if $Z^{35}$ is $-C(=O)-$, $R^{32}$ is aralkyl or alkanyl if $Z^{35}$ is $-C(=O)-O-$, and $Z^{35}$ is not $-CH_2O-$ or $-CF_2O-$;
wherein alkanyl is an unsaturated alkyl group which is optionally mono- or polysubstituted, identically or differently, by halogen or $-CN$.

48. A process according to claim 44, further comprising, before the metathesis ring-closing, reacting a compound of the formula IV with a homoallyl compound of formula V

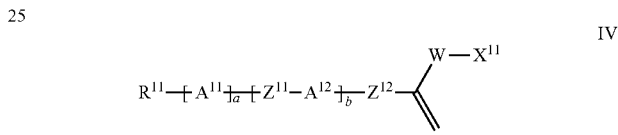

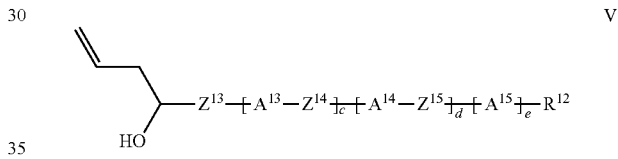

to form a compound of formula II

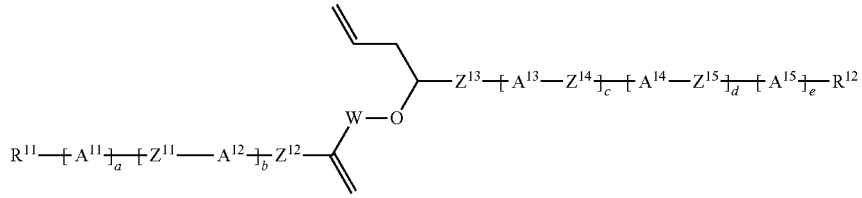

wherein $X^{11}$ is a leaving group.

49. A process according to claim 48, wherein
W is $-CH_2-$; and
$X^{11}$ is chlorine, bromine, iodine or a sulfonic acid radical.

50. An electro-optical display device, comprising a liquid crystalline medium, in turn comprising a compound according to claim 44.

51. An electro-optical display device, comprising a liquid-crystalline medium, in turn comprising a compound made by the process of claim 47.

52. A process according to claim 46, further comprising, after the metathesis ring-closing reaction and the reduction reaction, catalytically hydrogenating the resultant compound to obtain a compound of formula III:

III $$R^{31}-[A^{31}]_f-[Z^{31}-A^{32}]_g-Z^{32}-\underset{O}{\bigcirc}-Z^{33}-[A^{33}-Z^{34}]_h-[A^{34}-Z^{35}]_j-[A^{35}]_k-R^{32}$$

wherein
- f, g, h, j and k are each, independently of one another, 0 or 1;
- $R^{31}$ is an alkyl radical having from 1 to 15 carbon atoms optionally mono- or polysubstituted, identically or differently, by halogen or —CN, wherein, optionally one or more $CH_2$ groups in this radical may be replaced by —S—, —C(O)—O— and/or —O—C(O)— in such a way that hetero atoms O and S are not linked directly to one another;
- $R^{32}$ is H, halogen, —CN, —NCS, aralkyl or an alkyl radical having from 1 to 15 carbon atoms optionally mono- or polysubstituted, identically or differently, by halogen or —CN, wherein optionally one or more $CH_2$ groups in this radical may be replaced by —O—, —S—, —C(O)—O— and/or —O—C(O)— in such a way that hetero atoms O and S are not linked directly to one another;
- $Z^{31}$ and $Z^{32}$, independently of one another, are a single bond, —$CH_2$—, —$CH_2CH_2$—, —$CF_2CH_2$—, —$CH_2CF_2$— or —$CF_2CF_2$—;
- $Z^{33}$, $Z^{34}$ and $Z^{35}$ are each, independently of one another, a single bond, —$CH_2CH_2$—, —$CF_2CH_2$—, —$CH_2CF_2$—, —$CF_2CF_2$—, —$CH_2O$—, —$CF_2O$—, —C(O)— or —C(O)—O—;
- $A^{31}$ and $A^{32}$, independently of one another, are cyclohexyl or 1,3-dioxane group;

- $A^{33}$ and $A^{34}$, independently of one another, are cyclobutyl, spirobicyclobutyl, cyclohexyl, fluorinated phenyl $(F)_r$, tetrahydronaphthyl $(F)_s$ or naphthyl $(F)_s$;

- $A^{35}$ is cyclobutyl, spirobicyclobutyl, cyclohexyl, fluorinated phenyl $(F)_r$, tetrahydronaphthyl $(F)_s$ or naphthyl $(F)_s$;

or
$A^{35}$-$R^{32}$ together are fluorinated phenol $(F)_r$—OH, cyclobutanone =O, cyclohexanone =O or cyclohexane-$OR^{33}$, $OR^{34}$;

or
$Z^{33}$-$[-A^{33}-Z^{34}-]_h$-$[-A^{34}-Z^{35}-]_j$-$[-A^{35}-]_k$—$R^{32}$ is phenanthrene with $L^{39}$, $L^{37}$, $R^{32}$, $L^{38}$ substituents or —$CF_3O$— phenanthrene with $L^{39}$, $L^{37}$, $R^{32}$, $L^{38}$ substituents;

- $L^{37}$, $L^{38}$ and $L^{39}$, independently of one another, are H or F;
- r is 0, 1, 2, 3 or 4;
- s is 0, 1, 2 or 3; and
- $R^{33}$ and $R^{34}$, independently of one another, are an alkanyl radical having from 1 to 7 carbon atoms or together are an alkylene bridge having from 2 to 7 carbon atoms;

with the provisos:
  that, in the case of direct linking of $Z^{33}$ and $R^{32}$ to give —$Z^{33}$—$R^{32}$, $R^{32}$ is H, aralkyl or alkanyl if $Z^{33}$ is —C(=O)—, $R^{32}$ is aralkyl or alkanyl if $Z^{33}$ is —C(=O)—O—, and $Z^{33}$ is not —$CH_2O$— or —$CF_2O$—;

that, in the case of direct linking of $Z^{34}$ and $R^{32}$ to give —$Z^{34}$—$R^{32}$, $R^{32}$ is H, aralkyl or alkanyl if $Z^{34}$ is —C(=O)—, $R^{32}$ is aralkyl or alkanyl if $Z^{34}$ is —C(=O)—O—, and $Z^{34}$ is not —$CH_2O$— or —$CF_2O$—;

that, in the case of direct linking of $Z^{35}$ and $R^{32}$ to give —$Z^{35}$—$R^{32}$, $R^{32}$ is H, aralkyl or alkanyl if $Z^{35}$ is —C(=O)—, $R^{32}$ is aralkyl or alkanyl if $Z^{35}$ is —C(=O)—O—, and $Z^{35}$ is not —CH$_2$O— or —CF$_2$O—;
wherein alkanyl is an unsaturated alkyl group which is optionally mono- or polysubstituted, identically or differently, by halogen or —CN.

53. A compound according to claim 1, wherein said compound is of Formula I-D:

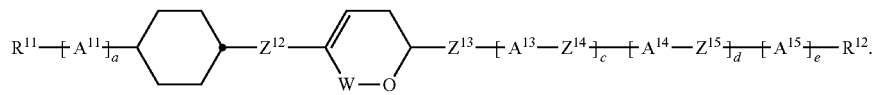

I-D

54. A compound according to claim 1, wherein said compound is of Formula I-E:

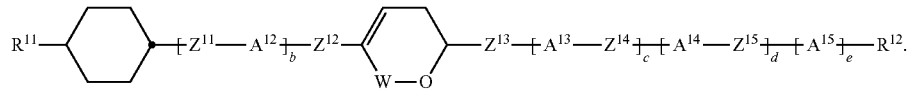

I-E

55. A compound according to claim 1, wherein said compound is of Formula I-J:

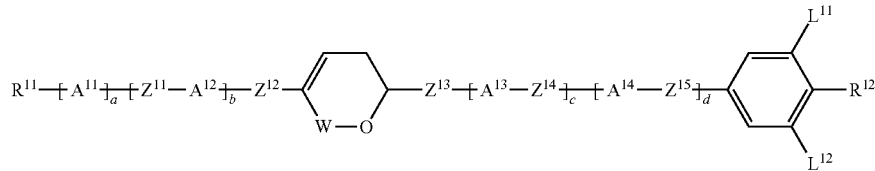

I-J wherein $L^{11}$ and $L^{12}$, independently of one another, are each H or F.

56. A compound according to claim 1, wherein said compound is of Formula I-K:

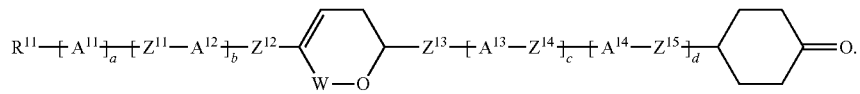

I-K

57. A compound according to claim 1, wherein said compound is of Formula I-L:

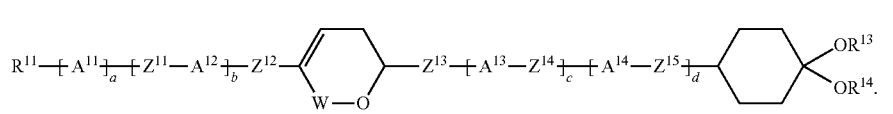

I-L

58. A compound according to claim 1, wherein said compound is of Formula I-M:

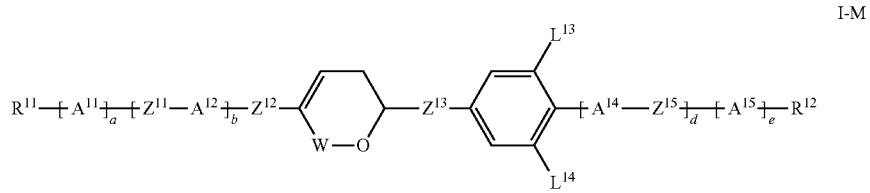

I-M wherein $L^{13}$ and $L^{14}$, independently of one another, are each H or F.

59. A compound according to claim 1, wherein said compound is of Formula I-N:

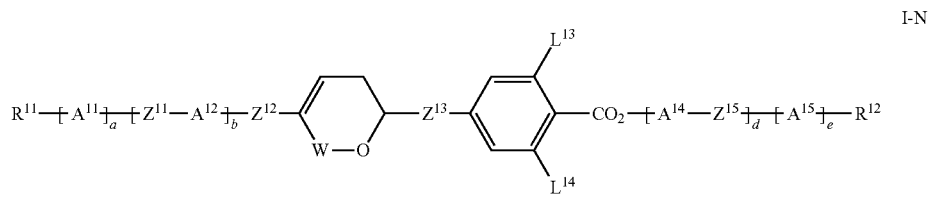

I-N wherein $L^{13}$ and $L^{14}$, independently of one another, are each H or F.

60. A compound according to claim 1, wherein said compound is of Formula I-O:

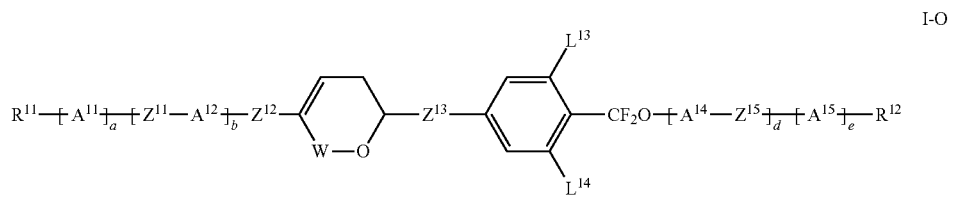

I-O wherein $L^{13}$ and $L^{14}$, independently of one another, are each H or F.

61. A compound according to claim 1, wherein said compound is of Formula I-P:

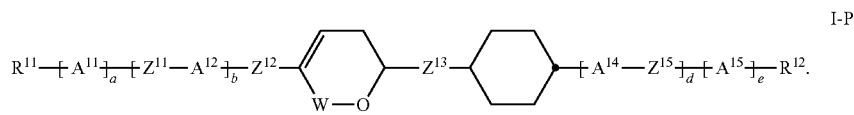

I-P

62. A compound according to claim 1, wherein said compound is of Formula I-Q:

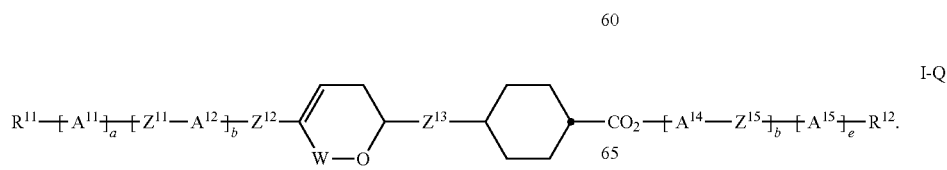

I-Q

63. A compound according to claim 1, wherein said compound is of Formula I-R:
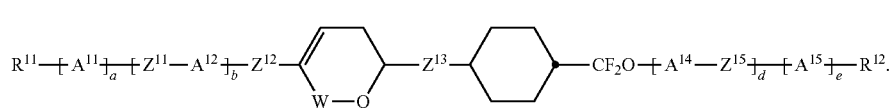
I-R
64. A compound according to claim 1, wherein said compound is of Formula I-S:
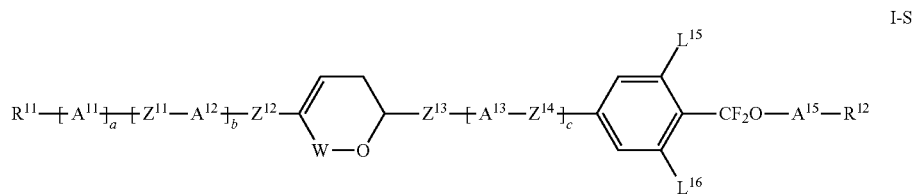
I-S
wherein $L^{15}$ and $L^{16}$, independently of one another, are each H or F.
65. A compound according to claim 1, wherein said compound is of Formula I-T:
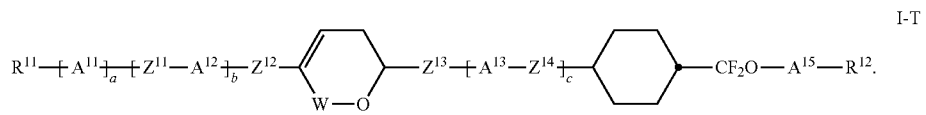
I-T
* * * * *

UNITED STATES PATENT AND TRADEMARK OFFICE
CERTIFICATE OF CORRECTION

PATENT NO. : 7,888,519 B2
APPLICATION NO. : 10/854718
DATED : February 15, 2011
INVENTOR(S) : Poetsch et al.

It is certified that error appears in the above-identified patent and that said Letters Patent is hereby corrected as shown below:

Column 135, Line 65: delete both formulas and replace with:

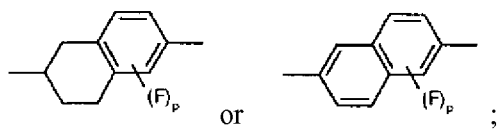

Column 136, Line 25: delete both formulas and replace with:

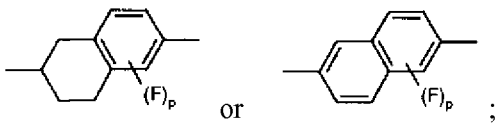

Column 138, Line 50: delete both formulas and replace with:

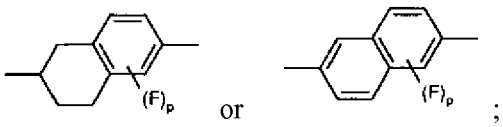

Column 139, Line 10: delete both formulas and replace with:

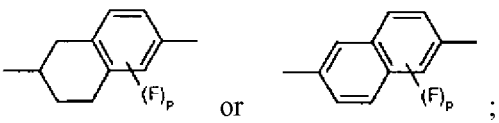

Signed and Sealed this
Thirteenth Day of March, 2012

David J. Kappos
*Director of the United States Patent and Trademark Office*

Column 141, Line 20: delete both formulas and replace with:

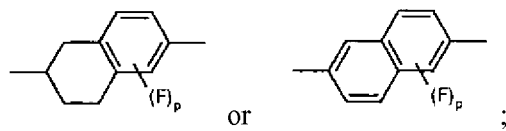 or ;

Column 141, Line 35: delete both formulas and replace with:

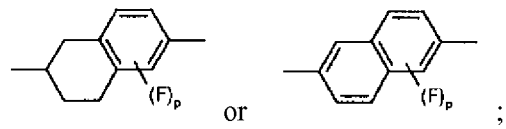 or ;

Column 144, Line 36: delete the second formula and replace with:

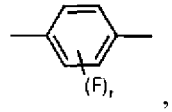 ,

Column 144, Line 55: delete both formulas and replace with:

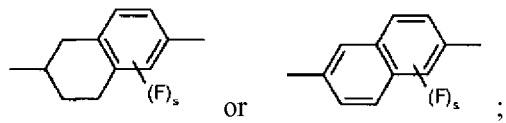 or ;

Column 145, Line 5: delete second formula and replace with:

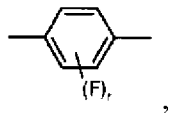 ,

Column 145, Line 10: delete both formulas and replace with:

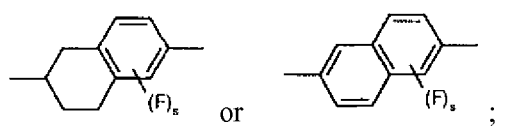 or ;

Column 145, Line 20: delete the first formula and replace with:

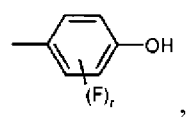 ,